US012616593B2

(12) United States Patent
Schreck et al.

(10) Patent No.: US 12,616,593 B2
(45) Date of Patent: May 5, 2026

(54) HEART VALVE PROSTHESIS DELIVERY SYSTEM AND METHOD FOR DELIVERY OF HEART VALVE PROSTHESIS WITH INTRODUCER SHEATH AND LOADING SYSTEM

(71) Applicant: JenaValve Technology, Inc., Irvine, CA (US)

(72) Inventors: Stefan Schreck, Duvall, WA (US); Hussain Rangwala, Villa Park, CA (US); Payam Saffari, Aliso Viejo, CA (US); Makensley Lordeus, Phoenix, AZ (US); Vincent Ming Hai Chow, Irvine, CA (US); Kevin Han Tang Chu, Tustin, CA (US)

(73) Assignee: JenaValve Technology, Inc., Irvine, CA (US)

( * ) Notice: Subject to any disclaimer, the term of this patent is extended or adjusted under 35 U.S.C. 154(b) by 1016 days.

(21) Appl. No.: 17/377,254

(22) Filed: Jul. 15, 2021

(65) Prior Publication Data

US 2021/0401603 A1 Dec. 30, 2021

Related U.S. Application Data

(63) Continuation of application No. 16/099,793, filed as application No. PCT/IB2017/052718 on May 10, 2017, now Pat. No. 11,065,138.

(Continued)

(51) Int. Cl.
*A61F 2/24* (2006.01)
*A61F 2/00* (2006.01)
(Continued)

(52) U.S. Cl.
CPC ........... *A61F 2/966* (2013.01); *A61F 2/0095* (2013.01); *A61F 2/243* (2013.01); *A61F 2/2436* (2013.01);
(Continued)

(58) Field of Classification Search
CPC .... A61F 2/0095; A61F 2/2427; A61F 2/2436; A61F 2/243; A61F 2/95; A61F 2/9517;
(Continued)

(56) References Cited

U.S. PATENT DOCUMENTS 15,192 A 6/1856 Peale
388,776 A 8/1888 Hall
(Continued)

FOREIGN PATENT DOCUMENTS

AU 757647 B2 2/2003
AU 776895 B2 9/2004
(Continued)

OTHER PUBLICATIONS

US 6,331,185 B1, 12/2001, Gambale et al. (withdrawn)
(Continued)

*Primary Examiner* — Diane D Yabut
*Assistant Examiner* — Christian D Knauss
(74) *Attorney, Agent, or Firm* — Greenberg Traurig, LLP; Christopher C. Bolten; Robert D. Ward

(57) ABSTRACT

The present disclosure relates to a delivery catheter and the stepwise release of a stent from the catheter into the vasculature of a patient, as well as a loading device for a transcatheter heart valve (THV) prosthesis.

13 Claims, 38 Drawing Sheets

Related U.S. Application Data

(60) Provisional application No. 62/491,391, filed on Apr. 28, 2017, provisional application No. 62/336,153, filed on May 13, 2016.

(51) Int. Cl.
A61F 2/966 (2013.01)
A61F 2/95 (2013.01)

(52) U.S. Cl.
CPC ..... *A61F 2002/9505* (2013.01); *A61F 2/9522* (2020.05); *A61F 2002/9665* (2013.01); *A61F 2250/0062* (2013.01); *A61F 2250/0064* (2013.01); *A61F 2250/0092* (2013.01)

(58) Field of Classification Search
CPC ........ A61F 2/962; A61F 2/966; A61F 2/9661; A61F 2/9662; A61F 2002/9505; A61F 2002/9534; A61F 2002/9665
See application file for complete search history.

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Edward et al. |
| 3,099,016 A | 7/1963 | Lowell et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Lowell et al. |
| 3,367,364 A | 2/1968 | Cruz, Jr. et al. |
| 3,409,013 A | 11/1968 | Henry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,562,597 A | 1/1986 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |

(56) References Cited

U.S. PATENT DOCUMENTS

| | | | |
|---|---|---|---|
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,595,571 A | 1/1997 | Jaffe et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |
| 5,653,749 A | 8/1997 | Love et al. |
| 5,655,548 A | 8/1997 | Nelson et al. |

(56)     References Cited

U.S. PATENT DOCUMENTS

| | | |
|---|---|---|
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,836,869 A | 11/1998 | Kudo et al. |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |
| 5,961,549 A | 10/1999 | Nguyen et al. |
| 5,964,405 A | 10/1999 | Benary et al. |

(56) References Cited

U.S. PATENT DOCUMENTS

| | | |
|---|---|---|
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | McIlroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | Vantassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |
| 6,190,353 B1 | 2/2001 | Makower et al. |
| 6,190,393 B1 | 2/2001 | Bevier et al. |
| 6,190,405 B1 | 2/2001 | Culombo et al. |

(56)                    References Cited

U.S. PATENT DOCUMENTS

| | | |
|---|---|---|
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | Mackellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |
| 6,402,740 B1 | 6/2002 | Ellis et al. |
| 6,406,488 B1 | 6/2002 | Tweden et al. |
| 6,406,491 B1 | 6/2002 | Vanney |

(56) References Cited

U.S. PATENT DOCUMENTS

| | | | |
|---|---|---|---|
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B2 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier et al. |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,593 B1 | 6/2003 | Daum |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,546 B1 | 11/2003 | Nash et al. |
| 6,652,555 B1 | 11/2003 | Vantassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |
| 6,660,003 B1 | 12/2003 | DeVore et al. |
| 6,660,024 B1 | 12/2003 | Flaherty et al. |

(56) References Cited

U.S. PATENT DOCUMENTS

| | | | |
|---|---|---|---|
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,841 B1 | 3/2004 | Wright et al. |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Mårtensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |
| 6,953,332 B1 | 10/2005 | Kurk et al. |

(56) References Cited

U.S. PATENT DOCUMENTS

| | | | |
|---|---|---|---|
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |
| 7,393,358 B2 | 7/2008 | Malewicz |

(56) References Cited

U.S. PATENT DOCUMENTS

| | | | |
|---|---|---|---|
| 7,393,360 B2 | 7/2008 | Spenser et al. |
| 7,396,364 B2 | 7/2008 | Moaddeb et al. |
| 7,399,315 B2 | 7/2008 | Iobbi |
| 7,402,171 B2 | 7/2008 | Osborne et al. |
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,282 B2 | 12/2008 | Shelso |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | Lê et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,708,775 B2 | 5/2010 | Rowe et al. |
| 7,712,606 B2 | 5/2010 | Salahieh et al. |
| 7,715,903 B2 | 5/2010 | Hartley et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |

(56) References Cited

U.S. PATENT DOCUMENTS

| | | | |
|---|---|---|---|
| 7,972,359 | B2 | 7/2011 | Kreidler |
| 7,972,376 | B1 | 7/2011 | Dove et al. |
| 7,972,378 | B2 | 7/2011 | Tabor et al. |
| 7,988,724 | B2 | 8/2011 | Salahieh et al. |
| 7,993,386 | B2 | 8/2011 | Elliott |
| 8,002,824 | B2 | 8/2011 | Jenson et al. |
| 8,002,825 | B2 | 8/2011 | Letac et al. |
| 8,012,198 | B2 | 9/2011 | Hill et al. |
| 8,021,421 | B2 | 9/2011 | Fogarty et al. |
| RE42,818 | E | 10/2011 | Cali et al. |
| RE42,857 | E | 10/2011 | Cali et al. |
| 8,038,704 | B2 | 10/2011 | Sherburne |
| 8,038,709 | B2 | 10/2011 | Palasis et al. |
| 8,043,450 | B2 | 10/2011 | Cali et al. |
| 8,048,153 | B2 | 11/2011 | Salahieh et al. |
| 8,052,715 | B2 | 11/2011 | Quinn et al. |
| 8,052,749 | B2 | 11/2011 | Salahieh et al. |
| 8,052,750 | B2 | 11/2011 | Tuval et al. |
| 8,057,540 | B2 | 11/2011 | Letac et al. |
| 8,062,355 | B2 | 11/2011 | Figulla et al. |
| 8,062,536 | B2 | 11/2011 | Liu et al. |
| 8,062,537 | B2 | 11/2011 | Tuominen et al. |
| 8,062,749 | B2 | 11/2011 | Shelestak et al. |
| 8,070,799 | B2 | 12/2011 | Righini et al. |
| 8,075,641 | B2 | 12/2011 | Aravanis et al. |
| 8,083,788 | B2 | 12/2011 | Acosta et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,128,676 | B2 | 3/2012 | Cummings |
| 8,128,681 | B2 | 3/2012 | Shoemaker et al. |
| 8,133,217 | B2 | 3/2012 | Stokes et al. |
| 8,133,270 | B2 | 3/2012 | Kheradvar et al. |
| 8,136,659 | B2 | 3/2012 | Salahieh et al. |
| 8,137,394 | B2 | 3/2012 | Stocker et al. |
| 8,137,398 | B2 | 3/2012 | Tuval et al. |
| 8,147,534 | B2 | 4/2012 | Berez et al. |
| 8,157,853 | B2 | 4/2012 | Laske et al. |
| 8,167,894 | B2 | 5/2012 | Miles et al. |
| 8,172,896 | B2 | 5/2012 | McNamara et al. |
| 8,182,528 | B2 | 5/2012 | Salahieh et al. |
| 8,192,351 | B2 | 6/2012 | Fishler et al. |
| 8,206,437 | B2 | 6/2012 | Bonhoeffer et al. |
| 8,211,107 | B2 | 7/2012 | Parks et al. |
| 8,216,174 | B2 | 7/2012 | Wilk et al. |
| 8,216,301 | B2 | 7/2012 | Bonhoeffer et al. |
| 8,221,493 | B2 | 7/2012 | Boyle et al. |
| 8,226,707 | B2 | 7/2012 | White |
| 8,226,710 | B2 | 7/2012 | Nguyen et al. |
| 8,230,717 | B2 | 7/2012 | Matonick |
| 8,231,670 | B2 | 7/2012 | Salahieh et al. |
| 8,236,049 | B2 | 8/2012 | Rowe et al. |
| 8,236,241 | B2 | 8/2012 | Carpentier et al. |
| 8,246,675 | B2 | 8/2012 | Zegdi |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,277,500 | B2 | 10/2012 | Schmid et al. |
| 8,287,584 | B2 | 10/2012 | Salahieh et al. |
| 8,303,653 | B2 | 11/2012 | Bonhoeffer et al. |
| 8,308,798 | B2 | 11/2012 | Pintor et al. |
| 8,317,858 | B2 | 11/2012 | Straubinger et al. |
| 8,323,335 | B2 | 12/2012 | Rowe et al. |
| 8,328,868 | B2 | 12/2012 | Paul et al. |
| 8,343,136 | B2 | 1/2013 | Howat et al. |
| 8,343,213 | B2 | 1/2013 | Salahieh et al. |
| 8,348,995 | B2 | 1/2013 | Tuval et al. |
| 8,348,996 | B2 | 1/2013 | Tuval et al. |
| 8,348,999 | B2 | 1/2013 | Kheradvar et al. |
| 8,357,387 | B2 | 1/2013 | Dove et al. |
| 8,366,767 | B2 | 2/2013 | Zhang |
| 8,372,134 | B2 | 2/2013 | Schlick et al. |
| 8,376,865 | B2 | 2/2013 | Forster et al. |
| 8,377,117 | B2 | 2/2013 | Keidar et al. |
| 8,382,822 | B2 | 2/2013 | Pavcnik et al. |
| 8,398,704 | B2 | 3/2013 | Straubinger et al. |
| 8,398,708 | B2 | 3/2013 | Meiri et al. |
| 8,403,983 | B2 | 3/2013 | Quadri et al. |
| 8,414,641 | B2 | 4/2013 | Stocker et al. |
| 8,414,643 | B2 | 4/2013 | Tuval et al. |
| 8,414,644 | B2 | 4/2013 | Quadri et al. |
| 8,414,645 | B2 | 4/2013 | Dwork et al. |
| 8,439,961 | B2 | 5/2013 | Jagger et al. |
| 8,445,278 | B2 | 5/2013 | Everaerts et al. |
| 8,460,365 | B2 | 6/2013 | Haverkost et al. |
| 8,465,540 | B2 | 6/2013 | Straubinger et al. |
| 8,468,667 | B2 | 6/2013 | Straubinger et al. |
| 8,470,023 | B2 | 6/2013 | Eidenschink et al. |
| 8,491,650 | B2 | 7/2013 | Wiemeyer et al. |
| 8,512,394 | B2 | 8/2013 | Schmid et al. |
| 8,512,399 | B2 | 8/2013 | Lafontaine |
| 8,512,400 | B2 | 8/2013 | Tran et al. |
| 8,512,401 | B2 | 8/2013 | Murray, III et al. |
| 8,523,936 | B2 | 9/2013 | Schmid et al. |
| 8,535,368 | B2 | 9/2013 | Headley, Jr. et al. |
| 8,540,762 | B2 | 9/2013 | Schmid et al. |
| 8,545,547 | B2 | 10/2013 | Schmid et al. |
| 8,545,552 | B2 | 10/2013 | Garrison et al. |
| 8,551,160 | B2 | 10/2013 | Figulla et al. |
| 8,556,880 | B2 | 10/2013 | Freyman et al. |
| 8,556,966 | B2 | 10/2013 | Jenson |
| 8,568,475 | B2 | 10/2013 | Nguyen et al. |
| 8,579,936 | B2 | 11/2013 | Abbott et al. |
| 8,579,962 | B2 | 11/2013 | Salahieh et al. |
| 8,579,965 | B2 | 11/2013 | Bonhoeffer et al. |
| 8,585,756 | B2 | 11/2013 | Bonhoeffer et al. |
| 8,585,759 | B2 | 11/2013 | Bumbalough |
| 8,591,570 | B2 | 11/2013 | Revuelta et al. |
| 8,597,226 | B2 | 12/2013 | Wilk et al. |
| 8,603,159 | B2 | 12/2013 | Seguin et al. |
| 8,603,160 | B2 | 12/2013 | Salahieh et al. |
| 8,617,235 | B2 | 12/2013 | Schmid et al. |
| 8,617,236 | B2 | 12/2013 | Paul et al. |
| 8,623,074 | B2 | 1/2014 | Ryan |
| 8,623,075 | B2 | 1/2014 | Murray, III et al. |
| 8,623,076 | B2 | 1/2014 | Salahieh et al. |
| 8,623,078 | B2 | 1/2014 | Salahieh et al. |
| 8,628,562 | B2 | 1/2014 | Cummings |
| 8,628,571 | B1 | 1/2014 | Hacohen et al. |
| 8,647,381 | B2 | 2/2014 | Essinger et al. |
| 8,668,733 | B2 | 3/2014 | Haug et al. |
| 8,672,997 | B2 | 3/2014 | Drasler et al. |
| 8,679,174 | B2 | 3/2014 | Ottma et al. |
| 8,685,077 | B2 | 4/2014 | Laske et al. |
| 8,696,743 | B2 | 4/2014 | Holecek et al. |
| 8,721,713 | B2 | 5/2014 | Tower et al. |
| 8,721,717 | B2 | 5/2014 | Shoemaker et al. |
| 8,734,508 | B2 | 5/2014 | Hastings et al. |
| 8,758,430 | B2 | 6/2014 | Ferrari et al. |
| 8,764,818 | B2 | 7/2014 | Gregg |
| 8,778,020 | B2 | 7/2014 | Gregg et al. |
| 8,790,395 | B2 | 7/2014 | Straubinger et al. |
| 8,795,305 | B2 | 8/2014 | Martin et al. |
| 8,795,356 | B2 | 8/2014 | Quadri et al. |
| 8,808,356 | B2 | 8/2014 | Braido et al. |
| 8,808,364 | B2 | 8/2014 | Palasis et al. |
| RE45,130 | E | 9/2014 | Figulla et al. |
| 8,828,078 | B2 | 9/2014 | Salahieh et al. |
| 8,828,079 | B2 | 9/2014 | Thielen et al. |
| 8,840,662 | B2 | 9/2014 | Salahieh et al. |
| 8,840,663 | B2 | 9/2014 | Salahieh et al. |
| 8,845,721 | B2 | 9/2014 | Braido et al. |
| 8,851,286 | B2 | 10/2014 | Chang et al. |
| 8,852,272 | B2 | 10/2014 | Gross et al. |
| 8,858,620 | B2 | 10/2014 | Salahieh et al. |
| 8,894,703 | B2 | 11/2014 | Salahieh et al. |
| 8,932,349 | B2 | 1/2015 | Jenson et al. |
| 8,940,014 | B2 | 1/2015 | Gamarra et al. |
| 8,951,243 | B2 | 2/2015 | Crisostomo et al. |
| 8,951,299 | B2 | 2/2015 | Paul et al. |
| 8,956,383 | B2 | 2/2015 | Aklog et al. |
| 8,992,608 | B2 | 3/2015 | Haug et al. |
| 8,998,976 | B2 | 4/2015 | Gregg et al. |
| 9,005,273 | B2 | 4/2015 | Salahieh et al. |

(56) References Cited

U.S. PATENT DOCUMENTS

| | | | |
|---|---|---|---|
| 9,011,521 B2 | 4/2015 | Haug et al. | |
| 9,023,099 B2 | 5/2015 | Duffy et al. | |
| 9,028,542 B2 | 5/2015 | Hill et al. | |
| 9,039,756 B2 | 5/2015 | White | |
| 9,044,318 B2 | 6/2015 | Straubinger et al. | |
| 9,131,926 B2 | 9/2015 | Crisostomo et al. | |
| 9,138,315 B2 | 9/2015 | Straubinger et al. | |
| 9,149,358 B2 | 10/2015 | Tabor et al. | |
| 9,168,130 B2 | 10/2015 | Straubinger et al. | |
| 9,168,131 B2 | 10/2015 | Yohanan et al. | |
| 9,168,136 B2 | 10/2015 | Yang et al. | |
| RE45,790 E | 11/2015 | Figulla et al. | |
| 9,180,005 B1 | 11/2015 | Lashinski et al. | |
| 9,186,482 B2 | 11/2015 | Dorn | |
| 9,211,266 B2 | 12/2015 | Iwazawa et al. | |
| 9,216,082 B2 | 12/2015 | Von Segesser et al. | |
| 9,248,037 B2 | 2/2016 | Roeder et al. | |
| 9,265,608 B2 | 2/2016 | Miller et al. | |
| 9,277,991 B2 | 3/2016 | Salahieh et al. | |
| 9,277,993 B2 | 3/2016 | Gamarra et al. | |
| 9,295,551 B2 | 3/2016 | Straubinger et al. | |
| 9,301,840 B2 | 4/2016 | Nguyen et al. | |
| 9,301,843 B2 | 4/2016 | Richardson et al. | |
| 9,308,085 B2 | 4/2016 | Salahieh et al. | |
| 9,320,599 B2 | 4/2016 | Salahieh et al. | |
| 9,326,853 B2 | 5/2016 | Olson et al. | |
| 9,358,106 B2 | 6/2016 | Salahieh et al. | |
| 9,358,110 B2 | 6/2016 | Paul et al. | |
| 9,370,419 B2 | 6/2016 | Hill et al. | |
| 9,370,421 B2 | 6/2016 | Crisostomo et al. | |
| 9,387,076 B2 | 7/2016 | Paul et al. | |
| 9,393,094 B2 | 7/2016 | Salahieh et al. | |
| 9,393,113 B2 | 7/2016 | Salahieh et al. | |
| 9,393,114 B2 | 7/2016 | Sutton et al. | |
| 9,393,115 B2 | 7/2016 | Tabor et al. | |
| 9,415,567 B2 | 8/2016 | Sogard et al. | |
| 9,421,083 B2 | 8/2016 | Eidenschink et al. | |
| 9,439,759 B2 | 9/2016 | Straubinger et al. | |
| 9,463,084 B2 | 10/2016 | Stinson | |
| 9,474,598 B2 | 10/2016 | Gregg et al. | |
| 9,474,609 B2 | 10/2016 | Haverkost et al. | |
| 9,492,276 B2 | 11/2016 | Lee et al. | |
| 9,510,945 B2 | 12/2016 | Sutton et al. | |
| 9,510,947 B2 | 12/2016 | Straubinger et al. | |
| 9,526,609 B2 | 12/2016 | Salahieh et al. | |
| 9,532,872 B2 | 1/2017 | Salahieh et al. | |
| 9,539,091 B2 | 1/2017 | Yang et al. | |
| 9,554,924 B2 | 1/2017 | Schlick et al. | |
| 9,597,432 B2 | 3/2017 | Nakamura | |
| 9,649,212 B2 | 5/2017 | Fargahi | |
| 9,675,413 B2 | 6/2017 | Deem et al. | |
| 9,717,593 B2 | 8/2017 | Alkhatib et al. | |
| 9,744,031 B2 | 8/2017 | Girard et al. | |
| D800,908 S | 10/2017 | Hariton et al. | |
| 9,775,709 B2 | 10/2017 | Miller et al. | |
| 9,788,945 B2 | 10/2017 | Ottma et al. | |
| 9,861,476 B2 | 1/2018 | Salahieh et al. | |
| 9,867,694 B2 | 1/2018 | Girard et al. | |
| 9,867,699 B2 | 1/2018 | Straubinger et al. | |
| 9,872,768 B2 | 1/2018 | Paul et al. | |
| 9,878,127 B2 | 1/2018 | Damm et al. | |
| 9,889,002 B2 | 2/2018 | Bonhoeffer et al. | |
| 9,901,445 B2 | 2/2018 | Backus et al. | |
| 9,918,835 B2 | 3/2018 | Guyenot et al. | |
| 9,949,824 B2 | 4/2018 | Bonhoeffer et al. | |
| 9,956,075 B2 | 5/2018 | Salahieh et al. | |
| 9,968,761 B2 | 5/2018 | Brecker | |
| 9,987,133 B2 | 6/2018 | Straubinger et al. | |
| 10,092,324 B2 | 10/2018 | Gillespie et al. | |
| 10,143,552 B2 | 12/2018 | Wallace et al. | |
| 10,154,901 B2 | 12/2018 | Straubinger et al. | |
| 10,321,987 B2 | 6/2019 | Wang et al. | |
| 10,363,134 B2 | 7/2019 | Figulla et al. | |
| 10,543,084 B2 | 1/2020 | Guyenot et al. | |
| 10,575,947 B2 | 3/2020 | Straubinger et al. | |
| 10,638,918 B2 | 5/2020 | Atarot et al. | |
| 10,653,427 B2 | 5/2020 | Goldfarb et al. | |
| 10,702,382 B2 | 7/2020 | Straubinger et al. | |
| 10,709,555 B2 | 7/2020 | Schreck et al. | |
| 10,856,978 B2 | 12/2020 | Straubinger et al. | |
| 10,856,987 B2 | 12/2020 | Cabiri et al. | |
| 11,065,138 B2 | 7/2021 | Schreck et al. | |
| 11,147,669 B2 | 10/2021 | Straubinger et al. | |
| 11,154,398 B2 | 10/2021 | Straubinger et al. | |
| 11,185,405 B2 | 11/2021 | Girard et al. | |
| 11,197,754 B2 | 12/2021 | Saffari et al. | |
| 11,266,497 B2 | 3/2022 | Cao et al. | |
| 11,357,624 B2 | 6/2022 | Guyenot et al. | |
| 11,911,264 B2 | 2/2024 | Chau et al. | |
| 11,951,005 B2 | 4/2024 | Gross et al. | |
| 12,232,957 B2 | 2/2025 | Straubinger et al. | |
| 12,318,281 B2 | 6/2025 | Girard et al. | |
| 12,343,255 B2 | 7/2025 | Schreck et al. | |
| 12,414,854 B2 | 9/2025 | Straubinger et al. | |
| 12,433,745 B2 | 10/2025 | Saffari et al. | |
| 2001/0000041 A1 | 3/2001 | Selmon et al. | |
| 2001/0001314 A1 | 5/2001 | Davison et al. | |
| 2001/0002445 A1 | 5/2001 | Vesely | |
| 2001/0004683 A1 | 6/2001 | Gambale et al. | |
| 2001/0004690 A1 | 6/2001 | Gambale et al. | |
| 2001/0004699 A1 | 6/2001 | Gittings et al. | |
| 2001/0007956 A1 | 7/2001 | Letac et al. | |
| 2001/0008969 A1 | 7/2001 | Evans et al. | |
| 2001/0010017 A1 | 7/2001 | Letac et al. | |
| 2001/0011187 A1 | 8/2001 | Pavcnik et al. | |
| 2001/0011189 A1 | 8/2001 | Drasler et al. | |
| 2001/0012948 A1 | 8/2001 | Vanney | |
| 2001/0014813 A1 | 8/2001 | Saadat et al. | |
| 2001/0016700 A1 | 8/2001 | Eno et al. | |
| 2001/0018596 A1 | 8/2001 | Selmon et al. | |
| 2001/0020172 A1 | 9/2001 | Selmon et al. | |
| 2001/0021872 A1 | 9/2001 | Bailey et al. | |
| 2001/0025196 A1 | 9/2001 | Chinn et al. | |
| 2001/0025643 A1 | 10/2001 | Foley | |
| 2001/0027287 A1 | 10/2001 | Shmulewitz et al. | |
| 2001/0027338 A1 | 10/2001 | Greenberg | |
| 2001/0027339 A1 | 10/2001 | Boatman et al. | |
| 2001/0029385 A1 | 10/2001 | Shennib et al. | |
| 2001/0032013 A1 | 10/2001 | Marton | |
| 2001/0034547 A1 | 10/2001 | Hall et al. | |
| 2001/0037117 A1 | 11/2001 | Gambale et al. | |
| 2001/0037141 A1 | 11/2001 | Yee et al. | |
| 2001/0037149 A1 | 11/2001 | Wilk | |
| 2001/0039426 A1 | 11/2001 | Makower et al. | |
| 2001/0039445 A1 | 11/2001 | Hall et al. | |
| 2001/0039450 A1 | 11/2001 | Pavcnik et al. | |
| 2001/0041902 A1 | 11/2001 | Lepulu et al. | |
| 2001/0041928 A1 | 11/2001 | Pavcnik et al. | |
| 2001/0041930 A1 | 11/2001 | Globerman et al. | |
| 2001/0044631 A1 | 11/2001 | Akin et al. | |
| 2001/0044634 A1 | 11/2001 | Don Michael et al. | |
| 2001/0044647 A1 | 11/2001 | Pinchuk et al. | |
| 2001/0044652 A1 | 11/2001 | Moore | |
| 2001/0044656 A1 | 11/2001 | Williamson, IV et al. | |
| 2001/0047165 A1 | 11/2001 | Makower et al. | |
| 2001/0049523 A1 | 12/2001 | DeVore et al. | |
| 2001/0051822 A1 | 12/2001 | Stack et al. | |
| 2001/0053930 A1 | 12/2001 | Kugler et al. | |
| 2001/0053932 A1 | 12/2001 | Phelps et al. | |
| 2002/0002349 A1 | 1/2002 | Flaherty et al. | |
| 2002/0002396 A1 | 1/2002 | Fulkerson | |
| 2002/0002401 A1 | 1/2002 | McGuckin, Jr. et al. | |
| 2002/0004662 A1 | 1/2002 | Wilk | |
| 2002/0004663 A1 | 1/2002 | Gittings et al. | |
| 2002/0007138 A1 | 1/2002 | Wilk et al. | |
| 2002/0010489 A1 | 1/2002 | Grayzel et al. | |
| 2002/0010508 A1 | 1/2002 | Chobotov | |
| 2002/0026233 A1 | 2/2002 | Shaknovich | |
| 2002/0029014 A1 | 3/2002 | Jayaraman | |
| 2002/0029079 A1 | 3/2002 | Kim et al. | |
| 2002/0029981 A1 | 3/2002 | Nigam | |
| 2002/0032476 A1 | 3/2002 | Gambale et al. | |
| 2002/0032478 A1 | 3/2002 | Boekstegers et al. | |
| 2002/0032480 A1 | 3/2002 | Spence et al. | |

(56) References Cited

U.S. PATENT DOCUMENTS

| | | |
|---|---|---|
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045928 A1 | 4/2002 | Boekstegers |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |
| 2002/0099405 A1* | 7/2002 | Yurek .................. A61F 2/95 |
| | | 606/198 |
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0128552 A1 | 9/2002 | Nowlin et al. |
| 2002/0133183 A1 | 9/2002 | Lentz et al. |
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boekstegers |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1 | 4/2003 | Sutherland |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0153971 A1 | 8/2003 | Chandrasekaran |

(56)　　　　References Cited

U.S. PATENT DOCUMENTS

| | | |
|---|---|---|
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163193 A1 | 8/2003 | Widenhouse |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167619 A1 | 8/2004 | Case et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186507 A1 | 9/2004 | Hall et al. |
| 2004/0186557 A1 | 9/2004 | Gambale et al. |

(56)  References Cited

U.S. PATENT DOCUMENTS

| | | |
|---|---|---|
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0102020 A1 | 5/2005 | Grayzel et al. |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149159 A1 | 7/2005 | Andreas et al. |
| 2005/0149166 A1 | 7/2005 | Schaeffer et al. |

(56)  References Cited

U.S. PATENT DOCUMENTS

| | | |
|---|---|---|
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1 | 6/2006 | Rosenman et al. |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155363 A1 | 7/2006 | LaDuca et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Leonard Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276872 A1 | 12/2006 | Arbefeuille et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |
| 2007/0021826 A1 | 1/2007 | Case et al. |
| 2007/0027518 A1 | 2/2007 | Case et al. |
| 2007/0027520 A1 | 2/2007 | Sherburne |

(56)                    References Cited

U.S. PATENT DOCUMENTS

| | | |
|---|---|---|
| 2007/0027533 A1 | 2/2007 | Douk |
| 2007/0027535 A1 | 2/2007 | Purdy, Jr. et al. |
| 2007/0032856 A1 | 2/2007 | Limon |
| 2007/0032879 A1 | 2/2007 | Levine et al. |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul, Jr. et al. |
| 2007/0061008 A1 | 3/2007 | Salahieh et al. |
| 2007/0073389 A1 | 3/2007 | Bolduc et al. |
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093888 A1 | 4/2007 | Thistle et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru et al. |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |
| 2008/0177381 A1 | 7/2008 | Navia et al. |
| 2008/0183273 A1 | 7/2008 | Mesana et al. |

(56)                References Cited

U.S. PATENT DOCUMENTS

| | | |
|---|---|---|
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262590 A1* | 10/2008 | Murray .................... A61F 2/95 623/1.11 |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1* | 3/2009 | Suri .................... A61F 2/2433 623/2.11 |
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0022948 A1 | 1/2010 | Wilson et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | Howat et al. |
| 2010/0057185 A1 | 3/2010 | Melsheimer et al. |
| 2010/0063573 A1 | 3/2010 | Hijlkema et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0028290 A1 | 2/2011 | Ozawa |
| 2011/0029066 A1 | 2/2011 | Gilad et al. |
| 2011/0034852 A1 | 2/2011 | Hausler et al. |
| 2011/0040366 A1 | 2/2011 | Goetz et al. |

(56) References Cited

U.S. PATENT DOCUMENTS

| | | |
|---|---|---|
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0118545 A1 | 5/2011 | Williams et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264203 A1 | 10/2011 | Dwork et al. |
| 2011/0276091 A1 | 11/2011 | Melanson et al. |
| 2011/0276121 A1 | 11/2011 | Levine |
| 2011/0276129 A1 | 11/2011 | Salahieh et al. |
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0143084 A1 | 6/2012 | Shoham |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0197391 A1 | 8/2012 | Alkhatib et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0265296 A1 | 10/2012 | McNamara et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0023984 A1 | 1/2013 | Conklin |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338595 A1 | 12/2013 | Voss |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121763 A1 | 5/2014 | Duffy et al. |
| 2014/0121766 A1 | 5/2014 | Salahieh et al. |
| 2014/0128969 A1 | 5/2014 | Hill et al. |
| 2014/0135909 A1 | 5/2014 | Carr et al. |
| 2014/0135912 A1 | 5/2014 | Salahieh et al. |
| 2014/0207229 A1 | 7/2014 | Shoemaker et al. |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |

(56)                References Cited

U.S. PATENT DOCUMENTS

| | | | |
|---|---|---|---|
| 2014/0249622 A1* | 9/2014 | Carmi | A61F 2/2418 |
| | | | 623/2.11 |
| 2014/0257473 A1 | 9/2014 | Rajamannan | |
| 2014/0277414 A1 | 9/2014 | Kheradvar | |
| 2014/0296962 A1 | 10/2014 | Cartledge et al. | |
| 2014/0309732 A1 | 10/2014 | Solem | |
| 2014/0316518 A1 | 10/2014 | Kheradvar et al. | |
| 2014/0330371 A1 | 11/2014 | Gloss et al. | |
| 2014/0343669 A1 | 11/2014 | Lane et al. | |
| 2014/0364799 A1 | 12/2014 | Beauvais et al. | |
| 2014/0379068 A1 | 12/2014 | Thielen et al. | |
| 2015/0012085 A1 | 1/2015 | Salahieh et al. | |
| 2015/0032056 A1 | 1/2015 | Okamura et al. | |
| 2015/0032198 A1 | 1/2015 | Folk | |
| 2015/0073540 A1 | 3/2015 | Salahieh et al. | |
| 2015/0073541 A1 | 3/2015 | Salahieh et al. | |
| 2015/0088252 A1 | 3/2015 | Jenson et al. | |
| 2015/0094804 A1 | 4/2015 | Bonhoeffer et al. | |
| 2015/0105857 A1 | 4/2015 | Bonhoeffer et al. | |
| 2015/0127092 A1 | 5/2015 | Straubinger et al. | |
| 2015/0127094 A1 | 5/2015 | Salahieh et al. | |
| 2015/0142102 A1 | 5/2015 | Lafontaine et al. | |
| 2015/0148894 A1 | 5/2015 | Damm et al. | |
| 2015/0209142 A1 | 7/2015 | Paul et al. | |
| 2015/0209146 A1 | 7/2015 | Hill et al. | |
| 2015/0223933 A1 | 8/2015 | Haug et al. | |
| 2015/0238315 A1 | 8/2015 | Rabito et al. | |
| 2015/0245909 A1 | 9/2015 | Salahieh et al. | |
| 2015/0272731 A1 | 10/2015 | Racchini et al. | |
| 2015/0320557 A1 | 11/2015 | Sutton et al. | |
| 2015/0335423 A1 | 11/2015 | Gregg et al. | |
| 2015/0352252 A1 | 12/2015 | Nakamura et al. | |
| 2015/0359997 A1 | 12/2015 | Crisostomo et al. | |
| 2016/0022418 A1 | 1/2016 | Salahieh et al. | |
| 2016/0045306 A1 | 2/2016 | Agrawal et al. | |
| 2016/0045307 A1 | 2/2016 | Yohanan et al. | |
| 2016/0051362 A1 | 2/2016 | Cooper et al. | |
| 2016/0067040 A1 | 3/2016 | Agrawal et al. | |
| 2016/0120645 A1 | 5/2016 | Alon | |
| 2016/0135951 A1 | 5/2016 | Salahieh et al. | |
| 2016/0143731 A1 | 5/2016 | Backus et al. | |
| 2016/0158003 A1 | 6/2016 | Wallace et al. | |
| 2016/0166384 A1 | 6/2016 | Olson et al. | |
| 2016/0199184 A1 | 7/2016 | Ma et al. | |
| 2016/0206423 A1 | 7/2016 | O'Connor et al. | |
| 2016/0213467 A1 | 7/2016 | Backus et al. | |
| 2016/0220359 A1 | 8/2016 | Backus et al. | |
| 2016/0220360 A1 | 8/2016 | Lin et al. | |
| 2016/0220365 A1 | 8/2016 | Backus et al. | |
| 2016/0250024 A1 | 9/2016 | Hill et al. | |
| 2016/0256271 A1 | 9/2016 | Backus et al. | |
| 2016/0262878 A1 | 9/2016 | Backus et al. | |
| 2016/0278923 A1 | 9/2016 | Krans et al. | |
| 2016/0346107 A1 | 12/2016 | Matthison-Hansen et al. | |
| 2016/0354203 A1 | 12/2016 | Tuval et al. | |
| 2016/0374793 A1 | 12/2016 | Lafontaine et al. | |
| 2016/0376063 A1 | 12/2016 | Salahieh et al. | |
| 2017/0000609 A1 | 1/2017 | Gross et al. | |
| 2017/0007400 A1 | 1/2017 | Sogard et al. | |
| 2017/0027654 A1 | 2/2017 | Frimer et al. | |
| 2017/0027693 A1 | 2/2017 | Paul et al. | |
| 2017/0049563 A1 | 2/2017 | Straubinger et al. | |
| 2017/0049568 A1 | 2/2017 | Straubinger et al. | |
| 2017/0056172 A1 | 3/2017 | Salahieh et al. | |
| 2017/0065410 A1 | 3/2017 | Straubinger et al. | |
| 2017/0087343 A1 | 3/2017 | Assaf et al. | |
| 2017/0095595 A1 | 4/2017 | Nakamura | |
| 2017/0143481 A1 | 5/2017 | Morriss et al. | |
| 2017/0189177 A1* | 7/2017 | Schweich, Jr. | A61F 2/2436 |
| 2017/0212723 A1 | 7/2017 | Atarot et al. | |
| 2017/0265849 A1 | 9/2017 | Assaf et al. | |
| 2017/0325954 A1 | 11/2017 | Perszyk | |
| 2017/0333230 A1 | 11/2017 | Folan et al. | |
| 2017/0348013 A1 | 12/2017 | Mottola et al. | |
| 2018/0116843 A1 | 5/2018 | Schreck et al. | |
| 2018/0325604 A1 | 11/2018 | Atarot et al. | |
| 2018/0368976 A1 | 12/2018 | Bonhoeffer et al. | |
| 2019/0328522 A1 | 10/2019 | Straubinger et al. | |
| 2020/0054449 A1 | 2/2020 | Min et al. | |
| 2020/0383717 A1 | 12/2020 | Lederman et al. | |
| 2021/0038313 A1 | 2/2021 | Sholev et al. | |
| 2021/0322153 A1 | 10/2021 | Tuval et al. | |
| 2022/0061987 A1 | 3/2022 | Duffy | |
| 2022/0079747 A1 | 3/2022 | Girard et al. | |
| 2022/0192765 A1 | 6/2022 | Brasset et al. | |
| 2022/0304803 A1 | 9/2022 | Guyenot et al. | |
| 2024/0008978 A1 | 1/2024 | Nawalakhe et al. | |
| 2024/0148503 A1 | 5/2024 | Chu et al. | |
| 2024/0164902 A1 | 5/2024 | Lee et al. | |
| 2024/0164903 A1 | 5/2024 | Chu et al. | |
| 2025/0288410 A1 | 9/2025 | Girard et al. | |

FOREIGN PATENT DOCUMENTS

| | | | |
|---|---|---|---|
| AU | 777443 B2 | 10/2004 | |
| AU | 778831 B2 | 12/2004 | |
| AU | 2004231189 A1 | 12/2004 | |
| AU | 2004242527 A1 | 1/2005 | |
| AU | 2001281277 B2 | 9/2005 | |
| AU | 2006308187 A1 | 5/2007 | |
| AU | 2006310681 A1 | 5/2007 | |
| AU | 2002329324 B2 | 7/2007 | |
| AU | 2007294199 A1 | 3/2008 | |
| AU | 2009200985 A1 | 4/2009 | |
| AU | 2006328896 B2 | 8/2013 | |
| CA | 2378589 A1 | 2/2001 | |
| CA | 2381192 A1 | 2/2001 | |
| CA | 2385662 A1 | 3/2001 | |
| CA | 2407987 A1 | 11/2001 | |
| CA | 2418958 A1 | 2/2002 | |
| CA | 2435962 A1 | 8/2002 | |
| CA | 2457755 A1 | 2/2003 | |
| CA | 2436258 A1 | 1/2005 | |
| CA | 2848485 A1 | 1/2005 | |
| CA | 2848490 A1 | 1/2005 | |
| CA | 2595233 A1 | 7/2006 | |
| CA | 2627409 A1 | 5/2007 | |
| CA | 2627555 A1 | 5/2007 | |
| CA | 2634358 A1 | 6/2007 | |
| CA | 2657839 A1 | 3/2008 | |
| CA | 2659690 A1 | 3/2008 | |
| CN | 1338951 A | 3/2002 | |
| CN | 1342443 A | 4/2002 | |
| CN | 1745727 A | 3/2006 | |
| CN | 2762776 Y | 3/2006 | |
| CN | 1897892 A | 1/2007 | |
| CN | 2933337 Y | 8/2007 | |
| CN | 101011298 A | 8/2007 | |
| CN | 101431963 A | 5/2009 | |
| CN | 101605509 A | 12/2009 | |
| CN | 101623217 A | 1/2010 | |
| CN | 101700199 A | 5/2010 | |
| CN | 101720211 A | 6/2010 | |
| CN | 102271626 A | 12/2011 | |
| CN | 102413793 A | 4/2012 | |
| CN | 103118630 A | 5/2013 | |
| DE | 2815756 A1 | 10/1979 | |
| DE | 3920657 A1 | 1/1991 | |
| DE | 3640745 C2 | 3/1992 | |
| DE | 4316971 A1 | 11/1994 | |
| DE | 19532846 A1 | 3/1997 | |
| DE | 19546692 A1 | 6/1997 | |
| DE | 19633901 A1 | 2/1998 | |
| DE | 20003874 U1 | 5/2000 | |
| DE | 19857887 A1 | 7/2000 | |
| DE | 19907646 A1 | 8/2000 | |
| DE | 10010073 A1 | 9/2001 | |
| DE | 10010074 A1 | 10/2001 | |
| DE | 10034105 C1 | 4/2002 | |
| DE | 10049813 C1 | 4/2002 | |
| DE | 10049814 A1 | 4/2002 | |
| DE | 10121210 A1 | 11/2002 | |
| DE | 19546692 C2 | 11/2002 | |
| DE | 10301026 A1 | 2/2004 | |

(56)      References Cited

FOREIGN PATENT DOCUMENTS

| | | | |
|---|---|---|---|
| DE | 10048814 | B4 | 4/2004 |
| DE | 10049812 | B4 | 6/2004 |
| DE | 10302447 | A1 | 7/2004 |
| DE | 10335948 | B3 | 2/2005 |
| DE | 10010074 | B4 | 4/2005 |
| DE | 19857887 | B4 | 5/2005 |
| DE | 10049815 | B4 | 10/2005 |
| DE | 10010073 | B4 | 12/2005 |
| DE | 102005003632 | A1 | 8/2006 |
| DE | 102005051849 | A1 | 5/2007 |
| DE | 102005052628 | A1 | 5/2007 |
| DE | 202007005491 | U1 | 6/2007 |
| DE | 20221871 | U1 | 9/2008 |
| DE | 69937568 | T2 | 9/2008 |
| EP | 0084395 | A1 | 7/1983 |
| EP | 0103546 | B1 | 5/1988 |
| EP | 0144167 | B1 | 11/1989 |
| EP | 0402036 | A1 | 12/1990 |
| EP | 0402176 | A2 | 12/1990 |
| EP | 0411118 | A1 | 2/1991 |
| EP | 0458877 | A1 | 12/1991 |
| EP | 0515324 | A1 | 11/1992 |
| EP | 0547135 | A1 | 6/1993 |
| EP | 0579523 | A1 | 1/1994 |
| EP | 0402176 | B1 | 4/1994 |
| EP | 0592410 | A1 | 4/1994 |
| EP | 0597967 | A4 | 12/1994 |
| EP | 0458877 | B1 | 5/1995 |
| EP | 0657147 | A2 | 6/1995 |
| EP | 0592410 | B1 | 10/1995 |
| EP | 0402036 | B1 | 4/1996 |
| EP | 0729364 | A1 | 9/1996 |
| EP | 0732088 | A2 | 9/1996 |
| EP | 0756498 | A1 | 2/1997 |
| EP | 0409929 | B1 | 4/1997 |
| EP | 0778775 | A1 | 6/1997 |
| EP | 0792624 | A1 | 9/1997 |
| EP | 0797957 | A1 | 10/1997 |
| EP | 0797958 | A1 | 10/1997 |
| EP | 0799604 | A1 | 10/1997 |
| EP | 0801928 | A1 | 10/1997 |
| EP | 0815798 | A2 | 1/1998 |
| EP | 0826346 | A1 | 3/1998 |
| EP | 0829239 | A1 | 3/1998 |
| EP | 0836834 | A2 | 4/1998 |
| EP | 0850607 | A1 | 7/1998 |
| EP | 0853921 | A2 | 7/1998 |
| EP | 0858779 | A1 | 8/1998 |
| EP | 0871414 | A1 | 10/1998 |
| EP | 0876796 | A2 | 11/1998 |
| EP | 0876803 | A2 | 11/1998 |
| EP | 0778775 | B1 | 1/1999 |
| EP | 0888750 | A1 | 1/1999 |
| EP | 0895752 | A1 | 2/1999 |
| EP | 0896813 | A2 | 2/1999 |
| EP | 0903122 | A2 | 3/1999 |
| EP | 0928615 | A1 | 7/1999 |
| EP | 0657147 | B1 | 8/1999 |
| EP | 0934728 | A2 | 8/1999 |
| EP | 0938877 | A2 | 9/1999 |
| EP | 0597967 | B1 | 12/1999 |
| EP | 0696447 | B1 | 1/2000 |
| EP | 0971649 | A1 | 1/2000 |
| EP | 0986348 | A1 | 3/2000 |
| EP | 1020166 | A1 | 7/2000 |
| EP | 1027870 | A1 | 8/2000 |
| EP | 1041942 | A1 | 10/2000 |
| EP | 1041943 | A1 | 10/2000 |
| EP | 1057459 | A1 | 12/2000 |
| EP | 1057460 | A1 | 12/2000 |
| EP | 1089676 | A2 | 4/2001 |
| EP | 1097676 | A1 | 5/2001 |
| EP | 1112042 | A1 | 7/2001 |
| EP | 1117446 | A1 | 7/2001 |
| EP | 1158937 | A1 | 12/2001 |
| EP | 0547135 | B1 | 1/2002 |
| EP | 0729364 | B1 | 1/2002 |
| EP | 1164976 | A1 | 1/2002 |
| EP | 1166721 | A2 | 1/2002 |
| EP | 1171061 | A1 | 1/2002 |
| EP | 1206179 | A1 | 5/2002 |
| EP | 0756498 | B1 | 7/2002 |
| EP | 1233731 | A1 | 8/2002 |
| EP | 0986348 | B1 | 9/2002 |
| EP | 1235537 | A1 | 9/2002 |
| EP | 1248655 | A1 | 10/2002 |
| EP | 1251804 | A1 | 10/2002 |
| EP | 1251805 | A2 | 10/2002 |
| EP | 1257305 | A1 | 11/2002 |
| EP | 1259195 | A1 | 11/2002 |
| EP | 0959815 | B1 | 12/2002 |
| EP | 0971649 | B1 | 12/2002 |
| EP | 1262201 | A1 | 12/2002 |
| EP | 1264582 | A2 | 12/2002 |
| EP | 1281357 | A2 | 2/2003 |
| EP | 1281375 | A2 | 2/2003 |
| EP | 0888142 | B1 | 5/2003 |
| EP | 1112097 | B1 | 6/2003 |
| EP | 0937439 | B1 | 9/2003 |
| EP | 1017868 | B1 | 9/2003 |
| EP | 1354569 | A1 | 10/2003 |
| EP | 1340473 | A3 | 2/2004 |
| EP | 1041943 | B1 | 3/2004 |
| EP | 1356793 | A3 | 3/2004 |
| EP | 0871414 | B1 | 4/2004 |
| EP | 1042045 | B1 | 5/2004 |
| EP | 1414295 | A2 | 5/2004 |
| EP | 0819013 | B1 | 6/2004 |
| EP | 1430853 | A2 | 6/2004 |
| EP | 1347785 | B1 | 7/2004 |
| EP | 1435879 | A1 | 7/2004 |
| EP | 1439800 | A2 | 7/2004 |
| EP | 0954248 | B1 | 9/2004 |
| EP | 1452153 | A1 | 9/2004 |
| EP | 0987998 | B1 | 10/2004 |
| EP | 1206179 | B1 | 10/2004 |
| EP | 1469797 | A1 | 10/2004 |
| EP | 1087727 | B1 | 11/2004 |
| EP | 1115452 | B1 | 11/2004 |
| EP | 1117446 | B1 | 11/2004 |
| EP | 1472996 | A1 | 11/2004 |
| EP | 1477202 | A2 | 11/2004 |
| EP | 1107710 | B1 | 12/2004 |
| EP | 1233731 | B1 | 12/2004 |
| EP | 1484081 | A1 | 12/2004 |
| EP | 1494616 | A2 | 1/2005 |
| EP | 1499366 | A1 | 1/2005 |
| EP | 1143879 | B1 | 3/2005 |
| EP | 1516599 | A2 | 3/2005 |
| EP | 1518518 | A2 | 3/2005 |
| EP | 1229864 | B1 | 4/2005 |
| EP | 1253875 | B1 | 4/2005 |
| EP | 1521414 | A1 | 4/2005 |
| EP | 1522278 | A2 | 4/2005 |
| EP | 1088529 | B1 | 6/2005 |
| EP | 1093771 | B1 | 6/2005 |
| EP | 1251803 | B1 | 6/2005 |
| EP | 1547533 | A2 | 6/2005 |
| EP | 1059894 | B1 | 7/2005 |
| EP | 1551336 | A1 | 7/2005 |
| EP | 1000590 | B1 | 8/2005 |
| EP | 1027013 | B1 | 8/2005 |
| EP | 1078610 | B1 | 8/2005 |
| EP | 1560542 | A1 | 8/2005 |
| EP | 1562515 | A1 | 8/2005 |
| EP | 1570809 | A1 | 9/2005 |
| EP | 1576937 | A2 | 9/2005 |
| EP | 0943302 | B1 | 10/2005 |
| EP | 1267753 | B1 | 10/2005 |
| EP | 1582178 | A2 | 10/2005 |
| EP | 1582179 | A2 | 10/2005 |
| EP | 1011523 | B1 | 11/2005 |
| EP | 1067869 | B1 | 11/2005 |
| EP | 1469797 | B1 | 11/2005 |

(56) References Cited

FOREIGN PATENT DOCUMENTS

| | | | |
|---|---|---|---|
| EP | 1589902 | A1 | 11/2005 |
| EP | 1598031 | A2 | 11/2005 |
| EP | 1600110 | A1 | 11/2005 |
| EP | 0786970 | B1 | 12/2005 |
| EP | 1156757 | B1 | 12/2005 |
| EP | 1021141 | B1 | 1/2006 |
| EP | 1614400 | A2 | 1/2006 |
| EP | 1616536 | A2 | 1/2006 |
| EP | 1041942 | B1 | 6/2006 |
| EP | 1663070 | A2 | 6/2006 |
| EP | 1690515 | A1 | 8/2006 |
| EP | 1051204 | B1 | 12/2006 |
| EP | 1395208 | B1 | 1/2007 |
| EP | 1251805 | B1 | 3/2007 |
| EP | 1255510 | B1 | 4/2007 |
| EP | 1499366 | B1 | 7/2007 |
| EP | 1600121 | B1 | 7/2007 |
| EP | 1112042 | B1 | 11/2007 |
| EP | 1251797 | B1 | 11/2007 |
| EP | 1616531 | B1 | 12/2007 |
| EP | 1878407 | A1 | 1/2008 |
| EP | 1886649 | A2 | 2/2008 |
| EP | 1406561 | A4 | 3/2008 |
| EP | 1900343 | A2 | 3/2008 |
| EP | 1435878 | B1 | 4/2008 |
| EP | 1886649 | A3 | 4/2008 |
| EP | 1251804 | B1 | 7/2008 |
| EP | 1605871 | B1 | 7/2008 |
| EP | 1259195 | B1 | 10/2008 |
| EP | 1980220 | A1 | 10/2008 |
| EP | 1994913 | A2 | 11/2008 |
| EP | 1994913 | A3 | 12/2008 |
| EP | 2000115 | A2 | 12/2008 |
| EP | 1408882 | B1 | 2/2009 |
| EP | 1255510 | B3 | 3/2009 |
| EP | 1330213 | B1 | 3/2009 |
| EP | 2033593 | A1 | 3/2009 |
| EP | 2074964 | A1 | 7/2009 |
| EP | 1401359 | B1 | 8/2009 |
| EP | 1968491 | B1 | 7/2010 |
| EP | 1259193 | B1 | 11/2010 |
| EP | 2257242 | A1 | 12/2010 |
| EP | 2266503 | A2 | 12/2010 |
| EP | 2266504 | A2 | 12/2010 |
| EP | 1893132 | B1 | 3/2011 |
| EP | 2059192 | B1 | 7/2011 |
| EP | 1441672 | B1 | 9/2011 |
| EP | 2364669 | A2 | 9/2011 |
| EP | 2387977 | A1 | 11/2011 |
| EP | 1603493 | B1 | 12/2011 |
| EP | 1281375 | B1 | 2/2012 |
| EP | 2047824 | B1 | 5/2012 |
| EP | 2474287 | A1 | 7/2012 |
| EP | 2387977 | B1 | 11/2013 |
| EP | 1551274 | B1 | 12/2014 |
| EP | 2874812 | A1 | 5/2015 |
| EP | 2749254 | B1 | 6/2015 |
| EP | 1702247 | B1 | 8/2015 |
| EP | 2926766 | A1 | 10/2015 |
| EP | 1519697 | B1 | 11/2015 |
| EP | 1863545 | B1 | 11/2015 |
| EP | 1835948 | B1 | 2/2016 |
| EP | 1734902 | B1 | 6/2016 |
| EP | 3028668 | A1 | 6/2016 |
| EP | 1539047 | B1 | 11/2016 |
| EP | 3181096 | A1 | 6/2017 |
| EP | 2659861 | B1 | 3/2019 |
| EP | 1667614 | B2 | 4/2020 |
| EP | 3270825 | B1 | 4/2020 |
| EP | 3730094 | A1 | 10/2020 |
| EP | 3730094 | B1 | 4/2024 |
| EP | 4175594 | B1 | 5/2024 |
| FR | 2788217 | A1 | 7/2000 |
| FR | 2815844 | A1 | 5/2002 |
| FR | 2828263 | A1 | 2/2003 |
| GB | 2398245 | B | 3/2007 |
| GB | 2433700 | A | 7/2007 |
| GB | 2440809 | A | 2/2008 |
| JP | S5286296 | A | 7/1977 |
| JP | S54137896 | A | 9/1979 |
| JP | S62227352 | A | 10/1987 |
| JP | S6449571 | A | 2/1989 |
| JP | H0447576 | B2 | 8/1992 |
| JP | H04505866 | A | 10/1992 |
| JP | H06505187 | A | 6/1994 |
| JP | H06343703 | A | 12/1994 |
| JP | H07504091 | A | 5/1995 |
| JP | H07505803 | A | 6/1995 |
| JP | H07265339 | A | 10/1995 |
| JP | H0833715 | A | 2/1996 |
| JP | H1049571 | A | 2/1998 |
| JP | H10507673 | A | 7/1998 |
| JP | 2001000460 | A | 1/2001 |
| JP | 2001504016 | A | 3/2001 |
| JP | 2001526574 | A | 12/2001 |
| JP | 2002525168 | A | 8/2002 |
| JP | 2002525169 | A | 8/2002 |
| JP | 2002536115 | A | 10/2002 |
| JP | 2003515386 | A | 5/2003 |
| JP | 2003518984 | A | 6/2003 |
| JP | 2003523262 | A | 8/2003 |
| JP | 2003524504 | A | 8/2003 |
| JP | 2004504111 | A | 2/2004 |
| JP | 2004130068 | A | 4/2004 |
| JP | 2004514467 | A | 5/2004 |
| JP | 2004255186 | A | 9/2004 |
| JP | 2004267750 | A | 9/2004 |
| JP | 2004283461 | A | 10/2004 |
| JP | 2005505343 | A | 2/2005 |
| JP | 2005118585 | A | 5/2005 |
| JP | 2007521125 | A | 8/2007 |
| JP | 2007296375 | A | 11/2007 |
| JP | 2007298375 | A | 11/2007 |
| JP | 2007534381 | A | 11/2007 |
| JP | 2007536003 | A | 12/2007 |
| JP | 2008506497 | A | 3/2008 |
| JP | 2008514345 | A | 5/2008 |
| JP | 2008535572 | A | 9/2008 |
| JP | 2008539985 | A | 11/2008 |
| JP | 2008541865 | A | 11/2008 |
| JP | 2009034529 | A | 2/2009 |
| JP | 2009061293 | A | 3/2009 |
| JP | 2009509635 | A | 3/2009 |
| JP | 4246433 | B2 | 4/2009 |
| JP | 2009520535 | A | 5/2009 |
| JP | 2009131397 | A | 6/2009 |
| JP | 4295460 | B2 | 7/2009 |
| JP | 2009528905 | A | 8/2009 |
| JP | 2009534157 | A | 9/2009 |
| JP | 2010525896 | A | 7/2010 |
| JP | 2010526609 | A | 8/2010 |
| JP | 4636794 | B2 | 2/2011 |
| JP | 2011509805 | A | 3/2011 |
| JP | 4739223 | B2 | 8/2011 |
| JP | 2012500665 | A | 1/2012 |
| JP | 4904362 | B2 | 3/2012 |
| JP | 4912395 | B2 | 4/2012 |
| JP | 2012518446 | A | 8/2012 |
| JP | 2013520260 | A | 6/2013 |
| JP | 2013521884 | A | 6/2013 |
| JP | 2013526388 | A | 6/2013 |
| JP | 5341455 | B2 | 11/2013 |
| JP | 2013540495 | A | 11/2013 |
| JP | 6144009 | B2 | 6/2017 |
| JP | 6449571 | B2 | 1/2019 |
| WO | WO-8402266 | A1 | 6/1984 |
| WO | WO-9009102 | A1 | 8/1990 |
| WO | WO-9014804 | A1 | 12/1990 |
| WO | WO-9117720 | A1 | 11/1991 |
| WO | WO-9203990 | A1 | 3/1992 |
| WO | WO-9212690 | A1 | 8/1992 |
| WO | WO-9214419 | A1 | 9/1992 |
| WO | WO-9217118 | A1 | 10/1992 |
| WO | WO-9301768 | A1 | 2/1993 |

(56) References Cited

FOREIGN PATENT DOCUMENTS

| | | |
|---|---|---|
| WO | WO-9315693 A1 | 8/1993 |
| WO | WO-9320757 A2 | 10/1993 |
| WO | WO-9504556 A2 | 2/1995 |
| WO | WO-9511055 A1 | 4/1995 |
| WO | WO-9524873 A1 | 9/1995 |
| WO | WO-9528183 A1 | 10/1995 |
| WO | WO-9528899 A1 | 11/1995 |
| WO | WO-9529640 A1 | 11/1995 |
| WO | WO-9529713 A1 | 11/1995 |
| WO | WO-9613227 A1 | 5/1996 |
| WO | WO-9614032 A1 | 5/1996 |
| WO | WO-9624306 A1 | 8/1996 |
| WO | WO-9630072 A1 | 10/1996 |
| WO | WO-9632972 A1 | 10/1996 |
| WO | WO-9635469 A1 | 11/1996 |
| WO | WO-9639962 A1 | 12/1996 |
| WO | WO-9639964 A1 | 12/1996 |
| WO | WO-9639965 A1 | 12/1996 |
| WO | WO-9640012 A1 | 12/1996 |
| WO | WO-9713463 A1 | 4/1997 |
| WO | WO-9713471 A1 | 4/1997 |
| WO | WO-9724082 A1 | 7/1997 |
| WO | WO-9727893 A1 | 8/1997 |
| WO | WO-9727897 A1 | 8/1997 |
| WO | WO-9727898 A1 | 8/1997 |
| WO | WO-9732551 A1 | 9/1997 |
| WO | WO-9732615 A1 | 9/1997 |
| WO | WO-9743961 A1 | 11/1997 |
| WO | WO-9748350 A1 | 12/1997 |
| WO | WO-9803118 A1 | 1/1998 |
| WO | WO-9806356 A1 | 2/1998 |
| WO | WO-9808456 A1 | 3/1998 |
| WO | WO-9810714 A1 | 3/1998 |
| WO | WO-9811846 A1 | 3/1998 |
| WO | WO-9814137 A1 | 4/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9829057 A1 | 7/1998 |
| WO | WO-9836790 A1 | 8/1998 |
| WO | WO-9838916 A1 | 9/1998 |
| WO | WO-9838925 A1 | 9/1998 |
| WO | WO-9838939 A1 | 9/1998 |
| WO | WO-9838941 A1 | 9/1998 |
| WO | WO-9839038 A1 | 9/1998 |
| WO | WO-9843556 A1 | 10/1998 |
| WO | WO-9844869 A1 | 10/1998 |
| WO | WO-9846115 A2 | 10/1998 |
| WO | WO-9846119 A1 | 10/1998 |
| WO | WO-9846165 A1 | 10/1998 |
| WO | WO-9849964 A1 | 11/1998 |
| WO | WO-9850103 A1 | 11/1998 |
| WO | WO-9853759 A2 | 12/1998 |
| WO | WO-9853761 A1 | 12/1998 |
| WO | WO-9855027 A2 | 12/1998 |
| WO | WO-9855047 A1 | 12/1998 |
| WO | WO-9857590 A1 | 12/1998 |
| WO | WO-9857591 A1 | 12/1998 |
| WO | WO-9857592 A1 | 12/1998 |
| WO | WO-9857599 A2 | 12/1998 |
| WO | WO-9907296 A1 | 2/1999 |
| WO | WO-9908624 A1 | 2/1999 |
| WO | WO-9915112 A1 | 4/1999 |
| WO | WO-9915220 A1 | 4/1999 |
| WO | WO-9917671 A1 | 4/1999 |
| WO | WO-9917683 A1 | 4/1999 |
| WO | WO-9921490 A1 | 5/1999 |
| WO | WO-9921510 A1 | 5/1999 |
| WO | WO-9922655 A1 | 5/1999 |
| WO | WO-9922656 A1 | 5/1999 |
| WO | WO-9922658 A1 | 5/1999 |
| WO | WO-9925273 A1 | 5/1999 |
| WO | WO-9927985 A1 | 6/1999 |
| WO | WO-9933414 A1 | 7/1999 |
| WO | WO-9935977 A1 | 7/1999 |
| WO | WO-9935979 A1 | 7/1999 |
| WO | WO-9935980 A1 | 7/1999 |
| WO | WO-9936000 A1 | 7/1999 |
| WO | WO-9936001 A1 | 7/1999 |
| WO | WO-9937337 A2 | 7/1999 |
| WO | WO-9938459 A2 | 8/1999 |
| WO | WO-9940853 A1 | 8/1999 |
| WO | WO-9940868 A1 | 8/1999 |
| WO | WO-9940963 A1 | 8/1999 |
| WO | WO-9940964 A1 | 8/1999 |
| WO | WO-9942058 A1 | 8/1999 |
| WO | WO-9944524 A2 | 9/1999 |
| WO | WO-9944540 A2 | 9/1999 |
| WO | WO-9944542 A2 | 9/1999 |
| WO | WO-9947071 A1 | 9/1999 |
| WO | WO-9947075 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |
| WO | WO-9951165 A1 | 10/1999 |
| WO | WO-9953863 A1 | 10/1999 |
| WO | WO-9953987 A1 | 10/1999 |
| WO | WO-9955406 A1 | 11/1999 |
| WO | WO-9960941 A1 | 12/1999 |
| WO | WO-9962430 A1 | 12/1999 |
| WO | WO-9966863 A2 | 12/1999 |
| WO | WO-0002503 A1 | 1/2000 |
| WO | WO-0009059 A2 | 2/2000 |
| WO | WO-0009195 A1 | 2/2000 |
| WO | WO-0010623 A1 | 3/2000 |
| WO | WO-0012029 A1 | 3/2000 |
| WO | WO-0013722 A1 | 3/2000 |
| WO | WO-0015146 A1 | 3/2000 |
| WO | WO-0015147 A1 | 3/2000 |
| WO | WO-0015148 A1 | 3/2000 |
| WO | WO-0015149 A1 | 3/2000 |
| WO | WO-0015275 A2 | 3/2000 |
| WO | WO-0016848 A1 | 3/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018445 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO-0024449 A1 | 5/2000 |
| WO | WO-0025702 A1 | 5/2000 |
| WO | WO-0028922 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0041652 A1 | 7/2000 |
| WO | WO-0043051 A1 | 7/2000 |
| WO | WO-0044211 A1 | 7/2000 |
| WO | WO-0044308 A2 | 8/2000 |
| WO | WO-0044311 A2 | 8/2000 |
| WO | WO-0044313 A1 | 8/2000 |
| WO | WO-0044331 A1 | 8/2000 |
| WO | WO-0045711 A1 | 8/2000 |
| WO | WO-0045874 A1 | 8/2000 |
| WO | WO-0045886 A2 | 8/2000 |
| WO | WO-0047136 A1 | 8/2000 |
| WO | WO-0047139 A1 | 8/2000 |
| WO | WO-0048531 A1 | 8/2000 |
| WO | WO-0049952 A1 | 8/2000 |
| WO | WO-0049954 A2 | 8/2000 |

(56)　　　　References Cited

FOREIGN PATENT DOCUMENTS

| | | | |
|---|---|---|---|
| WO | WO-0049956 | A1 | 8/2000 |
| WO | WO-0049970 | A1 | 8/2000 |
| WO | WO-0053122 | A1 | 9/2000 |
| WO | WO-0053125 | A1 | 9/2000 |
| WO | WO-0054660 | A1 | 9/2000 |
| WO | WO-0054661 | A1 | 9/2000 |
| WO | WO-0056224 | A1 | 9/2000 |
| WO | WO-0056225 | A1 | 9/2000 |
| WO | WO-0056387 | A1 | 9/2000 |
| WO | WO-0060995 | A2 | 10/2000 |
| WO | WO-0062714 | A1 | 10/2000 |
| WO | WO-0066007 | A1 | 11/2000 |
| WO | WO-0066009 | A1 | 11/2000 |
| WO | WO-0066035 | A1 | 11/2000 |
| WO | WO-0067661 | A2 | 11/2000 |
| WO | WO-0069345 | A1 | 11/2000 |
| WO | WO-0069367 | A1 | 11/2000 |
| WO | WO-0069504 | A1 | 11/2000 |
| WO | WO-0071195 | A1 | 11/2000 |
| WO | WO-0078226 | A1 | 12/2000 |
| WO | WO-0105331 | A1 | 1/2001 |
| WO | WO-0106959 | A1 | 2/2001 |
| WO | WO-0108566 | A1 | 2/2001 |
| WO | WO-0108596 | A1 | 2/2001 |
| WO | WO-0108602 | A1 | 2/2001 |
| WO | WO-0110209 | A1 | 2/2001 |
| WO | WO-0110320 | A1 | 2/2001 |
| WO | WO-0110340 | A1 | 2/2001 |
| WO | WO-0110341 | A2 | 2/2001 |
| WO | WO-0110343 | A1 | 2/2001 |
| WO | WO-0110347 | A1 | 2/2001 |
| WO | WO-0110348 | A1 | 2/2001 |
| WO | WO-0110349 | A1 | 2/2001 |
| WO | WO-0110350 | A1 | 2/2001 |
| WO | WO-0117440 | A1 | 3/2001 |
| WO | WO-0117456 | A1 | 3/2001 |
| WO | WO-0135864 | A1 | 5/2001 |
| WO | WO-0135870 | A1 | 5/2001 |
| WO | WO-0136870 | A1 | 5/2001 |
| WO | WO-0139700 | A1 | 6/2001 |
| WO | WO-0141679 | A1 | 6/2001 |
| WO | WO-0149185 | A1 | 7/2001 |
| WO | WO-0149187 | A1 | 7/2001 |
| WO | WO-0149213 | A2 | 7/2001 |
| WO | WO-0151104 | A1 | 7/2001 |
| WO | WO-0154625 | A1 | 8/2001 |
| WO | WO-0158503 | A1 | 8/2001 |
| WO | WO-0162189 | A1 | 8/2001 |
| WO | WO-0047139 | A9 | 9/2001 |
| WO | WO-0164137 | A1 | 9/2001 |
| WO | WO-0176510 | A2 | 10/2001 |
| WO | WO-0182837 | A2 | 11/2001 |
| WO | WO-0197715 | A1 | 12/2001 |
| WO | WO-0211647 | A2 | 2/2002 |
| WO | WO-0219926 | A1 | 3/2002 |
| WO | WO-0222054 | A1 | 3/2002 |
| WO | WO-0224118 | A1 | 3/2002 |
| WO | WO-0236048 | A1 | 5/2002 |
| WO | WO-0241789 | A2 | 5/2002 |
| WO | WO-0243620 | A1 | 6/2002 |
| WO | WO-0247575 | A2 | 6/2002 |
| WO | WO-0249540 | A2 | 6/2002 |
| WO | WO-02051489 | A2 | 7/2002 |
| WO | WO-02056798 | A2 | 7/2002 |
| WO | WO-02056955 | A1 | 7/2002 |
| WO | WO-02058745 | A1 | 8/2002 |
| WO | WO-02060509 | A1 | 8/2002 |
| WO | WO-02067782 | A2 | 9/2002 |
| WO | WO-02069842 | A2 | 9/2002 |
| WO | WO-02076349 | A1 | 10/2002 |
| WO | WO-02100297 | A2 | 12/2002 |
| WO | WO-02100301 | A1 | 12/2002 |
| WO | WO-02102286 | A1 | 12/2002 |
| WO | WO-03003943 | A2 | 1/2003 |
| WO | WO-03003949 | A2 | 1/2003 |
| WO | WO-03007795 | A2 | 1/2003 |
| WO | WO-03009785 | A1 | 2/2003 |
| WO | WO-03011195 | A2 | 2/2003 |
| WO | WO-03013239 | A2 | 2/2003 |
| WO | WO-03015851 | A1 | 2/2003 |
| WO | WO-03022183 | A1 | 3/2003 |
| WO | WO-03028592 | A1 | 4/2003 |
| WO | WO-03030776 | A2 | 4/2003 |
| WO | WO-03032869 | A1 | 4/2003 |
| WO | WO-03032870 | A1 | 4/2003 |
| WO | WO-03037222 | A2 | 5/2003 |
| WO | WO-03037227 | A2 | 5/2003 |
| WO | WO-03047460 | A2 | 6/2003 |
| WO | WO-03047468 | A1 | 6/2003 |
| WO | WO-03047648 | A2 | 6/2003 |
| WO | WO-03051231 | A2 | 6/2003 |
| WO | WO-03063729 | A2 | 8/2003 |
| WO | WO-03079928 | A2 | 10/2003 |
| WO | WO-03079932 | A2 | 10/2003 |
| WO | WO-03079933 | A1 | 10/2003 |
| WO | WO-03088873 | A1 | 10/2003 |
| WO | WO-03092554 | A1 | 11/2003 |
| WO | WO-03094793 | A1 | 11/2003 |
| WO | WO-03094797 | A1 | 11/2003 |
| WO | WO-03096932 | A1 | 11/2003 |
| WO | WO-03096935 | A1 | 11/2003 |
| WO | WO-03101195 | A1 | 12/2003 |
| WO | WO-03103949 | A1 | 12/2003 |
| WO | WO-03003949 | A3 | 1/2004 |
| WO | WO-2004004597 | A2 | 1/2004 |
| WO | WO-2004006803 | A1 | 1/2004 |
| WO | WO-2004006804 | A1 | 1/2004 |
| WO | WO-2004014256 | A1 | 2/2004 |
| WO | WO-2004016200 | A1 | 2/2004 |
| WO | WO-2004016201 | A2 | 2/2004 |
| WO | WO-2004019811 | A2 | 3/2004 |
| WO | WO-2004019817 | A1 | 3/2004 |
| WO | WO-2004019825 | A1 | 3/2004 |
| WO | WO-2004021922 | A2 | 3/2004 |
| WO | WO-2004023980 | A2 | 3/2004 |
| WO | WO-2004026117 | A2 | 4/2004 |
| WO | WO-2004026173 | A2 | 4/2004 |
| WO | WO-2004028399 | A2 | 4/2004 |
| WO | WO-2004030515 | A2 | 4/2004 |
| WO | WO-2004041126 | A1 | 5/2004 |
| WO | WO-2004043293 | A2 | 5/2004 |
| WO | WO-2004043301 | A1 | 5/2004 |
| WO | WO-2004047681 | A1 | 6/2004 |
| WO | WO-2004058106 | A2 | 7/2004 |
| WO | WO-2004062980 | A1 | 7/2004 |
| WO | WO-2004064671 | A2 | 8/2004 |
| WO | WO-2004066876 | A1 | 8/2004 |
| WO | WO-2004071352 | A1 | 8/2004 |
| WO | WO-2004082527 | A2 | 9/2004 |
| WO | WO-2004082528 | A2 | 9/2004 |
| WO | WO-2004082536 | A1 | 9/2004 |
| WO | WO-2004089250 | A1 | 10/2004 |
| WO | WO-2004089253 | A1 | 10/2004 |
| WO | WO-2004093728 | A2 | 11/2004 |
| WO | WO-2004096100 | A1 | 11/2004 |
| WO | WO-2004103162 | A2 | 12/2004 |
| WO | WO-2004105651 | A1 | 12/2004 |
| WO | WO-2005002466 | A2 | 1/2005 |
| WO | WO-2005004753 | A1 | 1/2005 |
| WO | WO-2005007343 | A1 | 1/2005 |
| WO | WO-2005009285 | A2 | 2/2005 |
| WO | WO-2005011534 | A1 | 2/2005 |
| WO | WO-2005011535 | A2 | 2/2005 |
| WO | WO-2005021063 | A2 | 3/2005 |
| WO | WO-2005023155 | A1 | 3/2005 |
| WO | WO-2005027790 | A1 | 3/2005 |
| WO | WO-2005027797 | A2 | 3/2005 |
| WO | WO-2005032622 | A2 | 4/2005 |
| WO | WO-2005034812 | A1 | 4/2005 |
| WO | WO-2005010215 | A3 | 5/2005 |
| WO | WO-2005046528 | A1 | 5/2005 |
| WO | WO-2005046529 | A1 | 5/2005 |
| WO | WO-2005048883 | A1 | 6/2005 |
| WO | WO-2005062980 | A2 | 7/2005 |

(56) References Cited

FOREIGN PATENT DOCUMENTS

| | | |
|---|---|---|
| WO | WO-2005063980 A1 | 7/2005 |
| WO | WO-2005065585 A1 | 7/2005 |
| WO | WO-2005065594 A1 | 7/2005 |
| WO | WO-2005070343 A1 | 8/2005 |
| WO | WO-2005072654 A1 | 8/2005 |
| WO | WO-2005076890 A2 | 8/2005 |
| WO | WO-2005084595 A1 | 9/2005 |
| WO | WO-2005087140 A1 | 9/2005 |
| WO | WO-2005096993 A1 | 10/2005 |
| WO | WO-2005102015 A2 | 11/2005 |
| WO | WO-2005110240 A1 | 11/2005 |
| WO | WO-2005112779 A1 | 12/2005 |
| WO | WO-2006005015 A2 | 1/2006 |
| WO | WO-2006009690 A1 | 1/2006 |
| WO | WO-2006026371 A1 | 3/2006 |
| WO | WO-2006027499 A2 | 3/2006 |
| WO | WO-2005062980 A3 | 5/2006 |
| WO | WO-2006058163 A2 | 6/2006 |
| WO | WO-2006065949 A2 | 6/2006 |
| WO | WO-2006066327 A1 | 6/2006 |
| WO | WO-2006068944 A2 | 6/2006 |
| WO | WO-2006070372 A2 | 7/2006 |
| WO | WO-2006076890 A1 | 7/2006 |
| WO | WO-2006083763 A1 | 8/2006 |
| WO | WO-2006086135 A2 | 8/2006 |
| WO | WO-2006086736 A2 | 8/2006 |
| WO | WO-2006089517 A1 | 8/2006 |
| WO | WO-2006093795 A1 | 9/2006 |
| WO | WO-2006102063 A2 | 9/2006 |
| WO | WO-2006108090 A2 | 10/2006 |
| WO | WO-2006118766 A1 | 11/2006 |
| WO | WO-2006124649 A2 | 11/2006 |
| WO | WO-2006127756 A2 | 11/2006 |
| WO | WO-2006127765 A1 | 11/2006 |
| WO | WO-2006129441 A1 | 12/2006 |
| WO | WO-2006132948 A1 | 12/2006 |
| WO | WO-2006133959 A1 | 12/2006 |
| WO | WO-2006138173 A2 | 12/2006 |
| WO | WO-2006138391 A2 | 12/2006 |
| WO | WO-2007009117 A1 | 1/2007 |
| WO | WO-2007009609 A1 | 1/2007 |
| WO | WO-2007013999 A2 | 2/2007 |
| WO | WO-2007033093 A2 | 3/2007 |
| WO | WO-2007035471 A2 | 3/2007 |
| WO | WO-2005102015 A3 | 4/2007 |
| WO | WO-2007044285 A2 | 4/2007 |
| WO | WO-2007047488 A2 | 4/2007 |
| WO | WO-2007047945 A2 | 4/2007 |
| WO | WO-2007048529 A1 | 5/2007 |
| WO | WO-2007051620 A1 | 5/2007 |
| WO | WO-2007053243 A2 | 5/2007 |
| WO | WO-2007058847 A2 | 5/2007 |
| WO | WO-2007059252 A1 | 5/2007 |
| WO | WO-2006086736 A3 | 6/2007 |
| WO | WO-2007071436 A2 | 6/2007 |
| WO | WO-2007092354 A2 | 8/2007 |
| WO | WO-2007097983 A2 | 8/2007 |
| WO | WO-2007098232 A2 | 8/2007 |
| WO | WO-2007120543 A1 | 10/2007 |
| WO | WO-2007123658 A1 | 11/2007 |
| WO | WO-2007123956 A2 | 11/2007 |
| WO | WO-2007071436 B1 | 1/2008 |
| WO | WO-2008028569 A1 | 3/2008 |
| WO | WO-2008031103 A2 | 3/2008 |
| WO | WO-2008035337 A2 | 3/2008 |
| WO | WO-2008040555 A2 | 4/2008 |
| WO | WO-2008045949 A2 | 4/2008 |
| WO | WO-2008047354 A2 | 4/2008 |
| WO | WO-2008051554 A2 | 5/2008 |
| WO | WO-2008070442 A1 | 6/2008 |
| WO | WO-2008070797 A2 | 6/2008 |
| WO | WO-2008079962 A1 | 7/2008 |
| WO | WO-2008098191 A2 | 8/2008 |
| WO | WO-2008100599 A1 | 8/2008 |
| WO | WO-2008101083 A2 | 8/2008 |
| WO | WO-2008118481 A2 | 10/2008 |
| WO | WO-2008125153 A1 | 10/2008 |
| WO | WO-2008137603 A2 | 11/2008 |
| WO | WO-2008138584 A1 | 11/2008 |
| WO | WO-2008150529 A1 | 12/2008 |
| WO | WO-2009002548 A1 | 12/2008 |
| WO | WO-2009024859 A2 | 2/2009 |
| WO | WO-2009029199 A1 | 3/2009 |
| WO | WO-2009042196 A2 | 4/2009 |
| WO | WO-2009045334 A1 | 4/2009 |
| WO | WO-2009045338 A1 | 4/2009 |
| WO | WO-2009053497 A1 | 4/2009 |
| WO | WO-2009054397 A1 | 4/2009 |
| WO | WO-2009061389 A2 | 5/2009 |
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO-2009137712 A1 | 11/2009 |
| WO | WO-2009149462 A2 | 12/2009 |
| WO | WO-2009155561 A2 | 12/2009 |
| WO | WO-2010022138 A2 | 2/2010 |
| WO | WO-2010042950 A2 | 4/2010 |
| WO | WO-2010043950 A2 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010141626 A2 | 12/2010 |
| WO | WO-2011008812 A2 | 1/2011 |
| WO | WO-2011035327 A1 | 3/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011102970 A1 | 8/2011 |
| WO | WO-2011104269 A1 | 9/2011 |
| WO | WO-2011120050 A1 | 9/2011 |
| WO | WO-2011126749 A1 | 10/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A2 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |
| WO | WO-2013134214 A1 | 9/2013 |
| WO | WO-2014056644 A1 | 4/2014 |
| WO | WO-2014072439 A1 | 5/2014 |
| WO | WO-2014143126 A1 | 9/2014 |
| WO | WO-2014144937 A2 | 9/2014 |
| WO | WO-2015006139 A1 | 1/2015 |
| WO | WO-2015028209 A1 | 3/2015 |
| WO | WO-2015063118 A1 * | 5/2015 | ........... A61F 2/2436 |
| WO | WO-2016093877 A1 | 6/2016 |
| WO | WO-2016126511 A2 | 8/2016 |
| WO | WO-2016150806 A1 | 9/2016 |
| WO | WO-2016177562 A1 | 11/2016 |
| WO | WO-2021242607 A1 | 12/2021 |

(56) References Cited

FOREIGN PATENT DOCUMENTS

| WO | WO-2022144741 A1 | 7/2022 |
| WO | WO-2023156879 A1 | 8/2023 |

OTHER PUBLICATIONS

US 8,062,356 B2, 11/2011, Salahieh et al. (withdrawn)

US 8,062,357 B2, 11/2011, Salahieh et al. (withdrawn)

US 8,075,614 B2, 12/2011, Salahieh et al. (withdrawn)

US 8,133,271 B2, 03/2012, Salahieh et al. (withdrawn)

US 8,211,170 B2, 07/2012, Paul et al. (withdrawn)

Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).

Allen et al., "What are the characteristics of the ideal endovascular graft for abdominal aortic aneurysm exclusion?", J. Endovasc. Surg., vol. 4(2), May 1997, pp. 195-202.

Anabtawi I.N., et al., "Experimental evaluation of myocardial tunnelization as a method of myocardial revascularization," Journal of Thoracic and Cardiovascular Surgery, 58(5):638-646 (Nov. 1969).

Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.

"Aortenklappenbioprothese erfolgreich in der Entwicklung," May 16, 2003, 1 page (with English Translation).

Archie J.P., et al., "Intramyocardial Pressure: Effect of Preload on Transmural Distribution of Systolic Coronary Blood Flow," The American Journal of Cardiology, 35(6):904-911 (Jun. 1975).

Baba H., et al., "Hemodynamic effects of venous valves in aorta-coronary bypass grafts," The Journal of Thoracic and Cardiovascular Surgery, 71(5):774-778 (May 1976).

Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.

Bailey S.R., "Percutaneous Expandable Prosthetic Valves," Textbook of Interventional Cardiology, Second Edition, W.B. Saunders Company, 1994, vol. 2, pp. 1268-1276.

Block P.C., et al., "Percutaneous Approaches to Valvular Heart Disease," Current Cardiology Reports, Mar. 2005, vol. 7(2), pp. 108-113.

Blum et al., "Endoluminal Stent—Grafts for Intrarenal Abdominal Aortic Aneurysms." New Engl. J. Med., 336:13-20 (Jan. 1997).

Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.

Bonhoeffer P., et al., "Percutaneous Insertion of the Pulmonary Valve," Journal of the American College of Cardiology, May 15, 2002, vol. 39, pp. 1664-1669.

Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.

Bonhoeffer P., et al., "Technique and Results of Percutaneous Mitral Valvuloplasty With the Multi-Track System," Journal of Interventional Cadiology, 13(4):263-268 (Aug. 2000).

Bonhoeffer P., et al., "Transcatheter Implantation of a Bovine Valve in Pulmonary Position: A Lamb Study," Circulation, Aug. 15, 2000, vol. 102, pp. 813-816.

Boudjemline et al., "Percutaneous Implantation of a Biological Valve in Aortic Position: Preliminary Results in a Sheep Study," European Heart Journal, vol. 22, p. 630, Abstract Only (Sep. 2001).

Boudjemline Y., et al., "Images in Cardiovascular Medicine: Percutaneous Aortic Valve Replacement in Animals," Circulation, United States, Mar. 16, 2004, vol. 109, p. e161.

Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.

Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.

Boudjemline Y., et al., "Percutaneous Aortic Valve Replacement: Will We Get There?," Heart, British Cardiac Society, England, Dec. 2001, vol. 86, pp. 705-706.

Boudjemline Y., et al., "Percutaneous Implantation of a Biological Valve in the Aorta to Treat Aortic Valve Insufficiency—A Sheep Study," Medical Science Monitor, Apr. 12, 2002 , vol. 8(4), pp. BR113-BR116.

Boudjemline Y., et al., "Percutaneous Implantation of a Valve in the Descending Aorta in Lambs," European Heart Journal, Jul. 2002, vol. 23, pp. 1045-1049.

Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.

Boudjemline Y., et al., "Percutaneous Valve Insertion: A New Approach?," Journal of Thoracic and Cardiovascular Surgery, United States, Mar. 2003, vol. 125(3), pp. 741-742.

Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.

Boudjemline Y., et al., "Steps Toward Percutaneous Aortic Valve Replacement," Circulation, Feb. 12, 2002, vol. 105, pp. 775-778.

Boudjemline Y., et al., "The Percutaneous Implantable Heart Valve," Progress in Pediatric Cardiology, Ireland, 2001 , vol. 14, pp. 89-93.

Boudjemline Y., et al., "Transcatheter Reconstruction of the Right Heart," Cardiology in the Young, England, 2003, vol. 13, pp. 308-311.

Bruce C.J., et al., "Right-sided Valve Disease Deserves Little More Respect," Circulation, 119(2):2726-2734 (May 2009).

Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.

Commeau P et al., "Percutaneous Balloon Dilatation of calcific aortic Valve Stenosis: Anatomical and Haemodynamic Evaluation," British Heart Journal, 59:227-238 (Feb. 1988).

Cribier A., et al., "Percutaneous Transcatheter Implantation of an Aortic Valve Prosthesis for Calcific Aortic Stenosis: First Human Case Description," Circulation, 2002, vol. 106, pp. 3006-3008.

Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.

Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.

Cunanan et al., "Tissue Characterization and Calcification Potential of Commercial Bioprosthetic Heart Valves." Ann. Thorac. Surg., May 15, 2001, pp. S417-S421.

Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.

Dake et al., "Transluminal Placement of Endovascular Stent-Grafts for the Treatment of Descending Thoracic Aortic Aneurysms." New Engl. J. of Med., 331(26):1729-34 (Dec. 1994).

Dalby et al., "Non-Surgical Aortic Valve Replacement" Br. J. Cardiol., 10(6):450-452 (Nov. 2003).

Davidson M.J., et al., "Percutaneous Therapies for Valvular Heart Disease," Cardiovascular Pathology, Jan. 2006, vol. 15, pp. 123-129.

(56)                    References Cited

OTHER PUBLICATIONS

Dewey et al., "Transapical aortic valve implantation: An Animal Feasibility Study", The annals of thoracic surgery, 82:110-116 (Feb. 2006).

Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.

Dotter, "Transluminally-Placed Coilspring Endarterial Tube Grafts," Investigative Radiology, pp. 329-332 (Oct. 1969).

Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).

Extended EP Search Report dated Sep. 24, 2020 in EP Patent Appl. Serial No. 20165841.6 (JVT-0280).

Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).

Ferrari, "Entwicklung eines Verfahrens zum transvaskulären Aortenklappenersatz," Habilitationsschrift, Medizinische Fakultät der Friedrich-Schiller-Universität Jena, Sep. 2003, pp. 49-52. (With English Translation).

Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.

File history for German Patent DE 195 46 692 filed Dec. 14, 1995 and patented Jul. 11, 2002, 111 pages.

Filsoufi F., et al., "Long-term Outcomes of Tricuspid Valve Replacement in the Current Era," Ann. Thorac. Surg., 8(3):845-850 (Sep. 2005).

Greeenberg, "Abdominal Aortic Endografting: Fixation and Sealing." J. Am. Coll. Surg., 194(1):S79-S87 (Jan. 2002).

Grossi A.E. et al., "Impact of Minimally Invasive Valvular Heart Surgery: A Case-Control Study", Ann. Thorac. Surg., 71:807-810 (Mar. 2001).

Gummert J.F. et al., Cardiac Surgery in Germany During 2006: A Report on Behalf of the German Society for Thoracic and Cardiovascular Surgery, Thorac. Cardiov. Surg., vol. 55, (Sep. 2007), pp. 343-350.

Gummert J.F. et al., "Cardiac Surgery in Germany During 2007: A Report on Behalf of the German Society for Thoracic and Cardiovascular Surgery," Thorac. Cardiov. Surg., vol. 56, (Sep. 2008), pp. 328-336.

Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.

Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.

Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.

Hourihan M., et al., "Transcatheter Umbrella Closure of Valvular and Paravalvular Leaks", JACC, Boston, Massachusetts, 20(6):1371-1377 (Nov. 1992).

Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.

Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.

Huber C.H., et al., "Do Valved Stents Compromise Coronary Flow?," European Journal of Cardio-thoracic Surgery, Jan. 23, 2004, vol. 25, pp. 754-759.

Ing F., "Stents: What's Available to the Pediatric Interventional Cardiologist?" Catheterization and Cardiovascular Interventions, 57:374-386 (Jun. 2002).

International Search Report dated Dec. 29, 2003 in Intl PCT Patent Appl. U.S. Appl. No. PCT/DE2003/002669.

International Preliminary Report on Patentability for Appl. No. PCT/IB2017/052718, dated Nov. 22, 2018, 11 pages.

International Search Report and Written Opinion for PCT Application No. PCT/EP2009/052230 dated Jun. 29, 2009, 12 pages.

International Search Report and Written Opinion for PCT Application No. PCT/EP2010/052429 dated Jun. 14, 2010, 12 pages.

International Search Report and Written Opinion for PCT Application No. PCT/EP2011/002524 dated Apr. 23, 2012, 15 pages.

International Search Report and Written Opinion for PCT Application No. PCT/EP2011/052674 dated Jul. 5, 2011, 12 pages.

International Search Report for PCT Application No. PCT/US1999/020736dated Jan. 28, 2000, 3 pages.

International Search Report and Written Opinion for PCT Application No. PCT/EP2009/050762 dated Jun. 23, 2009, 12 pages.

International Search Report & Written Opinionmailed Jul. 18, 2016 for PCT Patent Appl No. PCT/EP2016/059839, 10 pages.

International Search Report and Written Opinion for Appl. No. PCT/EP2016/055783, mailed on May 30, 2016, 15 pages.

International Search Report and Written Opinion for Application No. PCT/EP2013/057431 dated Jul. 26, 2013, 9 pages.

International Search Report and Written Opinion for Application No. PCT/IB2018/050438 mailed Apr. 12, 2018, 11 pages.

International Search Report and Written Opinion for International Application No. PCT/EP2010/063306, dated Nov. 17, 2010, 9 pages.

International Search Report and Written Opinion for PCT Application No. PCT/EP2006/010519 dated Mar. 1, 2007, 13 pages.

International Search Report and Written Opinion for PCT Application No. PCT/US06/36286 dated Jul. 9, 2007, 4 pages.

International Search Report and Written Opinion for PCT Application No. PCT/US2004/041513 dated Jun. 10, 2005, 4 pages.

International Search Report and Written Opinion for PCT Application No. PCT/US2004/043607 dated Mar. 20, 2006, 4 pages.

International Search Report and Written Opinion for PCT Application No. PCT/US2005/020947 dated Oct. 6, 2005, 5 pages.

International Search Report and Written Opinion for PCT Application No. PCT/US2006/038352 dated May 19, 2008, 4 pages.

International Search Report and Written Opinion for PCT Application No. PCT/US2006/043484 dated Jun. 25, 2008, 4 pages.

International Search Report and Written Opinion for PCT Application No. PCT/US2007/003992 dated Jan. 10, 2008, 5 pages.

International Search Report and Written Opinion for PCT Application No. PCT/US2007/02970 dated Oct. 19, 2007, 7 pages.

International Search Report and Written Opinion for PCT Application No. PCT/US2009/060531 dated May 13, 2010, 6 pages.

International Search Report and Written Opinion for PCT/DE2006/000056 dated Jun. 7, 2006, 11 pages.

International Search Report and Written Opinion for PCT/EP2007/061117 dated May 20, 2008, 16 pages.

International Search Report and Written Opinion for PCT/EP2008/003803 dated Aug. 20, 2008, 10 pages.

International Search Report and Written Opinion for PCT/EP2009/055958 dated Oct. 21, 2009, 8 pages.

International Search Report and Written Opinion for PCT/EP2010/056558 dated Oct. 7, 2010, 14 pages.

International Search Report and Written Opinion for PCT/EP2012/067617 dated Dec. 19, 2012, 10 pages.

International Search Report and Written Opinion for PCT/IL2007/001149 dated May 1, 2008, 4 pages.

International Search Report and Written Opinion for PCT/US2011/027730 dated May 25, 2011, 9 pages.

International Search Report and Written Opinion of the International Search Authority for International Application No. PCT/EP2008/064558, date of completion of report is Mar. 18, 2009, 14 pages.

International Search Report for Application No. PCT/DE2001/000837, dated Aug. 7, 2001, 4 pages.

(56)            References Cited

OTHER PUBLICATIONS

International Search Report for Application No. PCT/EP2006/
012455, mailed Sep. 27, 2007, 5 pages.
International Search Report for Application No. PCT/EP2010/
057798, dated Sep. 12, 2010, 6 pages.
International Search Report for Application No. PCT/EP2011/
058506, mailed Nov. 3, 2011, 4 pages.
International Search Report for Application No. PCT/EP2011/
066677, dated Feb. 17, 2012, 7 pages.
International Search Report for Application No. PCT/EP2012/
067617 mailed Dec. 19, 2012, 3 pages.
International Search Report for Application No. PCT/EP2012/
067714 dated Dec. 18, 2012, 3 pages.
International Search Report for Application No. PCT/EP2013/
073318, dated Apr. 17, 2014, 5 pages.
International Search Report for Application No. PCT/EP2014/
065817, mailed Jan. 7, 2015, 6 pages.
International Search Report for Application No. PCT/EP2016/
055783, mailed on May 30, 2016, 5 pages.
International Search Report for Application No. PCT/EP2016/
058532, dated Jul. 11, 2016, 4 pages.
International Search Report for Application No. PCT/IB2008/
002180, dated Apr. 15, 2009, 7 pages.
International Search Report for Application No. PCT/IB2018/
050438 mailed Apr. 12, 2018, 3 pages.
International Search Report for PCT/DE2001/000836 dated Jun. 13,
2001, 6 pages.
International Search Report for PCT/EP2006/010023 dated Mar. 30,
2007, 6 pages.
International Search Report for PCT/EP2007/007413, mailed Jan.
28, 2008, 4 pages.
International Search Report for PCT/IB2017/052718, dated Sep. 5,
2017, 4 pages.
Kato et al., "Traumatic Thoracic Aortic Aneurysm: Treatment with
Endovascular Stent-Grafts." Radiol., 205:657-662 (Dec. 1997).
Khambadkone S., et al., "Nonsurgical Pulmonary Valve Replace-
ment: Why, When, and How?," Catheterization and Cardiovascular
Interventions, United States, Jul. 2004, vol. 62, pp. 401-408.
Khambadkone S., et al., "Percutaneous Implantation of Pulmonary
Valves," Expert Review of Cardiovascular Therapy (England), Nov.
2003, vol. 1(4), pp. 541-548.
Khambadkone S., et al, "Percutaneous Pulmonary Valve Implanta-
tion: Early and Medium Term Results," Circulation, Oct. 28, 2003,
vol. 108(17), p. IV-375.
Klein A.L., et al., "Age-related Prevalence of Valvular Regurgita-
tion in Normal Subjects: A Comprehensive Color Flow Examination
of 118 Volunteers," Journal of the American Society of
Echocardiography, vol. 3, No. 1, (Jan. 1990), pp. 54-63.
Knudsen et al., "Catheter-implanted prosthetic heart valves", Intl J.
of Art. Organs, 16(5): 253-262, May 1993.
Kort et al., "Minimally Invasive Aortic Valve Replacement:
Echocardiographic and Clinical Results." Am. Heart J., Sep. 2001,
vol. 142(3), pp. 476-481.
Kuzela L., et al., "Experimental evaluation of direct transventricular
revascularization," Journal of Thoracic and Cardiovascular Surgery,
57(6):770-773 (Jun. 1969).
Laborde et al., "Percutaneous Implantation of the Corevalve Aortic
Valve Prosthesis for Patients Presenting High Risk for Surgical
Valve Replacement," EuroIntervention, 1(4):472-474 (Feb. 2006).
Lawrence et al., "Percutaneous Endovascular Graft: Experimental
Evaluation", Radiology, May 1987, vol. 163(2), pp. 357-360.
Levi et al., "Future of Interventional Cardiology in Pediactrics."
Current Opinion in Cardiol., 18:79-90 (Mar. 2003).
Levy, "*Mycobacterium chelonei* Infection of Porcine Heart Valves."
The New England Journal of Medicine, Washington DC, 297(12),
Sep. 22, 1977, pp. 667-668.
Lichtenstein et al., "Transapical Transcatheter Aortic Valve Implan-
tation in Humans: Initial Clinical Experience", circulation, Ameri-
can Heart Association vol. 114, Jul. 31, 2006, pp. 591-596.

Lichtenstein, S.V., "Closed heart surgery: Back to the future" The
Journal of Thoracic and Cardiovascular Surgery, vol. 131(5), May
2006, pp. 941-943.
Liu et al., "Effect of Fiber Orientation on the Stress Distribution
within a Leaflet of a Polymer Composite Heart Valve in be Closed
Position", Journal of Biomechanics, 4:1099-1106 (Jan. 2007).
Lonescu et al., "Prevalence and Clinical Significance of Incidental
Paraprosthetic Valvar Regurgitation: A prospective study using
transesophageal echocardiography." Heart, 89:1316-21 (Oct. 2003).
Love S.C. et al., The Autogenous Tissue Heart Valve: Current
Status, Journal of Cardiac Surgery, , Mar. 1991, vol. 6(4), pp.
499-507.
Lutter G., et al., "Percutaneous Aortic Valve Replacement: An
Experimental Study. I. Studies on Implantation," Journal of Tho-
racic and Cardiovascular Surgery, Apr. 2002, vol. 123(4), pp.
768-776.
Lutter G., et al., "Percutaneous Valve Replacement: Current State
and Future Prospects," Annals of Thoracic Surgery, Netherlands,
Dec. 2004, vol. 78, pp. 2199-2206.
Ma L., et al., "Double-Crowned Valved Stents for Off-Pump Mitral
Valve Replacement," European Journal of Cardio-Thoracic Surgery,
Jun. 13, 2005, vol. 28(2), pp. 194-199.
Mack, M.J., "Minimally invasive cardiac surgery", Surg Endosc,
20:S488-S492 (Mar. 2006).
Magovern et al., "Twenty-five-Year Review of the Magovern-
Cromie Sutureless Aortic Valve", Ann. Thorac. Surg., 48:S33-S334
(Jan. 1989).
Maraj et al., Evaluation of Hemolysis in Patients with Prosthetic
Heart Valves, Clin. Cardiol. 21:387-392 (Jun. 1998).
Marcus RH et al., "Assessment of small-diameter aortic mechanical
prostheses: physiological relevance of the Doppler gradient, utility
of flow augmentation, and limitations of orifice area estimation,"
Circulation, 98(9):866-872 (Sep. 1998).
Mckay G. R. et al., "The Mansfield Scientific Aortic Valvuloplasty
Registry: Overview of Acute Hemodynamic Results and Procedural
Complications." J. Am. Coll. Cardiol., 17(2):485-491 (Feb. 1991).
Mills N.L., et al., "Valvulotomy of valves in the saphenous vein
graft before coronary artery bypass," The Journal of Thoracic and
Cardiovascular Surgery, 71(6):878-879 (Jun. 1976).
Mirich et al., "Percutaneously Placed Endovascular Grafts for
Aortic Aneurysms: Feasibility Study", Radiology, 170:1033-1037
(Mar. 1989).
Moazami N et al. "Transluminal Aortic Valve Placement: a Fesibil-
ity Study with a Newly Designed Collapsible Aortic Valve", ASAIO
Journal, vol. 42, No. 2, Mar.-Apr. 1996.
Moulopoulos et al., "Catheter-Mounted Aortic Valves," Annals of
Thoracic Surg., vol. 11, No. 5, May 1971, pp. 423-430.
Munro I., et al., "The possibility of myocardial revascularization by
creation of a left ventriculocoronary artery fistula," The Journal of
Thoracic and Cardiovascular Surgery, 58(1):25-32 (Jul. 1969).
Nath J., et al., Impact of Tricuspid Regurgitation on Long-term
Survival, Journal of the American College of Cardiology, 43(3):405-
406 (Feb. 2004).
Nietlispach F., et al., "Current Balloon-Expandable Transcatheter
Heart Valve and Delivery Systems", Catheterization and Cardio-
vascular Interventions, 75:295-300 (Sep. 2009).
Palacios I.F., "Percutaneous Valve Replacement and Repair: Fiction
or Reality?," Journal of American College of Cardiology, Oct. 2004,
vol. 44(8), pp. 1662-1663.
Palmaz J.C., et al., "Expandable Intrahepatic Portacaval Shunt
Stents: Early Experience in the Dog," American Journal of Roent-
genology, 145 (4):821-825 (Oct. 1985).
Palmaz J.C., et al., "Expandable Intrahepatic Portacaval Shunt
Stents in Dogs with Chronic Portal Hypertension," American Jour-
nal of Roentgenology, 147(6):1251-1254 (Dec. 1986).
Paniagua et al., "Percutaneous Heart Valve in the Chronic in Vitro
Testing Model." Circulation, Sep. 17, 2002, vol. 106: e51-e52.
Parodi J.C., et al., "Transfemoral Intraluminal Graft Implantation
for Abdominal Aortic Aneurysms", Ann. Vasc. Surg., 5(6):491-499
(Nov. 1991).
Pavcnik D., et al., "Aortic and Venous Valve for Percutaneous
Insertion," Minimally Invasive Therapy & Allied Technologies, Jan.
2000, vol. 9(3/4), pp. 287-292.

(56) References Cited

OTHER PUBLICATIONS

Pavcnik D., et al., "Development and Initial Experimental Evaluation of a Prosthetic Aortic Valve for Transcatheter Placement." Radiology, 183:151-154 (Apr. 1992).

Pavcnik et al., "Percutaneous Bioprosthetic Venous Valve: A Long-term Study in Sheep," Jounal of Vascular Surg., vol. 35, No. 3, Mar. 2002, pp. 598-603.

Pawelec-Wojtalk M., "Closure of left ventricle perforation with the use of muscular VSD occluder," European Journal of Cardia-Thoracic Surgery, 27(4):714-716 (Apr. 2005).

Pelton A.R., et al., "Medical Uses of Nitinol," Materials Science Forum, Jan. 2000, vol. 327-328, pp. 63-70.

Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.

Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.

Raillat et al., "Treatment of Iliac Artery Stenosis with the Wallstent Endoprosthesis." AJR, Mar. 1990, vol. 154(3), pp. 613-616.

Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).

Rogers J.H., et al., "The Tricuspid Valve: Current Perspective and Evolving Management of Tricuspid Regurgitation," Circulation, 119(20):2718-2725 (May 2009).

Ruiz C.E., "Transcatheter Aortic Valve Implantation and Mitral Valve Repair: State of the Art," Pediatric Cardiology, Jun. 2005, vol. 26(3), pp. 289-294.

Saliba Z., et al., "Treatment of Obstructions of Prosthetic Conduits by Percutaneous Implantation of Stents," Archives Des Maldies Du Coeur Et Des Vaisseaux, May 1999, pp. 591-596.

Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.

Sochman et al., "Percutaneous Transcatheter Aortic Disc Valve Prosthesis Implantation: A Feasibility Study." Cardiovasc. Intervent. Radiol., Sep. 2000, 23: 384-388.

Stanley et al., "Evaluation of Patient Selection Guidelines for Endoluminal AAA Repair With the Zenith Stent Graft: The Australasian Experience." J. Endovasc. Ther., 8:457-464 (Oct. 2001).

Stassano P., et al., "Mid-term Results of the Valve-on-Valve Technique for Bioprosthetic Failure," European Journal of Cardiothoracic Surgery, Oct. 2000, vol. 18, pp. 453-457.

Stein D.P., et al., "Turbulent blood flow in the ascending aorta of humans with normal and diseased aortic valves", Circulation Research by American Heart Association, 39:58-65 (Jul. 1976).

Steinhoff et al., "Tissue Engineering of Pulmonary Heart Valves on Allogenic Acellular Matrix Conduits." Circulation102 [suppl. III], pp. III-50-III-55 (Nov. 2000).

Thompson et al., "Endoluminal stent grafting of the thoracic aorta: Initial experience with the Gore Excluder," Journal of Vascular Surgery, Jun. 2002, pp. 1163-1170.

Topol, Eric., Textbook of Interventional Cardiology, 4th Ed; Chapter 24: "Endovascular Options for Peripheral Arterial Occlusive and Aneurysmal Disease," Saunders, pp. 499-503, 949-953 (Dec. 2003).

Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).

Vahanian et al., "Percutaneous Approaches to Valvular Disease", Circulation, Apr. 6, 2004, 109: 1572-1579.

Van Herwerden et al., "Percutaneous Valve Implantation: Back to the Future?", Euro. Heart J., Sep. 2002, 23(18): 1415-1416.

Walther et al., "Transapical approach for sutureless stent-fixed aortic valve implantation: experimental results", European Journal of Cardio-thoracic Surgery 29, 703-708 (May 2006).

Webb J.G., et al., "Percutaneous Aortic Valve Implantation Retrograde from the Femoral Artery," Circulation, American Heart Association, Feb. 14, 2006, vol. 113, pp. 842-850.

Weerasinghe A., et al., "First Redo Heart Valve Replacement: A 10-Year Analysis," Circulation, 99(5):655-658 (Feb. 1999).

Weyman AB et al., "Aortic Stenosis: Physics and Physiology—What Do the Numbers Really Mean?", Rev Cardiovasc Med., 6(1):23-32 (Jan. 2005).

White et al., "Endoleak as a Complication of Endoluminal Grafting of Abdominal Aortic Aneurysms: Classification, Incidence, Diagnosis, and Management," J. Endovasc. Surg., 4:152-168 (May 1997).

Yonga G.O., et al., "Percutaneous Transvenous Mitral Commissurotomy in Juvenile Mitral Stenosis", East African Medical Journal, 80(4):172-174 (Apr. 2003).

Yoshioka et al., "Self-Expanding Endovascular Graft: An Experimental Study in Dogs." AJR 151, Oct. 1988, pp. 673-676.

Zhou et al., "Self-expandable Valved Stent of Large Size: Off-Bypass Implantation in Pulmonary Position", Eur. J. Cardiothorac, Aug. 2003, 24: 212-216.

International Search Report & Written Opinion dated Feb. 20, 2024 in Int'l PCT Patent Appl. Serial No. PCT/IB2023/037029 (0464-P040-PCT).

International Search Report & Written Report Opinion dated Apr. 17, 2024 in Int'l PCT Patent Appl. Serial No. PCT/US2023/080979 (P041-PCT) (411001).

EPO Communication of a Notice of Opposition in EP Patent No. 3 730 094 dated Jan. 30, 2025 (363002).

Cheng, et al., "Successful trans-apical aortic valve implantation for a high risk patient with aortic stenosis using a new second-generation TAVI device J-Valve system," J. of Cardiothoracic Surgery, 10(5):1-4 (2015).

Ford, Omar, "JC Medical Becoming Serious Challenger in TAVR Fray" (May 31, 2018), available at: https://www.mddionline.com/cardiovascular/jc-medical-becoming-serious-challenger-in-tavr-fray.

Wei, et al., "A New Transcatheter Aortic Valve Replacement System for Predominant Aortic Regurgitation Implantation of the J-Valve and Early Outcome," J Am Coll Cardiol Intv., 8(14):1831-1841 (2015).

* cited by examiner

Wheel (Valve Size Specific) - 301

Core - 302

Cone - 303

Eyelet Capturing

Eyelet Capturing

Initial Valve Placement

Rhombi Capturing

Rhombi Capturing

Initial Valve Placement

HEART VALVE PROSTHESIS DELIVERY SYSTEM AND METHOD FOR DELIVERY OF HEART VALVE PROSTHESIS WITH INTRODUCER SHEATH AND LOADING SYSTEM

This application is a divisional application of U.S. patent application Ser. No. 16/099,793, filed on Nov. 8, 2018, now U.S. Pat. No. 11,065,138, which is a national stage of PCT/IB2017/052718, filed on May 10, 2017, which claims priority to U.S. Provisional Application No. 62/491,391, filed on Apr. 28, 2017, and U.S. Provisional Application No. 62/336,153, filed on May 13, 2016, the entire contents of each of which are incorporated herein by reference. This application is also related to U.S. Provisional Application No. 62/136,092, filed on Mar. 20, 2015, the entire contents of which are incorporated herein by reference.

The present disclosure relates to a delivery system, a catheter system and a method for the minimally invasive application of prostheses to individuals in need thereof and a method and device for loading a prosthesis onto a catheter system and/or a delivery system.

BACKGROUND

The present disclosure relates to the field of medical devices, in particular to a prosthesis which is transplanted into an individual in need thereof in order to re-establish proper body functions by way of minimally invasive methods and means applicable therefor.

Examples of prostheses that are placed by way of minimally invasive methods are stents and heart valves like aortic and mitral heart valves. Heart valves today are applied e.g. by the transapical, transfemoral, or subclavial route.

Usually the prosthesis is delivered to the implantation site by way of a delivery system also denoted a catheter. The requirements for the catheter by way of transfemoral delivery is more complex as compared with the transapical route because for the narrower, longer and more tortuous pathway.

One example of such a delivery system is disclosed in EP2387977B1. This patent describes a transfemoral catheter for the delivery of an aortic heart valve. The patent does not disclose nor suggest the features described herein.

Usually the prosthesis is radially compressed onto the catheter and crimped to a small size in order pass through the vasculature of the patient and to be delivered to the implantation site. The different systems known in the prior art use catheter systems with a profile of 18 to 26 French. Because of the potential detrimental effect of long-term crimping on the properties of the tissue leaflets, the prosthesis is crimped or loaded onto the catheter in the operating room just prior to use. Typically, the loading procedure is performed in the sterile field by a trained operator using a dedicated loading tool. This adds to the complexity of the implant procedure.

Another consideration is the accurate positioning of the prosthesis into the final implant location. The beating heart causes the native valve annulus to move with the cardiac cycle. This creates a non-stationary target. In some cases, the natural heart beat is interrupted during placement of the prosthesis to create a stationary target. In some cases, the prosthesis is deployed in a stepwise fashion to better control the positioning of the prosthesis. In some cases, the catheter is designed to retract the prosthesis after partial release in case re-positioning of the prosthesis is desired.

Another consideration in the delivery is the maneuvering of the prosthesis by way of the catheter through the vasculature and its bends. The fact that the vasculature is typically narrow, and particularly at the aortic entry into the heart a substantive curve with a narrow angle has to be passed through, represents a substantial challenge for such a delivery procedure and device.

Yet another consideration is the diameter size of catheter system. The diameter size of the crimped prosthesis in the catheter for delivery through the vasculature of the patient may affect the implantation procedure and/or functioning of the prosthesis upon implantation. Many known systems do not achieve an adequate crimping size, and often the prosthesis tissue is negatively affected in known systems during the crimping procedure.

An object of the present disclosure is to provide for a simple and precisely operable delivery system for stents or prostheses, in particular heart valve prostheses which improve or avoid the disadvantages of prior art delivery systems.

On the basis of the problems referenced and outlined above, certain embodiments of the present disclosure may address the issue of delivering and positioning a specialized endoprosthesis for treating a narrowed cardiac valve or a cardiac valve insufficiency which realizes optimum positioning accuracy and anchoring of the emplaced device. In addition, the treatment of the narrowed cardiac valve or cardiac valve insufficiency may be achieved by way of a relatively simple procedure to enable routine treatment of narrowed cardiac valve or cardiac valve insufficiency without major stress to the patient.

EXEMPLARY OBJECTS OF THE DISCLOSURE

One exemplary object of some aspects of the present disclosure includes providing a catheter system for delivery of a prosthesis, e.g. a heart valve. In particular, wherein the heart valve can securely be loaded and crimped by the operator with minimal effort and skill.

Another exemplary object of some aspects of the present disclosure includes providing a catheter and delivery system for a prosthesis designed in a manner in order to facilitate the delivery of the prosthesis to the target site. In some systems of the present disclosure, for example, maneuvering through the vasculature of a patient is possible with reduced or even without the disadvantages known in the prior art.

Another exemplary object of the present disclosure includes a step-wise liberation of the prosthesis in order to place the prosthesis correctly (e.g., with the proper position and/or orientation) at the target site, enable repositioning in this manner and/or fine tuning of the positioning procedure.

SUMMARY

The present disclosure relates in at least one aspect to a catheter having a mechanism for the sequential release of a stent into the vasculature. The stent may be a self-expanding stent. The stent may be covered by a graft. The stent may contain a heart valve prosthesis. The vasculature may include a blood vessel. The vasculature may include a native heart valve. The vasculature may include the annulus of a native heart valve.

In some aspects, the present disclosure relates to a method of sequentially releasing a stent into the vasculature. The method may include in a first step releasing a first end of the stent from the catheter, the first end of the stent contacting the vasculature upon release. The method may include in a second step releasing the second end of the stent, which releases the entire stent from the catheter.

In some aspects, the present disclosure relates to a loading device and a method for loading a prosthesis, preferably a replacement heart valve prosthesis, on a catheter system.

In some aspects, the present disclosure relates to a method of loading a device onto a catheter and/or a delivery device.

BRIEF DESCRIPTION OF THE DRAWINGS

Exemplary embodiments will be described with reference to the appended drawings below.

Of these are.

DETAILED DESCRIPTION

Figure 1:
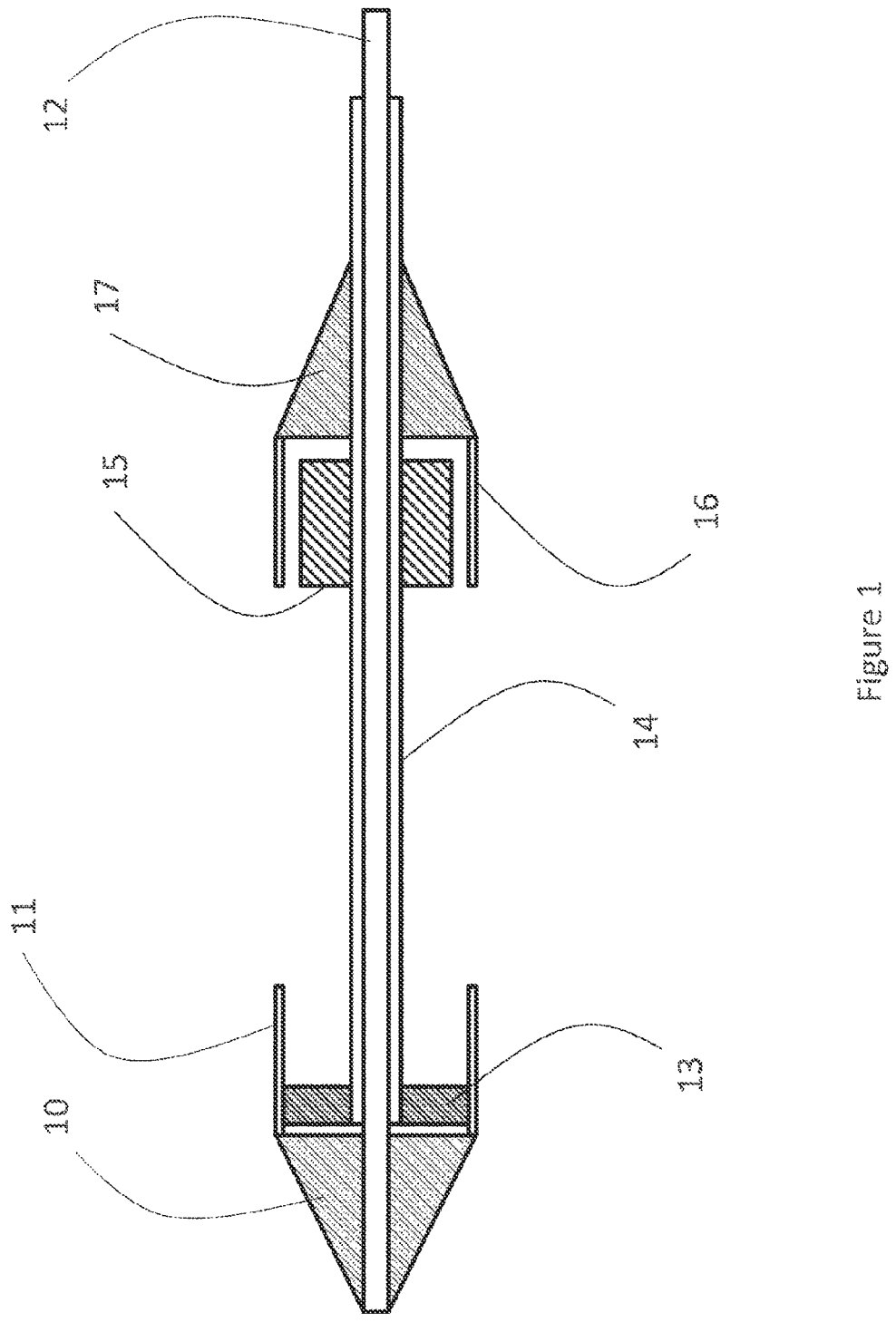
FIG. 1: a section side elevation of a first exemplary embodiment of the catheter.

In at least one aspect, the present disclosure relates to a catheter system for sequential deployment of a stent comprising a first retaining sleeve, a second retaining sleeve, a catheter shaft, and a stent holder, wherein the first sleeve is axially movable with respect to the catheter shaft, the second sleeve is axially fixed to the catheter shaft, the stent holder is axially movable with respect to the catheter shaft.

The various embodiments of the disclosure may address in an advantageous and unexpected manner one or more of the objects discussed above. In particular, in some aspects, the delivery, positioning and/or repositioning of a heart valve prosthesis may be facilitated.

In at least one aspect, the present disclosure relates to a method for sequential deployment of a stent wherein a 1st sleeve (11) of the catheter is moved followed by the movement of a stent holder (15) resulting in the liberation and directed deployment of the stent.

The "stent" as understood by the disclosure can comprise a valve, e.g. a heart valve which can be made of any known and useful tissue, e.g. it can be made of or comprise pericardial tissue. Such a combination can be denoted "prosthesis" or "heart valve prosthesis" In the sense of the disclosure.

The operation of one sleeve or sheath at the distal end by way of an actuator for deployment and positioning the prosthesis may be advantageous and/or may simplify the deployment procedure. Some aspects may have the advantage that also all movements of the movable parts of the catheter part wherein the prosthesis is mounted are effected in basically one direction. This also may apply for the stent holder (15) in connection with the 2nd end (101) of the prosthesis. Accordingly, the procedure may be simplified for the operator of the catheter, and the deployment of the prosthesis may present a lower risk of a wrong or suboptimal deployment and positioning at the target site.

In some aspects, it may be particularly advantageous that the prosthesis release steps are effected by movement in one direction which may result in better controllability and a more precise positioning at the target site, e.g., because the catheter can be kept easier at the target site during the deployment procedure.

The design of some exemplary catheters herein, and the part(s) of the catheters whereon the prosthesis is mounted, may be particularly advantageous in transfemoral (TF) applications. It should be noted that the design of the catheter capsule carrying the prosthesis according to any examples herein may be combined with any handle design containing the engineering features to operate and actuate the particular sleeves and shafts described herein and used for deployment of the prosthesis. The handle may comprise or contain one or several actuating parts or features that actuate the capsule parts in a sequential manner in order to deploy and position the prosthesis precisely and to liberate the prosthesis in a controlled manner at the target site. A "capsule" in the sense of the present disclosure may comprise all components related to mounting, liberating, and deploying the prosthesis or the stent in a controlled manner.

The skilled person will appreciate that materials usually applied in catheter and delivery systems can also be used in any embodiments according to the present disclosure. For example, in a catheter system according to one or more embodiments of the present disclosure, an introducer sheath may be used, and the introducer sheath may be flexible and/or may comprise a flexible polymer, a hydrophilic coating, a PTFE liner, coil reinforcement and/or braid reinforcement.

In at least one embodiment of the catheter system according to the present disclosure the delivery means and steering means are releasably connectable.

Parts that are introduced can be guided by a guide wire known in the art and made from materials as usually applied in the medical field. Usual ports may be applied for trans-femoral use.

It can be advantageous for some aspects of the present disclosure if the tip of the catheter device is soft or semi firm (e.g., made of a soft or semi firm material) and/or for the tip of the catheter device to be bendable (e.g., made of a bendable material) in order to facilitate passage through the vasculature of the patient. Known materials can be used for such a flexible tip.

The catheter and its different sections may be made of appropriate materials as known in the art of catheter design. The materials may comprise, e.g., nitinol, steel, polymers, rubber, and/or Teflon®, and depending on the function of the catheter part the material may be accordingly chosen.

In one aspect the disclosure relates to a catheter system for sequential deployment of a stent or prosthesis comprising a first retaining sleeve, a second retaining sleeve, a catheter shaft, and a stent holder, wherein:

the first sleeve is axially movable with respect to the catheter shaft, the second sleeve is axially fixated to the catheter shaft, the stent holder is axially movable with respect to the catheter shaft.

In another aspect the disclosure relates to a method for sequential deployment of a stent or prosthesis wherein a 1st sleeve (11) of the catheter is moved followed by the movement of a stent holder (15) resulting in the liberation and directed deployment of the stent or prosthesis.

In yet another aspect the disclosure relates to a system for repairing a cardiac valve comprising of a valve prosthesis, a distal segment of the delivery system, and a proximal segment of the delivery system, the valve prosthesis being at least partially retained by the distal segment of the delivery system, the valve prosthesis and the distal segment of the delivery system being stored together in a liquid for transport, the proximal segment of the delivery system being stored dry for transport, means of connecting the distal segment of the delivery system to the proximal segment of the delivery system.

In yet another aspect the disclosure relates to a system for repairing a cardiac valve comprising of one or more configurations of a valve prosthesis, one or more configurations of a distal segment of the delivery system, and one configuration of the proximal segment of the delivery system, the one configuration of the proximal segment of the delivery system being configured such that it connects to the one or more configurations of the distal segment of the delivery system and can deploy one or more configurations of the valve prosthesis.

In yet another aspect the disclosure relates to a method for preparing a system for repairing a cardiac valve for use, the system comprising of a valve prosthesis, a distal segment of the delivery system, and a proximal segment of the delivery system, the method comprising of a first step of engaging the valve prosthesis with the distal segment of the delivery system and a second step of connecting the distal segment of the delivery system to the proximal segment of the delivery system.

In yet another aspect the disclosure relates to a method for preparing a system for repairing a cardiac valve for use, the system comprising of a valve prosthesis, a distal segment of the delivery system, and a proximal segment of the delivery system, the method comprising of a first step of engaging the valve prosthesis with the distal segment of the delivery system, a second step of sterilizing the distal end of the delivery system together with the valve prosthesis, a third step of sterilizing the proximal end of the delivery system separate from the distal end of the delivery system and the valve prosthesis, a fourth step of connecting the distal segment of the delivery system to the proximal segment of the delivery system.

In one aspect of the present disclosure, the placement of a valve prosthesis is considered that consists of a radially collapsible and expandable stent segment and axially oriented support struts. The support struts engage with the native cusps of the diseased aortic valve. Embodiments of such a valve prosthesis are disclosed in patent application WO2011/147849. When placed in the native valve, the expandable stent segment creates a first anchoring force in the radial direction. The support struts create a second anchoring force in the axial direction. Placing such a valve prosthesis at the implant location may include first engaging the support struts with the cusps of the native valve, secondly expanding the expandable stent segment in the native annulus, and finally releasing the remainder of the prosthesis from the delivery catheter. The figures describe exemplary embodiments of the disclosure without to be understood as limiting. Any aspect or feature as disclosed in each of the figures shall be understood as being combinable with all and any other aspects or features of all figures described and depicted in this disclosure.

FIG. 1 shows a section side elevation view of the first exemplary embodiment of the catheter. The catheter comprises a nose cone (10) and a first sleeve (11) connected to the nose cone (10). The nose cone (10) is also connected to a first shaft (12). The first shaft (12) slides within a second catheter shaft (14). A front stop (13) is mounted at the first end of the second catheter shaft (14). A back cone (17) is mounted onto the second shaft (14) and a second sleeve (16) is connected to the back cone (17). A stent holder (15) sits on the second shaft (14). The stent holder (15) can slide freely along the second shaft (14). A back mount (17) is firmly connected to the second shaft (14). A second sleeve (16) is connected to the back mount (17).

Figure 2:
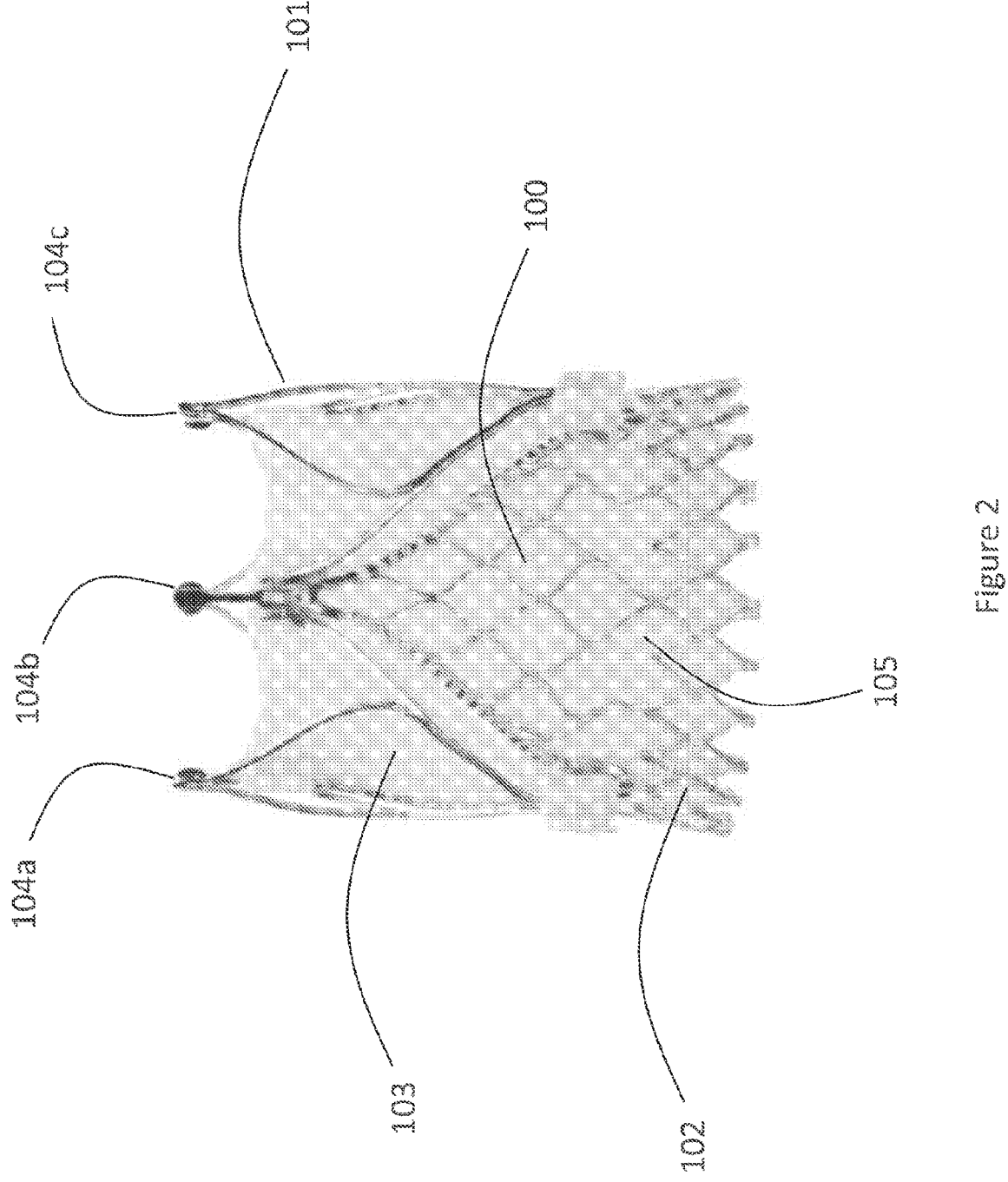
FIG. 2: a side elevation of stent containing a heart valve.

FIG. 2 shows an example of a stent that can be delivered by the catheter in FIG. 1. The stent (100) consists of a first end (102) and a second end (101). The second end (101) may contain eyelets (104a-c) to secure the stent to the delivery system. The stent (100) contains a bioprosthetic valve (103). The first end (102) of the stent (100) is covered by pericardial tissue (105). It is understood that there are many possible embodiments of a stent, and the present disclosure includes other types of stents and stent designs than shown. The stent may be a bare stent, the stent may be a covered stent, the stent may contain a prosthetic valve for replacement of an aortic, mitral, tricuspid, pulmonic, or venous valve. The stent may be braided. The stent may be cut from a metal tube. The stent may be self-expanding. The stent may be actively expanded.

Figure 3:
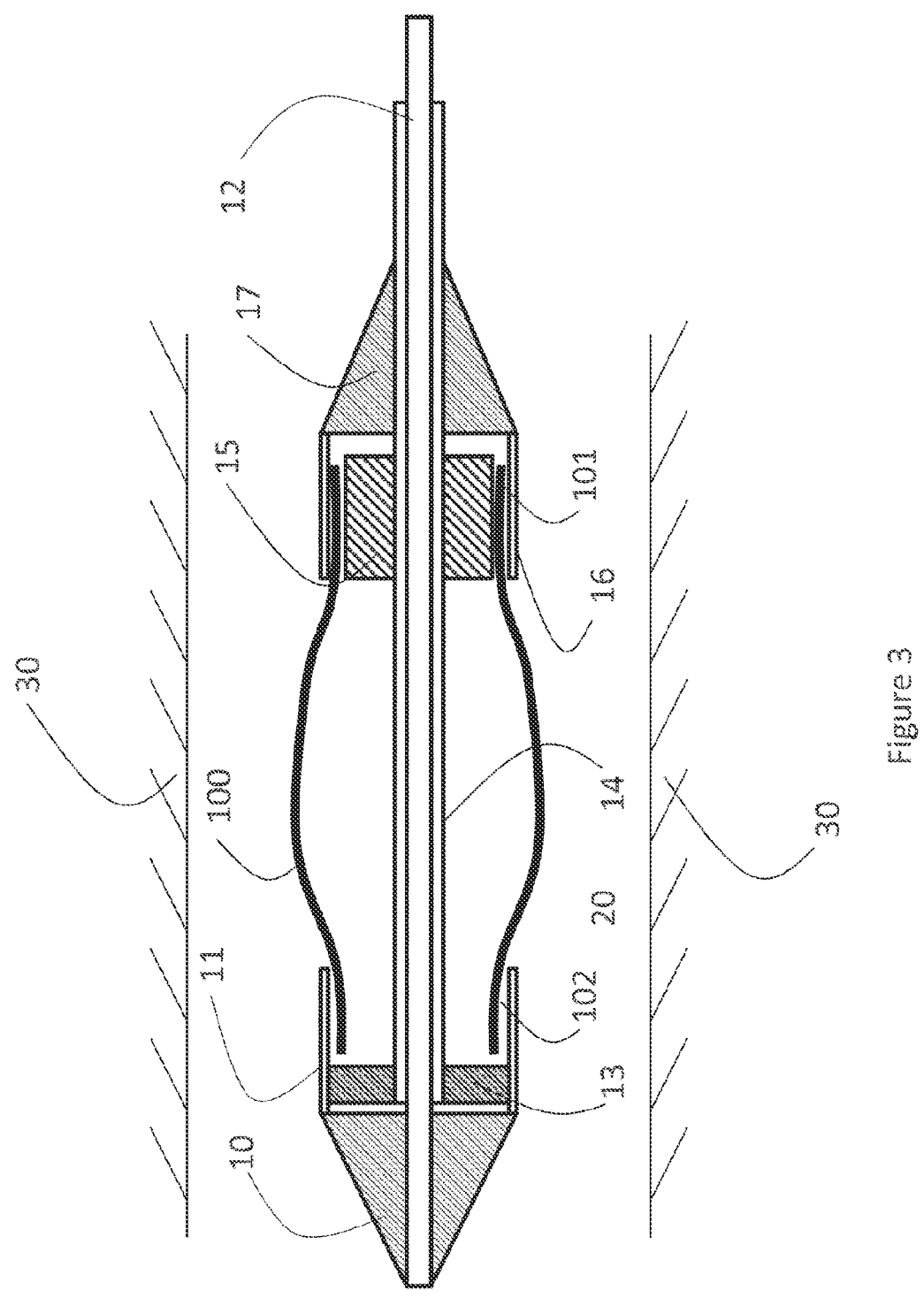
FIG. 3: a sectioned side elevation of the first embodiment of the catheter retaining the stent.

FIG. 3 shows the stent (100) mounted in the catheter of FIG. 1. The first end of the stent (102) is retained by the first sleeve (11). The second end of the stent (101) is retained by the second sleeve (16). A stent holder (15) supports the second end of the stent (102). The stent (100) is sandwiched between the second sleeve (16) and the stent holder (15). The stent holder (15) may contain recesses to engage with the eyelets of the stent (105a-c in FIG. 2). The catheter is positioned in the target vessel (30). The first sleeve (11) and the second sleeve (16) may only partially cover the stent (100) as shown in FIG. 3. The first sleeve (11) and the second sleeve (16) may together completely cover the stent (100). The first sleeve (11) may overlap with the second sleeve (16).

Figure 4:
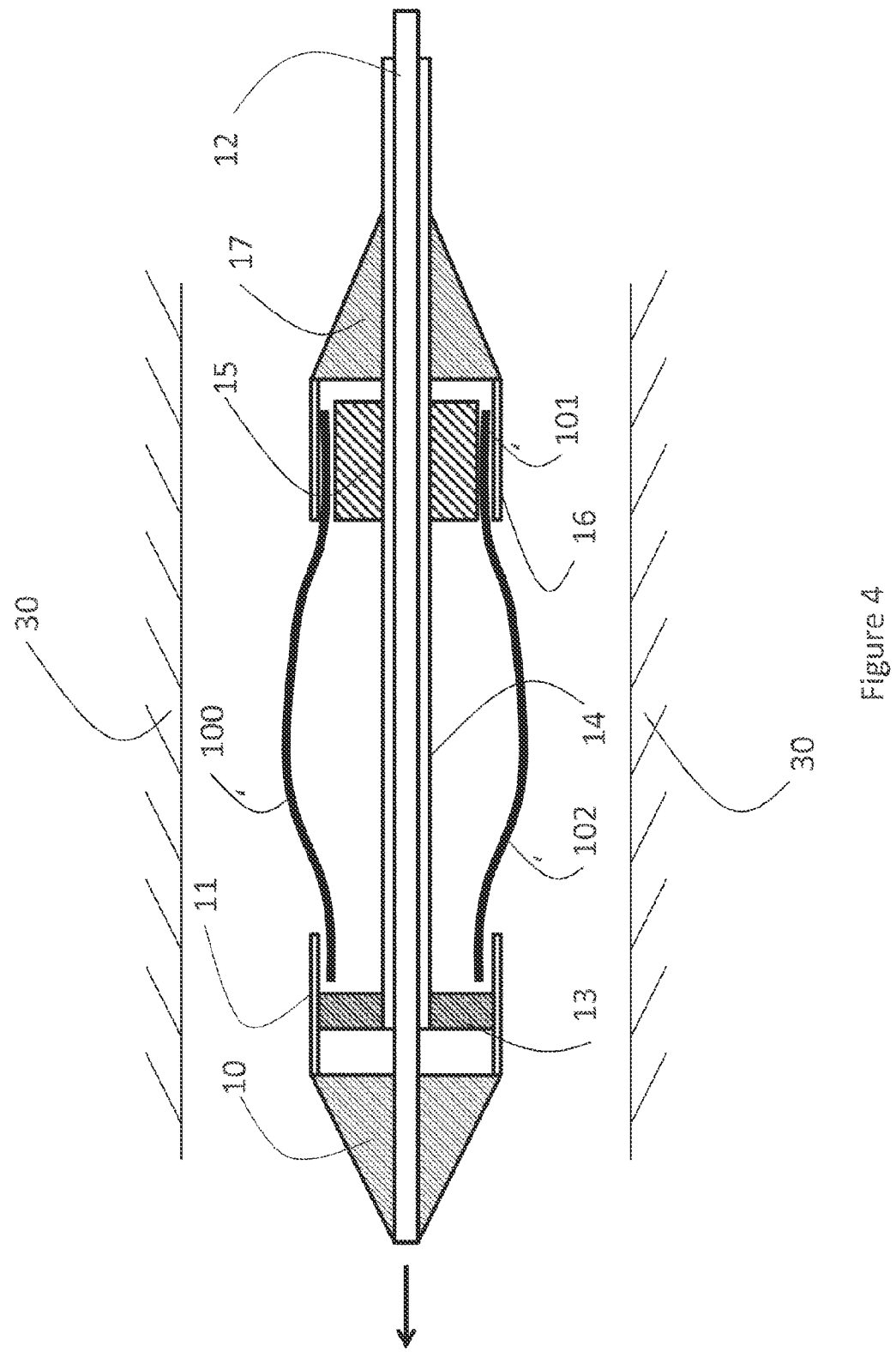
FIG. 4: a sectioned side elevation of the first embodiment of the catheter during deployment step 1.

FIG. 4 shows the delivery catheter of FIG. 1 during the first step of the deployment. The first shaft (12) is advanced distally (toward the tip of the catheter), moving the nose cone (10) and first sleeve (11) distally. The front stop (13) prevents the stent (100) from moving distally. As a result, the first sleeve (11) releases the first end of stent (100).

Figure 5:
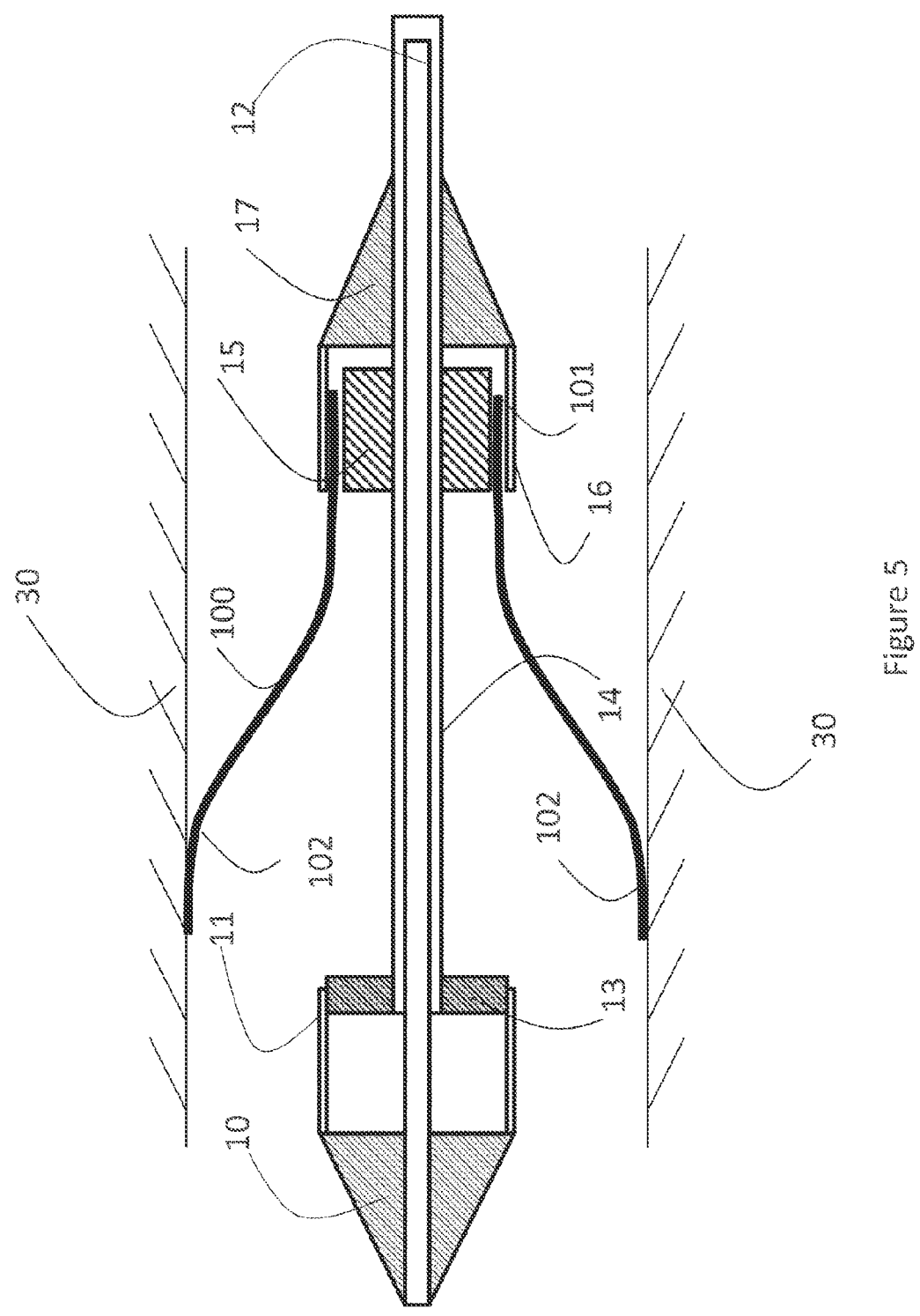
FIG. 5: a sectioned side elevation of the first embodiment of the catheter after completing deployment step 1.

FIG. 5 shows the delivery catheter of FIG. 1 at the end of the first step of the deployment. The first sleeve (11) is advanced distally until the first end of the stent (102) is fully released from the first sleeve (11). The unrestrained first end of the stent (102) expands and contacts the walls of the target vessel (30). The second end of the stent (101) is retained by the second sleeve (16) and the stent holder.

Figure 6:
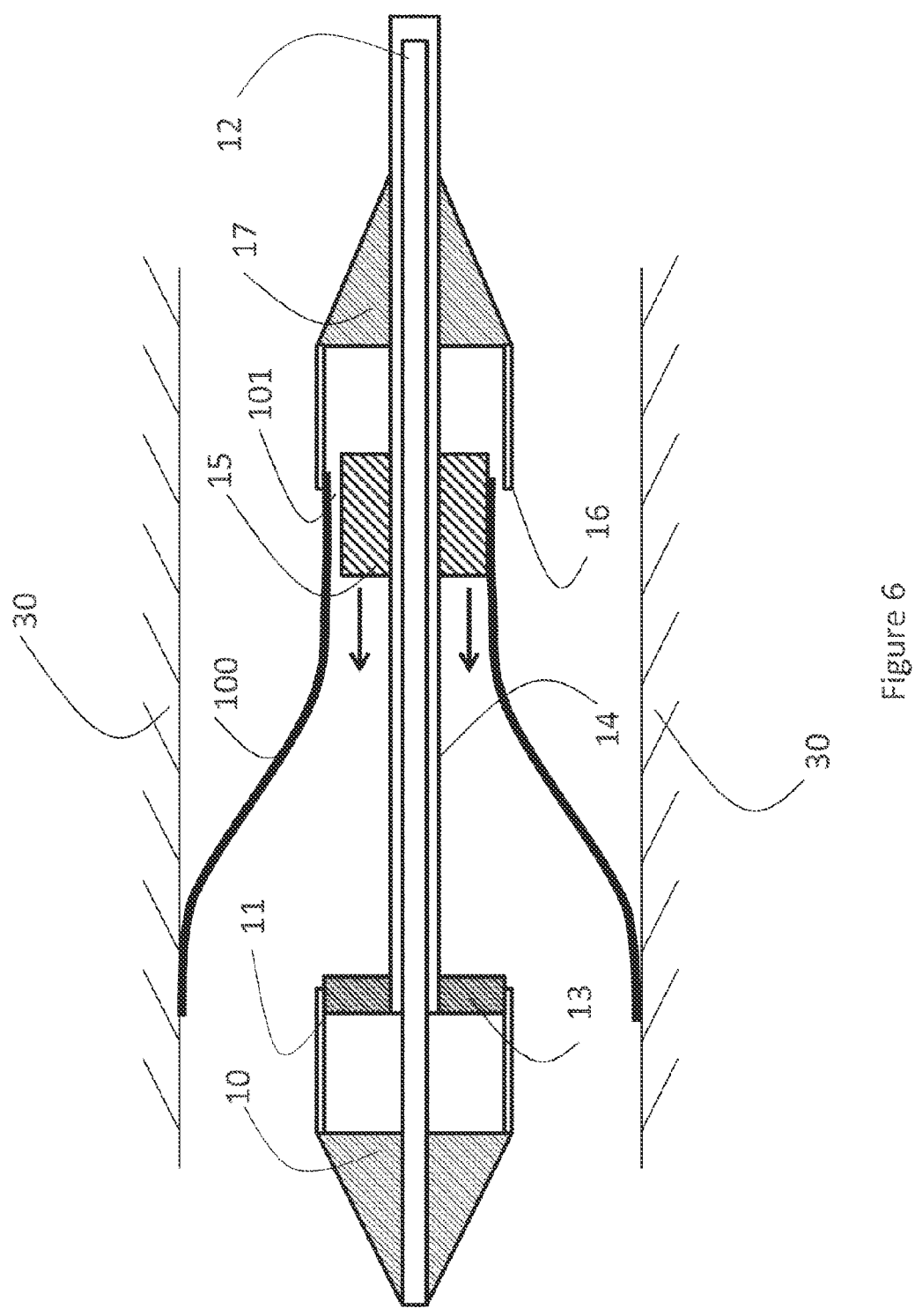
FIG. 6: a sectioned side elevation of the first embodiment of the catheter during deployment step 2.
Figure 7:
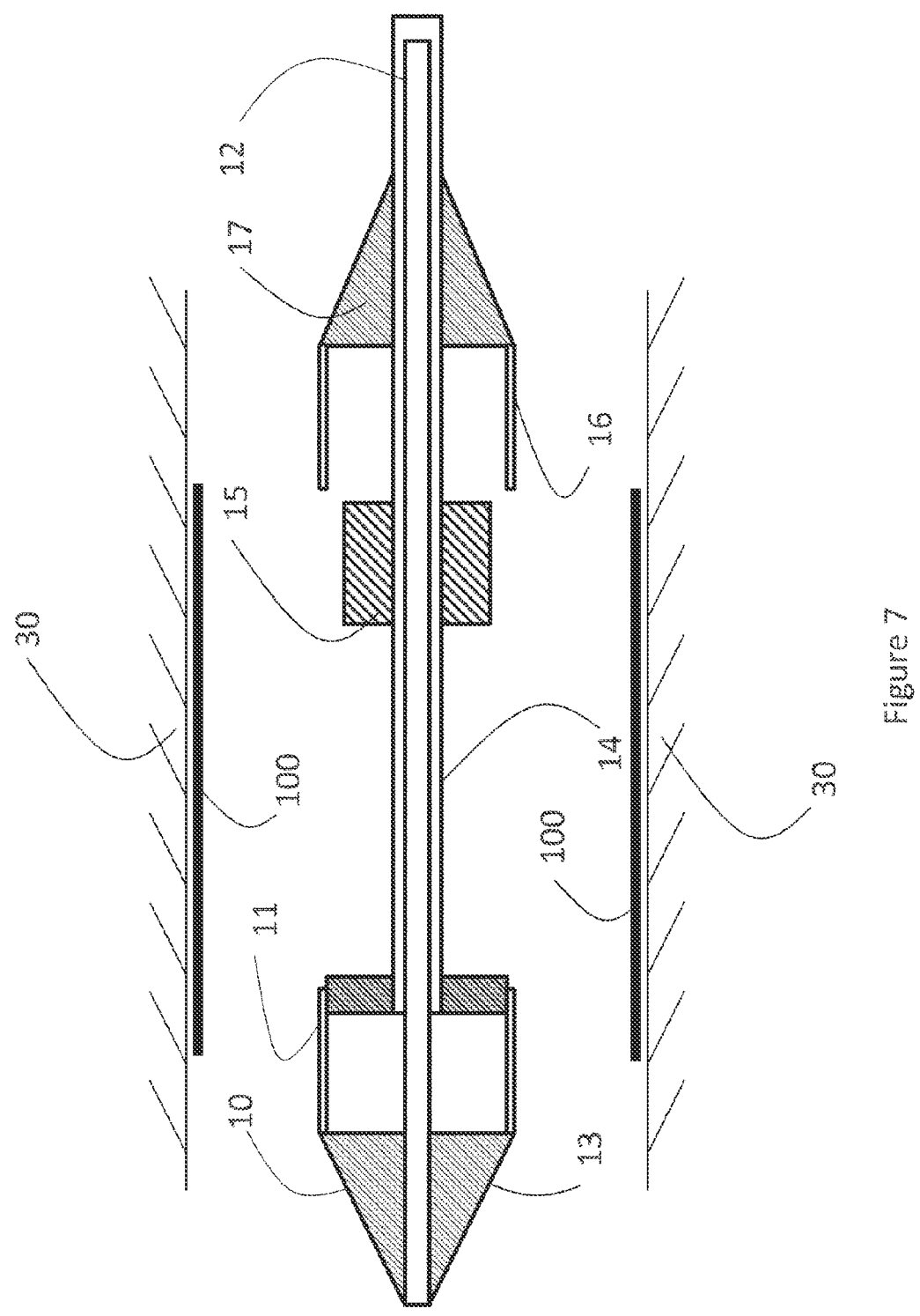
FIG. 7: a sectioned side elevation of the first embodiment of the catheter after completing deployment step 2.

FIG. 6 shows the initiation of the second step of deployment. The stent holder (15) can slide freely along the second shaft (14). Once the first end of the stent (102) is released, the second end of the stent (101) in conjunction with the stent holder (15) can move distally with respect to the second sleeve (16) and the second shaft (14). The movement of the stent (100) and stent holder (16) may be initiated by pulling the second shaft (14) proximally. The first end of the stent (102) is fixed against the walls of the target vessel (30) preventing the stent (100) and the stent holder (16) from moving with the second shaft (14). The distal movement of the stent (100) and stent holder (16) with respect to second shaft (14) causes the second end of the stent (101) to release from the second retaining sleeve (16). FIG. 7 shows the stent (100) fully released from the catheter.

In certain circumstances, active movement of the second shaft (14) proximally may not be required to release the stent (100). The expansion forces of the stent (100) may be sufficient to pull the second end of the stent (101) and the stent holder (15) from the second sleeve (16). Furthermore, the wall of the target vessel (3) may move with the cardiac cycle. For example, the aortic annulus typically moves 0.5 mm to 2 mm axially with every heartbeat. The first end of the stent (102) once anchored to the annulus after completion of the first deployment steps moves with the annulus. This movement may by itself or in conjunction of the expansion forces of the stent (100) may be sufficient to pull the second end of the stent (101) and the stent holder (15) from the second sleeve (16).

Figure 8:
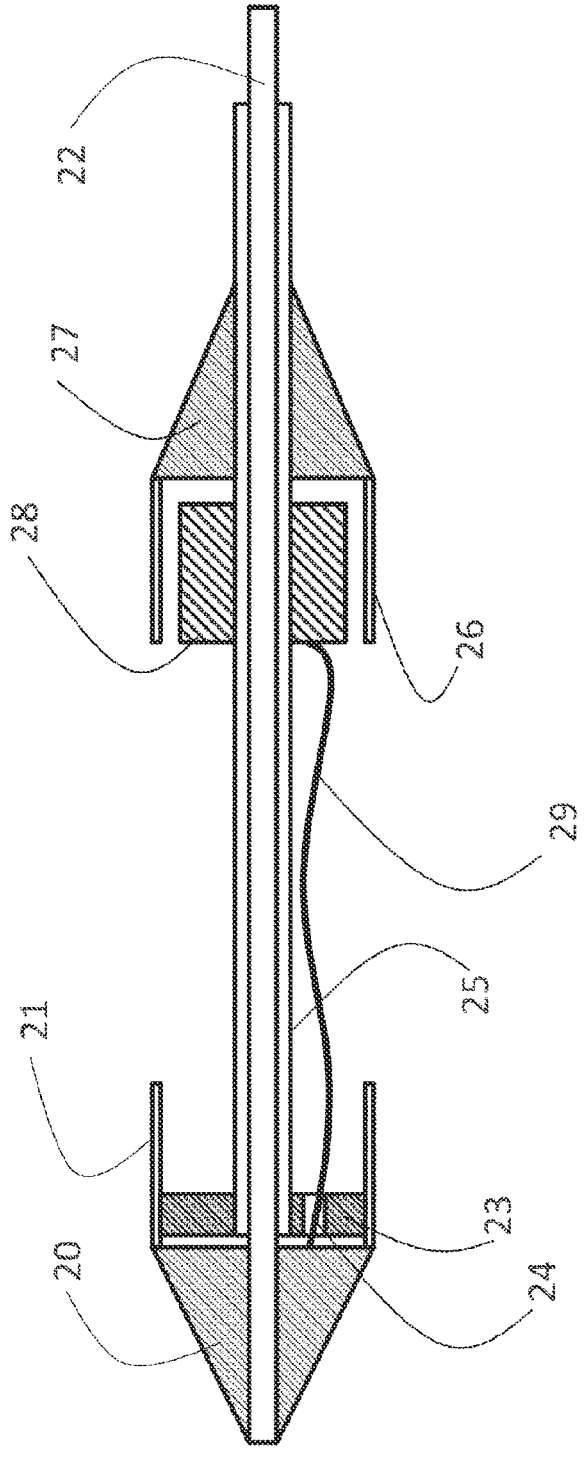
FIG. 8: a section side elevation of a second exemplary embodiment of the catheter.

FIG. 8 shows another exemplary embodiment of the delivery catheter. The catheter comprises a nose cone (20) and a first sleeve (21) connected to the nose cone (10). The nose cone (20) is also connected to a first shaft (22). The first shaft (22) slides within a second catheter shaft (25). A front stop (23) is mounted at the first end of the second catheter shaft (25). The front stop contains a passage (24). A back cone (27) is mounted onto the second shaft (25) and a second sleeve (26) is connected to the back cone (27). A stent holder (28) sits on the second shaft (25). The stent holder (28) can slide freely along the second shaft (25). A cable (29) connects the stent holder (28) to the nose cone (20). The cable (29) passes through the passage (24) in the front stop (23). The cable (29) is longer than the distance between the stent holder (28) and the nose cone (20). A back mount or back cone (27) Is firmly connected to the second shaft (25). A second sleeve (26) is connected to the back mount (27).

Figure 9:
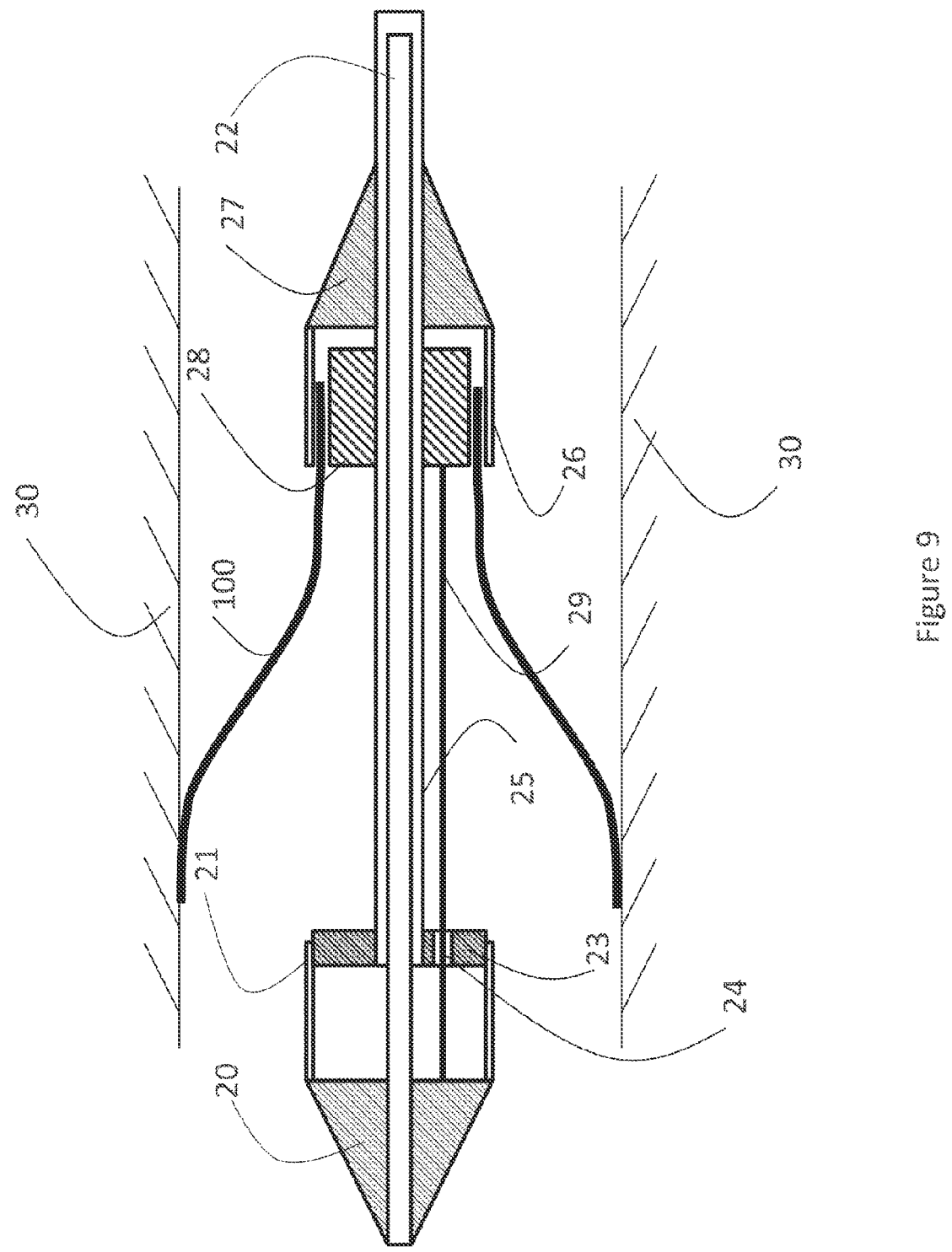
FIG. 9: a section side elevation of a second embodiment of the catheter after completion of deployment step 1.

FIG. 9 shows the delivery catheter of FIG. 8 after completion of the first deployment step. The first shaft (22), nose cone (20), and the first sleeve (21) are advanced distally, which released the first end of the stent (102). In this configuration, the distance between the stent holder (28) and the nose cone (20) is approximately equal to the length of the cable (29). The cable (29) is fully extended.

Figure 10:
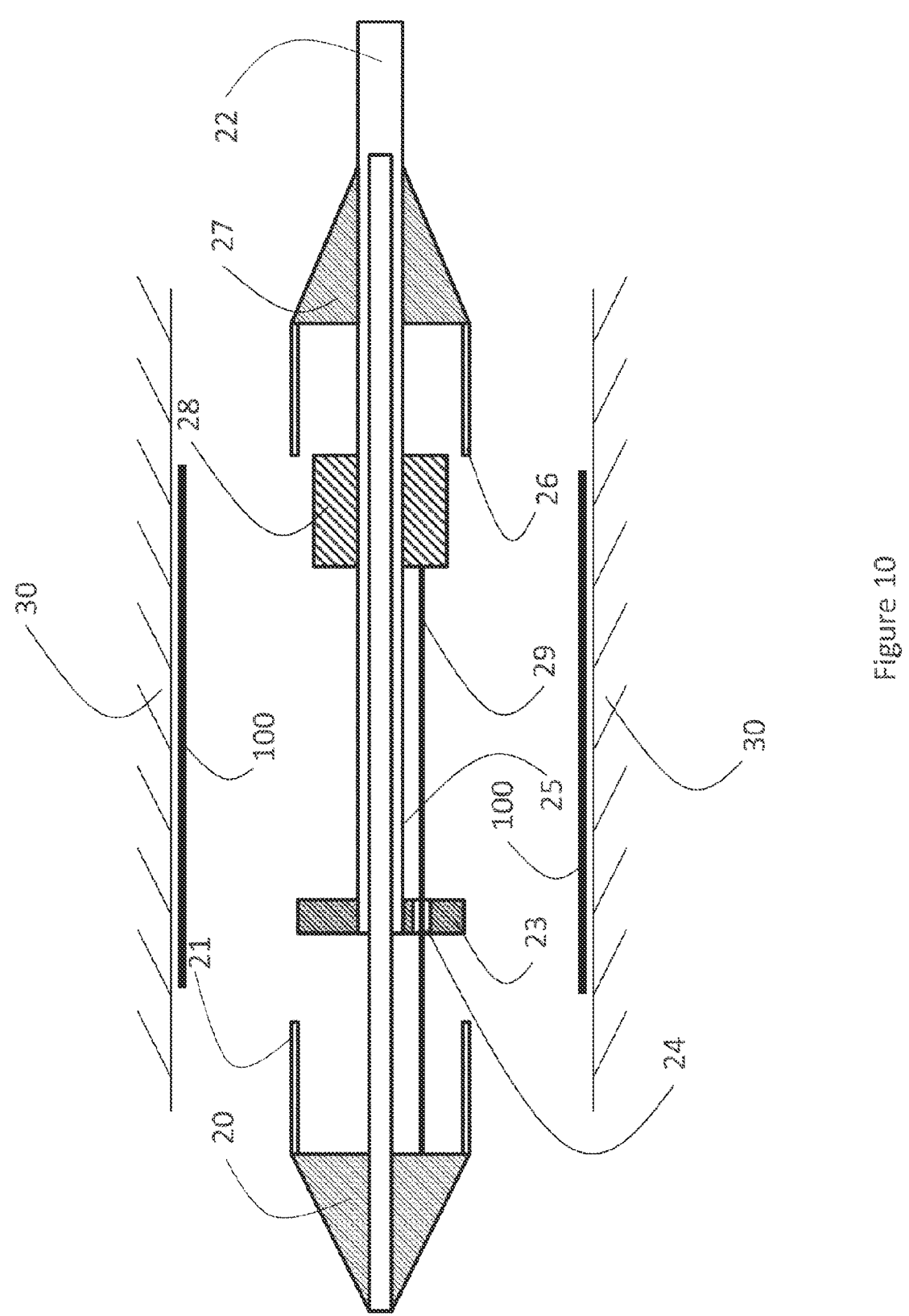
FIG. 10: a section side elevation of a second embodiment of the catheter after completion of deployment step 2.

FIG. 10 shows the delivery catheter of FIG. 8 after completion of the second deployment step. The first shaft (25), nose cone (20), and the first sleeve (21) are further advanced distally. The cable (29) pulls the stent holder (28) distally and out of the second sleeve (26). The second end of the stent (101) Is released from the catheter. The cable (29) provides the means for a sequential release of the first end (102) and the second end (101) of the stent (100) by a single movement of the first shaft. Other means of connecting the front assembly consisting of the nose cone (20), the first sleeve (21), and the first shaft (22), with the stent holder (28) may be considered and used herein. The connecting element may be a tension spring that when placed under tension after completion of the first deployment step pulls the stent holder (28) distally. The connecting element may be a rode that is fixed to the nose cone (20) and can pass through a channel in the stent holder (28). The end of the rode that passes through the channel has an enlarged end cap that cannot pass through the channel. As the rode is pulled distally by the front assembly, the end cap catches the stent holder (28) at the end of the first deployment step and pulls the stent holder (2) distally during the second deployment step.

Figure 11:
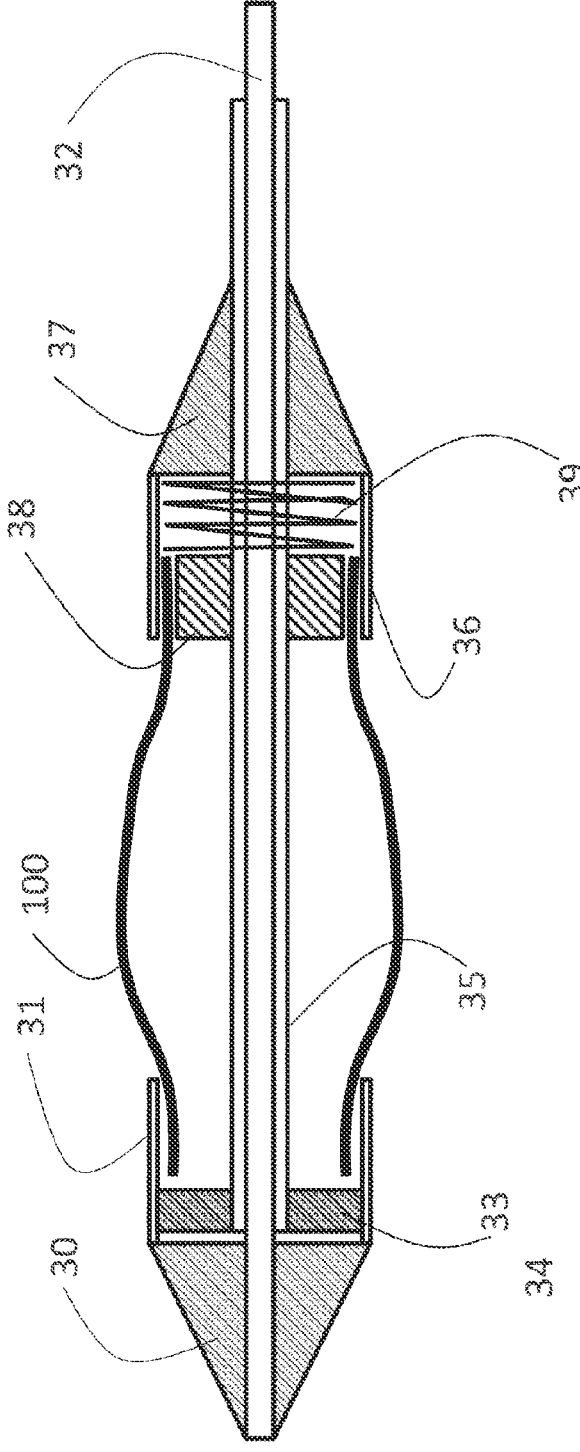
FIG. 11: a section side elevation of a third exemplary embodiment of the catheter containing a stent.

FIG. 11 shows yet another exemplary embodiment of the delivery catheter. The catheter comprises a nose cone (30) and a first sleeve (31) connected to the nose cone (30). The nose cone (30) is also connected to a first shaft (32). The first shaft (32) slides within a second catheter shaft (35). A front stop (33) is mounted at the first end of the second catheter shaft (35). A stent holder (38) sits on the second shaft (35). The stent holder (38) can slide freely along the second shaft (35). A back mount (37) is firmly connected to the second shaft (35). A second sleeve (36) is connected to the back mount (37). A compression spring (39) is mounted on the second shaft (35) between the stent older (38) and the back mount (37). The stent (100) is retained by the first sleeve (31) and the second sleeve (36).

Figure 12:
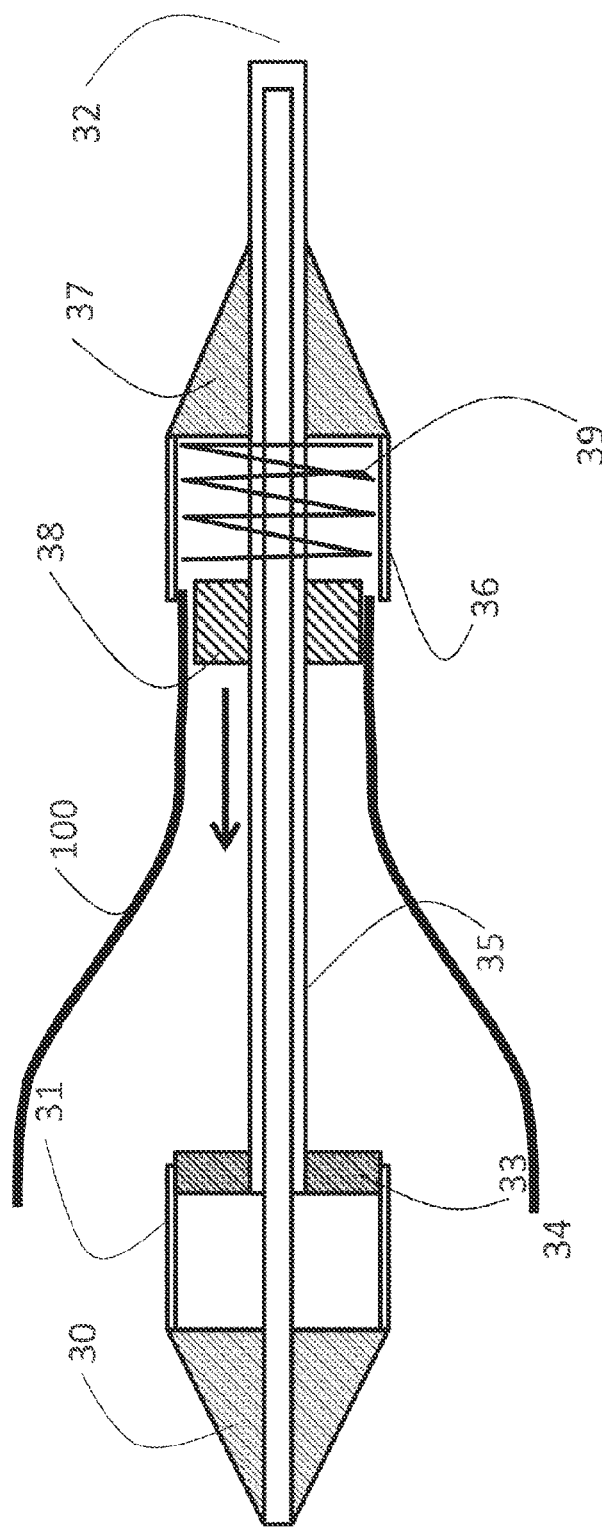
FIG. 12: a section side elevation of a third embodiment of the catheter after completion of deployment step 1.

FIG. 12 shows the catheter of FIG. 11 after completion of the first deployment step and initiation of the second deployment step. The first shaft (32), nose cone (30), and the first sleeve (31) are advanced distally, which releases the first end of the stent (102). In this configuration, the spring (39) pushes the stent holder (38) from the second sleeve (36) which then releases the second end of the stent (101) from the catheter.

The catheter or delivery system as disclosed herein can be characterized by the above features alone or in combination with the below features, or it can be characterized by any of the below features alone or any combination thereof or a combination of the above features and any of the below described features.

Figure 13:
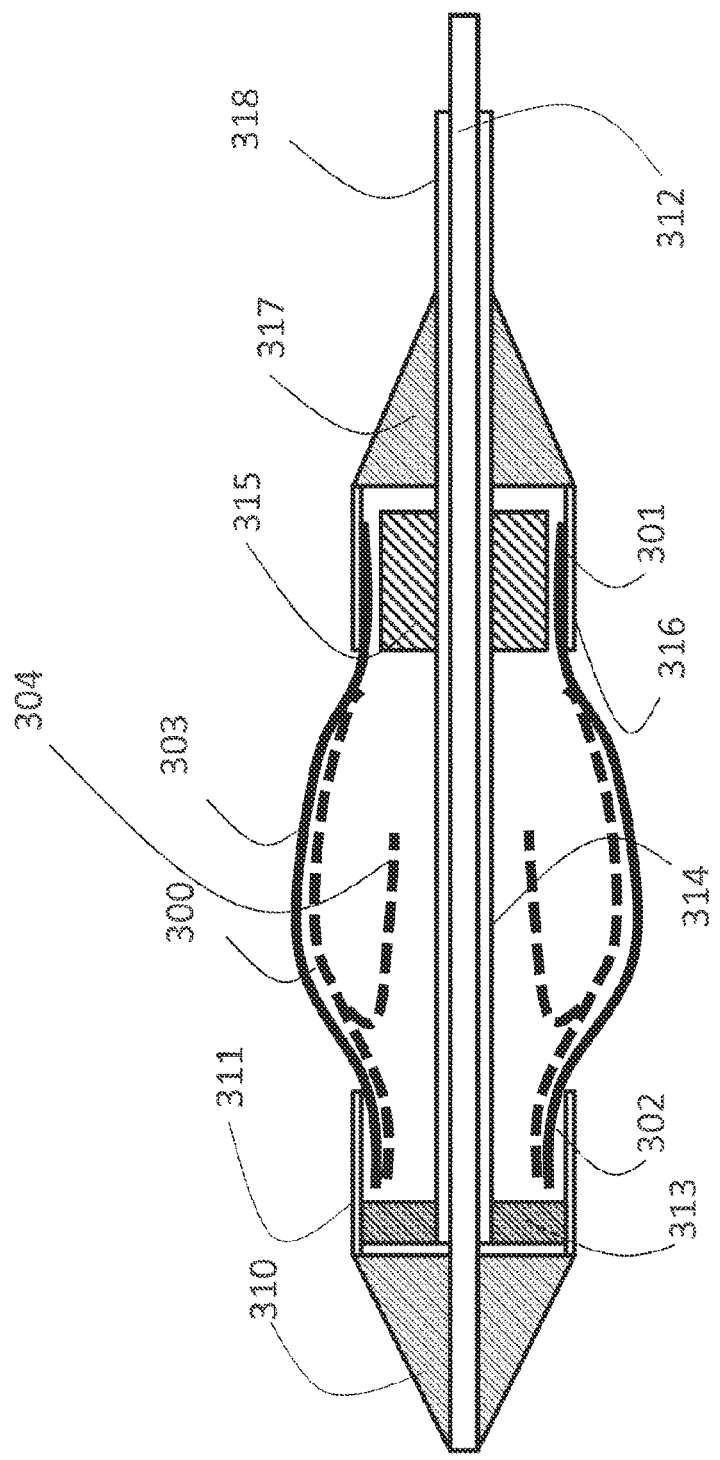
FIG. 13: a valve prosthesis partially collapsed in an exemplary delivery system.
Figure 14:
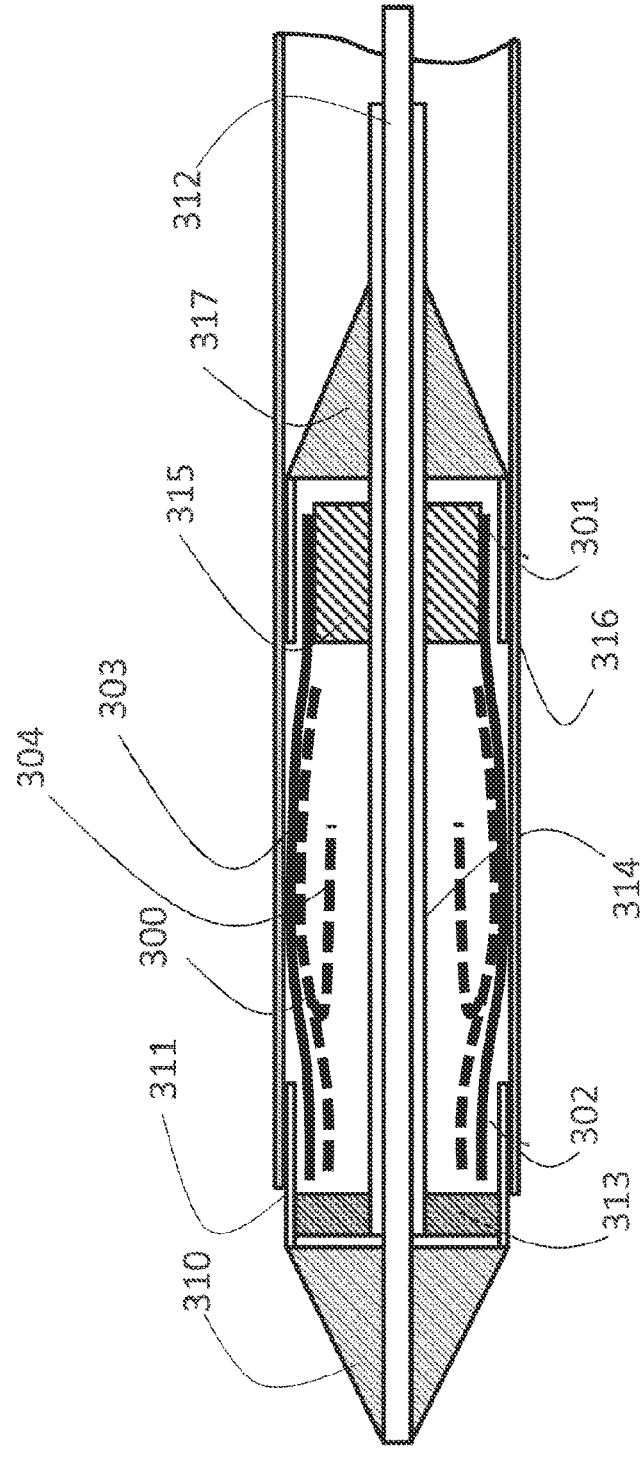
FIG. 14: a valve prosthesis fully collapsed in the delivery system.

Typically, transcatheter valve prostheses are stored separately from the delivery system in a liquid solution to preserve the animal tissue, which form the leaflets of the valve prosthesis. The valve prosthesis is loaded onto the delivery system in the operating room immediately before use. Special loading tools and precise instructions and training of the operator are necessary to ensure proper loading. In another aspect of the present disclosure, preloading of the valve prosthesis onto the delivery system before packaging and shipment to hospital is considered. FIG. 13 shows a cross-sectional view of the valve prosthesis crimped in the delivery system described in FIGS. 3-7. The distal end of the delivery system comprises or consists of a nose cone (310), a first sleeve (311) connected to the nose cone (310), a first shaft (312) connected to the nose cone (312), a second sleeve (316) connected to a back cone (317), a second shaft (318) coaxial and external to the first shaft (312) connected to the back cone, a front stop (313) connected to the second shaft (318), and stent holder (315). The stent holder (315) can move axially with respect to the second shaft (318). The first shaft can move axially within the second shaft (318). The proximal end (302) of the valve prosthesis (300) is retained by the first sleeve (311) and the distal end (301) of the valve prosthesis (300) is retained by the second sleeve. The midsection (303) of the valve prosthesis (300) is unconstrained and has a diameter larger than the crimped distal end (301) and proximal end (302). The tissue leaflets (304) which are located in the midsection (303) of the valve prosthesis (300) are slightly folded but not crimped. In FIG. 14, the valve prosthesis (300) is fully collapsed for insertion into the patient. The midsection (303) of the valve prosthesis is constrained by the introducer sheath (316) and the tissue leaflets (304) are fully crimped.

The current disclosure contemplates shipping and storing the valve prosthesis in the configuration shown in FIG. 13. In the operating room prior to use, the operator slides the introducer sheath (316) over the midsection (303) of the valve prosthesis to prepare the system for insertion in the patient. It is further contemplated to separate the distal end of the delivery system, which houses the valve prosthesis, from the remaining proximal section of the delivery system. The valve prosthesis is pre-loaded onto the distal end of the delivery system and stored in one container. The proximal segment of the delivery system is stored in a second container. Prior to use the two components of the delivery system are connected.

Figure 15:
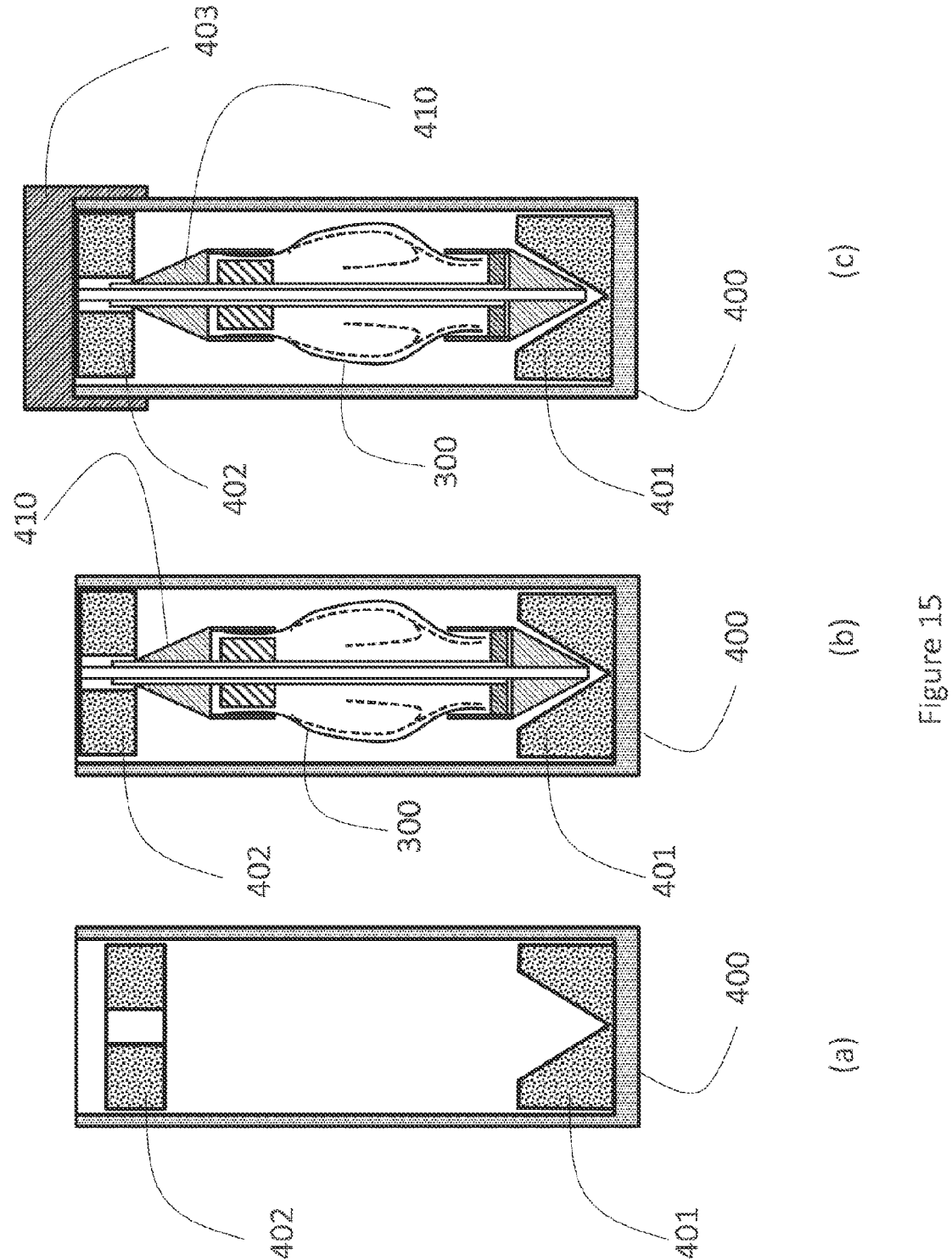
FIG. 15: an embodiment of a storage container for the valve prosthesis and distal section of the delivery system.

FIG. 15 shows one embodiment of the storage container (400) for the pre-loaded valve prosthesis (300). The container (400) is designed to contain a liquid storage solution to maintain sterility and prevent dehydration of tissue leaflets. The storage solution may contain gluteraldehyde, formaldehyde, alcohol, TWEEN, and other chemical(s) suitable for storing cross-linked tissue. The tissue may be harvested from an animal. The tissue may be harvested from the animal's pericardium, blood vessels, cardiac valve, or intestines. The container (400) contains a distal holder (401) and a proximal holder (402). The distal end of the delivery system (410) retains the proximal section (302) and distal section (301) of the valve prosthesis (300). A lid hermetically (403) seals the container (400).

Figure 16:
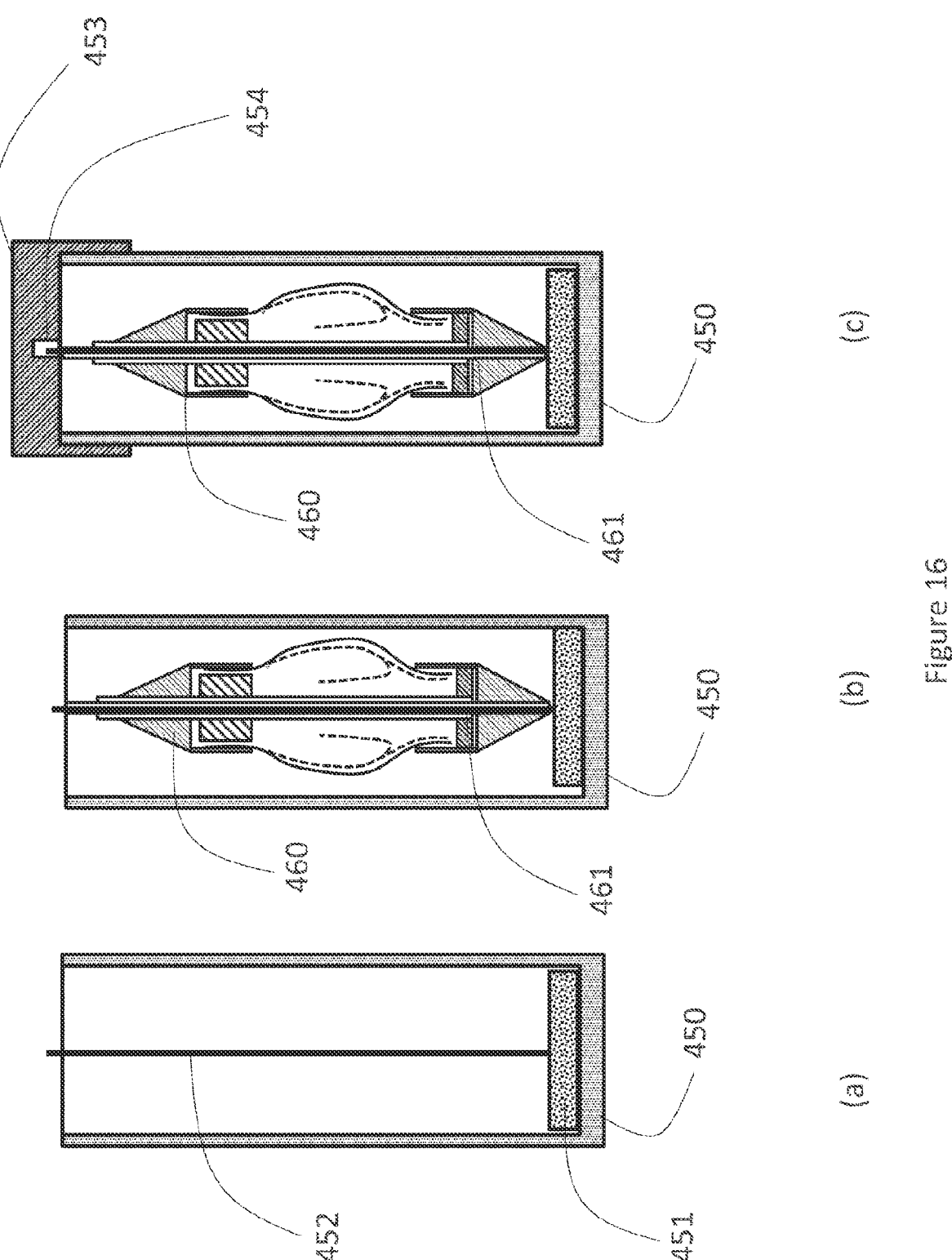
FIG. 16: an alternative embodiment of a storage container for the valve prosthesis and distal section of the delivery system.

FIG. 16 shows an alternative embodiment of the storage container. The container (450) contains a distal holder (451). A rode (452) is connected to the distal holder (451). The rod (452) passes through the guidewire lumen (461) of the distal segment of the delivery system (460) and centers the distal segment of the delivery system (460) In the container (450). A lid (453) hermetically seals the container (450). A central recess (454) in the lid (453) stabilizes and centers the rod (452).

Figure 17:
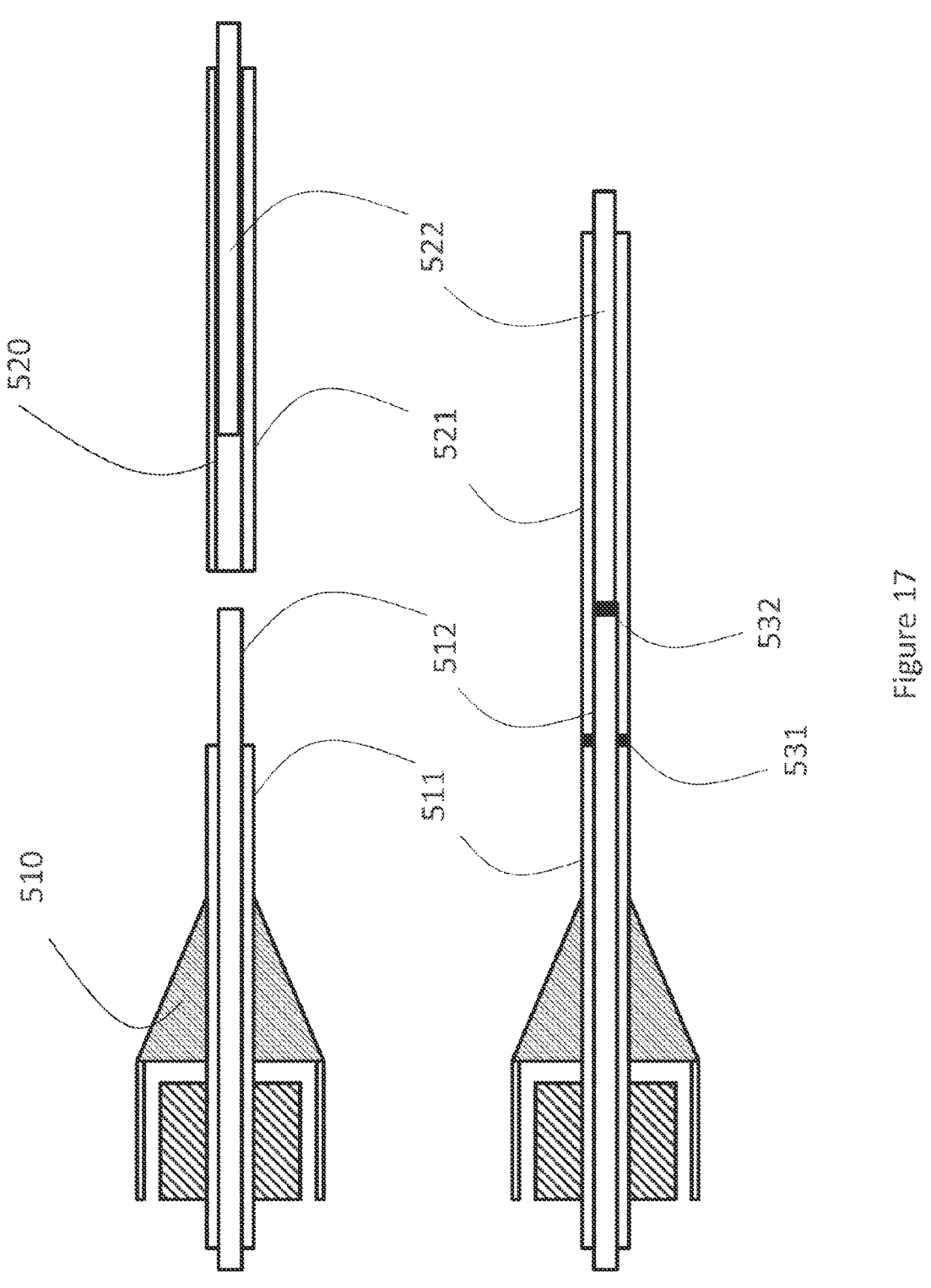
FIG. 17: a first embodiment of an attachment mechanism between the distal and proximal section of the delivery system.

FIG. 17 illustrates exemplary means of connecting the distal segment of the delivery system (510) to the proximal segment of the delivery system (520). To make the assembled delivery system fully operable, the outer shaft (521) of the proximal segment (520) Is connected to the outer shaft (511) of the distal segment (510) of delivery system by an outer connector (531) and the inner shaft (522) of the proximal segment (520) is connected to the inner shaft (512) of the distal segment (510) of delivery system by an inner connector (532). The means of connection may include, but are not limited to, a male-female luer connector, a male-female thread, an interference press fit between the proximal and distal shaft, an adhesive, magnets, barbs, clips, combinations thereof, or any other suitable means of connecting two tubular segments.

Figure 18:
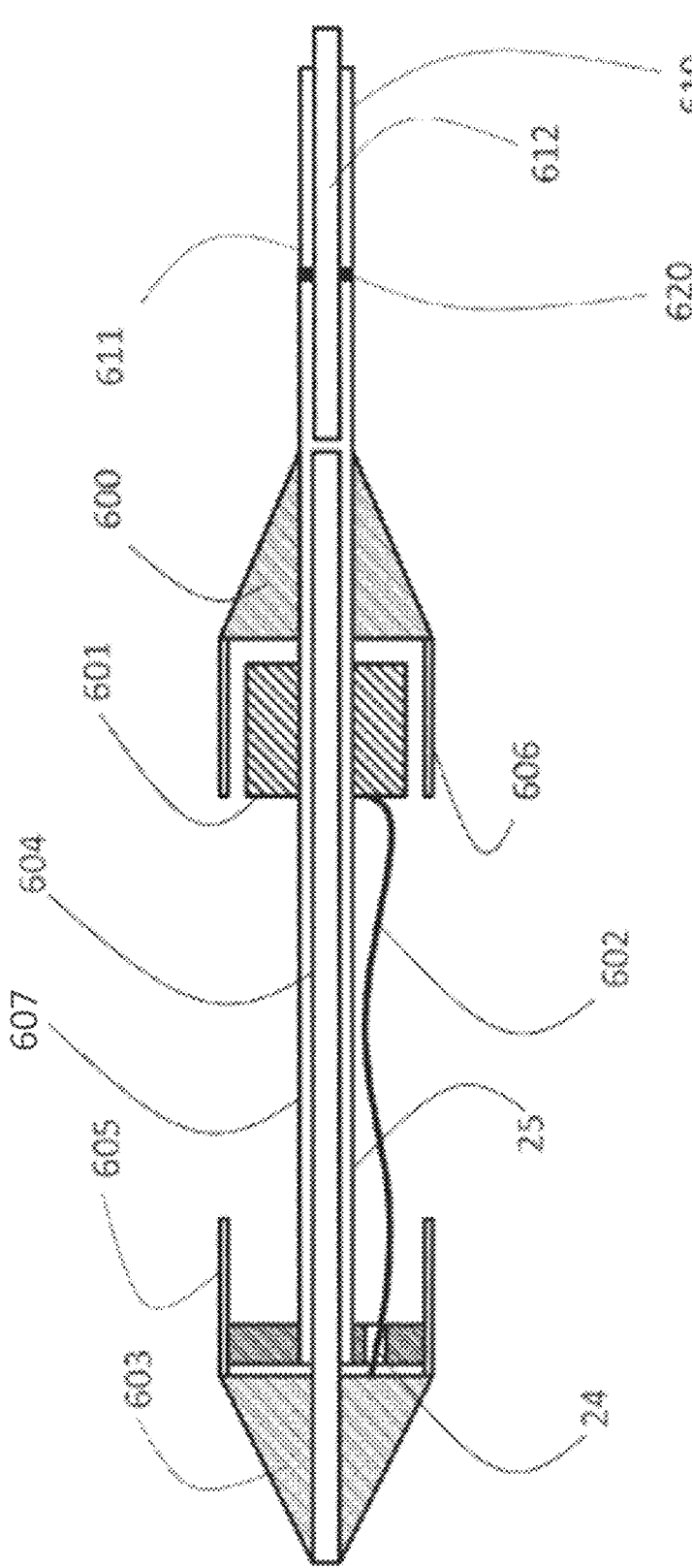
FIG. 18: a second embodiment of the distal section of the delivery system and attachment mechanism to the proximal end of the delivery system.

FIG. 18 shows an embodiment of the delivery system previously described in FIG. 8. In this embodiment, the stent holder (601) is connected with a cable, wire or string (602) to the nose cone (603) of the delivery system. The inner shaft (604) of the distal delivery system segment (600) is connected to the nose cone (603). Advancing the inner shaft (604) distally sequentially moves the first sleeve (605) distally to release the proximal end of the valve prosthesis and then the stent holder (601) to release the distal end of the valve prosthesis from the second sleeve (606). To operate the distal segment of the delivery system (600) from the proximal end (610) of the delivery system, the outer shaft (607) of the distal segment of the delivery system (600) is connected to the outer shaft (611) of the proximal segment of the delivery system (610) by a first connector (620). The inner shaft (604) of the distal segment of the delivery system (600) is axially aligned but not physically connected with the inner shaft (612) of the proximal segment of the delivery system (610). Advancing the inner shaft (612) of the proximal delivery system (610) also advances the inner shaft (604) of the distal segment of the delivery system (600). The advantage of the embodiment of FIG. 18 is that only a single connector is needed to assembly the proximal and distal segment of the delivery system.

Figure 19:
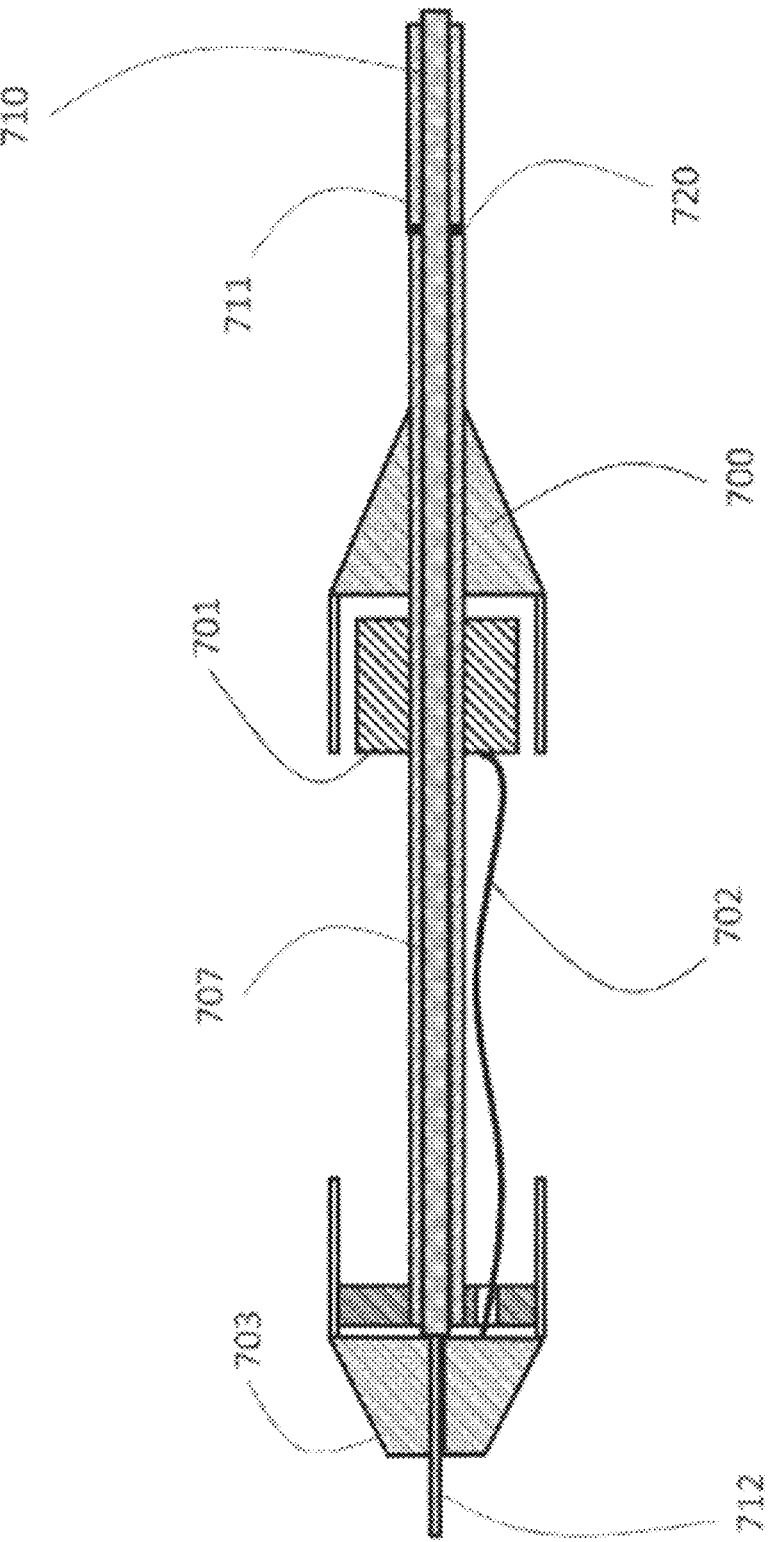
FIG. 19: a third embodiment of the distal section of the delivery system and attachment mechanism to the proximal end of the delivery system prior to assembly.
Figure 20:
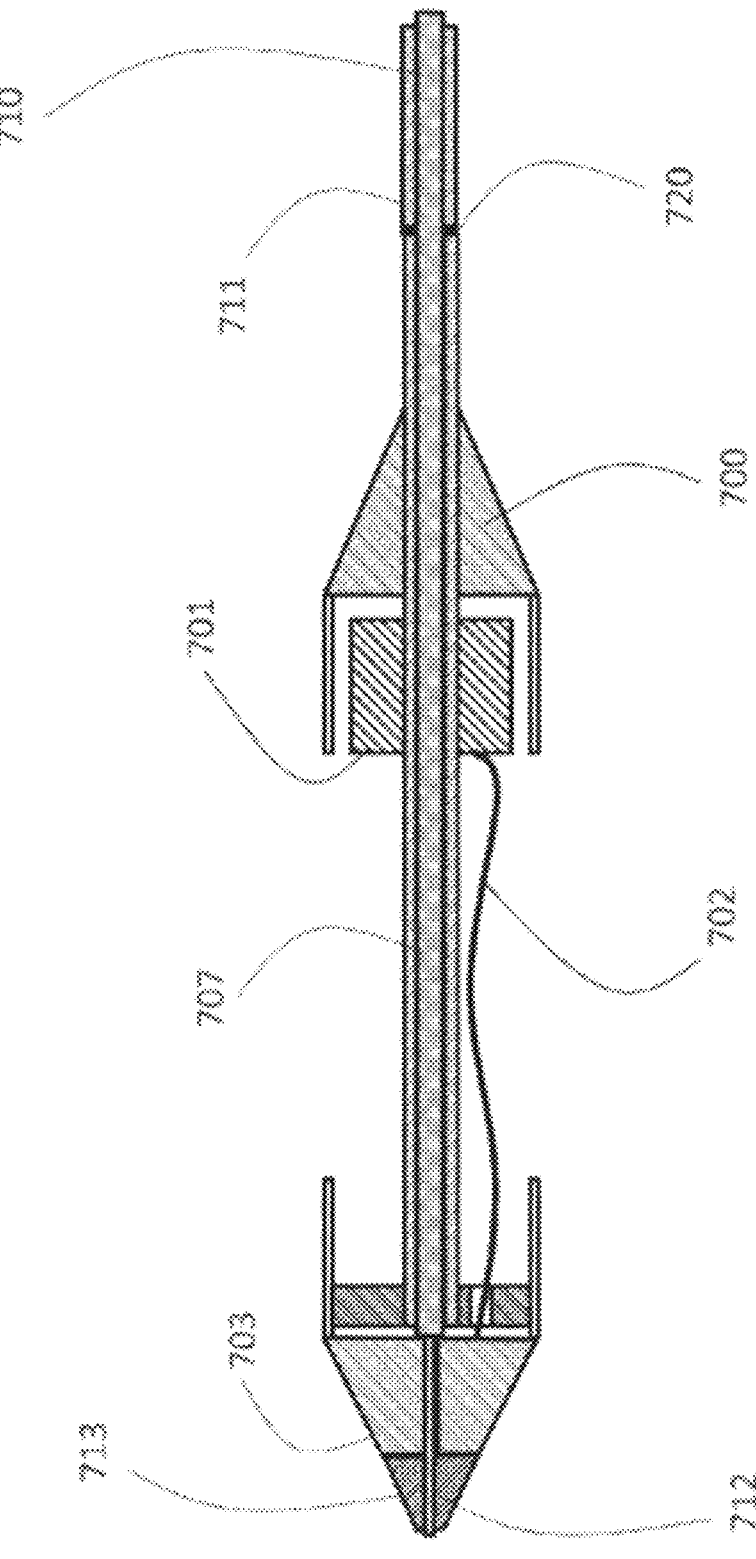
FIG. 20: a third embodiment of the distal section of the delivery system and attachment mechanism to the proximal end of the delivery system partially assembled.

FIGS. 19 and 20 show another embodiment of the two-segment delivery system. In this embodiment, the stent holder (701) is connected with a wire or string (702) to the nose cone (703) of the delivery system as shown in FIG. 19. To operate the distal segment of the delivery system (700) from the proximal end (710) of the delivery system, the outer shaft (707) of the distal end (700) of the delivery system is connected to the outer shaft (711) of the proximal delivery system (710) by a first connecting means (720). The inner shaft (712) of the proximal segment (710) passes through the outer shaft (707) and the nose cone (703) of the distal segment of the delivery system (700). The outer diameter of the inner shaft (712) is reduced as it passes through the nose cone (703) to create a physical interference between the inner shaft (712) and the nose cone (703) at the proximal end of the nose cone (703). FIG. 20 shows the final assembly of the distal segment of the delivery system (700) and the proximal end of the delivery system (710). A nose tip (713) is connected to the distal end of the inner shaft (712) to secure the nose cone to the inner shaft (712). Advancing the inner shaft (712) of the proximal segment of the delivery system (710) distally advances the nosed cone (703), the first sleeve (705) followed by the stent holder (701) similar to the embodiment in FIG. 18.

Valve prostheses are provided in several sizes to treat the wide range of valve anatomies found in patients. For example, aortic valve prostheses may be provided in diameters ranging from 19 mm to 29 mm. Different sizes of valve prosthesis often require different size delivery systems. For example, larger diameter valves may require larger diameter sleeves. Often the length of the valve prosthesis increases with diameter requiring longer pockets and longer sleeves to retain the valve prosthesis. In a further aspect of the current disclosure, a single configuration of the proximal segment of the delivery system is envisioned that can mate and connect to different configurations of the distal delivery system. Since the distal segment of the delivery system is stored with the valve prosthesis, a single proximal segment of the delivery system can be used for all valve sizes. This reduces the inventory of delivery systems needed in the hospital.

Additional features which may serve inter alia to simplify the deployment procedure of a prosthesis in e.g. a percutaneous deployment method may include one or several of the following: a spring loaded eyelet holder, a spring loaded rombi sleeve, a tension spring in the handle of the catheter, a sliding lock, a locator spread, a retraction protector for withdrawal of the catheter, a quick release steering which may include a push wire release and/or an integrated sheath, a cartridge holding the prosthesis, preferably in a preloaded manner. The catheter may be designed in a manner so that each of the above elements are coordinated functioning depending upon their inclusion in the device.

A deployment of a prosthesis may be characterized by one or more of the following steps depending on the inclusion of the above described design features.

Firstly, the prosthesis is loaded onto the capsule of the catheter as described below using a specifically designed loading device. In case of a preloaded prosthesis the unit carrying the prosthesis is combined with the catheter, e.g. by way of a click mechanism. Otherwise the prosthesis is loaded onto the catheter as e.g. described below.

The catheter including the prosthesis is introduced into the vasculature of a patient and pushed upwardly in direction of the heart. After reaching the heart the catheter portion carrying the prosthesis is centered—in case of an aortic heart valve—to be proximal to and essentially in the center of the endogenous aortic heart valve. This centering can be achieved by way of a steering mechanism included in the catheter. In a first step the prosthesis is partially released and in case the prosthesis is exhibiting one or more feelers or locators these parts of the prosthesis are pushed into the pockets of the endogenous valve. This will support a correct positioning of the prosthesis in the correct position. Moreover, the commissures of the prosthesis can be aligned with the endogenous commissures in order to achieve a positioning which is similar to the endogenous symmetry of the valve. In a next step the tip lock (safety clip) is taken off the device and is pushed distally. The proximal part of the catheter holding the prosthesis is thereby moved also distally which can be achieved by a wire connecting the distal and proximal part (stop) carrying the prosthesis. In this manner the proximal part of the prosthesis held in place by a sheath will be released in a second step as a consequence of pushing the distal part (stop) distally. This sequence of deployment steps describes a transfemoral deployment procedure.

In a transapical application of the device, the parts of the catheter and the prosthesis are placed 180° in the other direction.

In an exemplary device as disclosed herein the prosthesis is held and released (deployed) wherein the device has a first movable sleeve and a stop (also denoted as crown or prosthesis holding means) and a second sleeve which is stationary and wherein the stop is movable.

The release of the prosthesis is achieved by way of a release spring and the release is triggered by a release not actuating the release spring. In known devices, the prosthesis is released by way of an actuation from the handle to the catheter part carrying the prosthesis by way of a catheter sleeve. This implied the application of a force of a long distance and wherein the catheter shaft is bent. Accordingly, the transmission of the force applied is problematic. There may even occur cases where the force cannot be transmitted and as a result the prosthesis is not released and jams. The advantage of a design and release mechanism according to some aspects of the present disclosure is that the release procedure is not only more direct and such forces are no longer required but that the release procedure is more reliable.

The release procedure can also be denoted a "single release" mechanism. Advantage of such a single release is that it avoids friction in the system which may be problematic. It involves less movable parts and thus implies less risk of malfunction. The system as disclosed implies less steps and accordingly is more convenient for the operator to use it. The catheter shaft contains less parts, and thus the system may be more flexible and easier to operate through the vasculature. In view of the lower number of parts also less safety parts are required, which may simplify the procedure and/or increase the success rate. Thus operator mistakes are avoided.

The catheter can be combined with a sheath system which may be preshaped and can be designed to be steerable. The sheath may be have a hydrophilic coating. The outer diameter may be 20 F to 22 F, preferably 21 F, and the inner diameter may have a size 18 F to 20 F, preferably 19 F. The outer sheath may exhibit a click mechanism to combine it with the catheter and to release it again after deployment of the prosthesis.

The catheter may comprise the following features at its distal part where the prosthesis is loaded. The catheter may comprise a flexible tip, a sealing ring sleeve to hold the distal region of the prosthesis, a retraction taper, a control wire, a proximal stent holder means, preferably with openings for holding the eyelets of the prosthesis, and a ferrule sleeve, which parts are connected with a handle for actuating and operating the deployment procedure.

The handle comprises a release mechanism which actuates the prosthesis deployment and exhibits a guidewire luer. The sealing ring release spring is secured by means of a tip lock which can be taken off the handle for deployment.

The catheter containing the loaded prosthesis can be introduced by means of a transition tube into the outer sheath and introduced into the vasculature up to the heart.

A prosthesis which is deployed by use of the above described catheter and delivery system can be loaded by generally known means or specifically adapted devices and methods known in the art. Moreover, an exemplary specifically designed loading device will be described in the following. The prosthesis as disclosed herein can also be stored and/or transported in a special device as described below containing a solution which serves inter alia to protect the prosthesis.

In another aspect the disclosure relates to a specific release mechanism useful for deployment of the prosthesis at its target site in the patient's heart.

Figure 21:
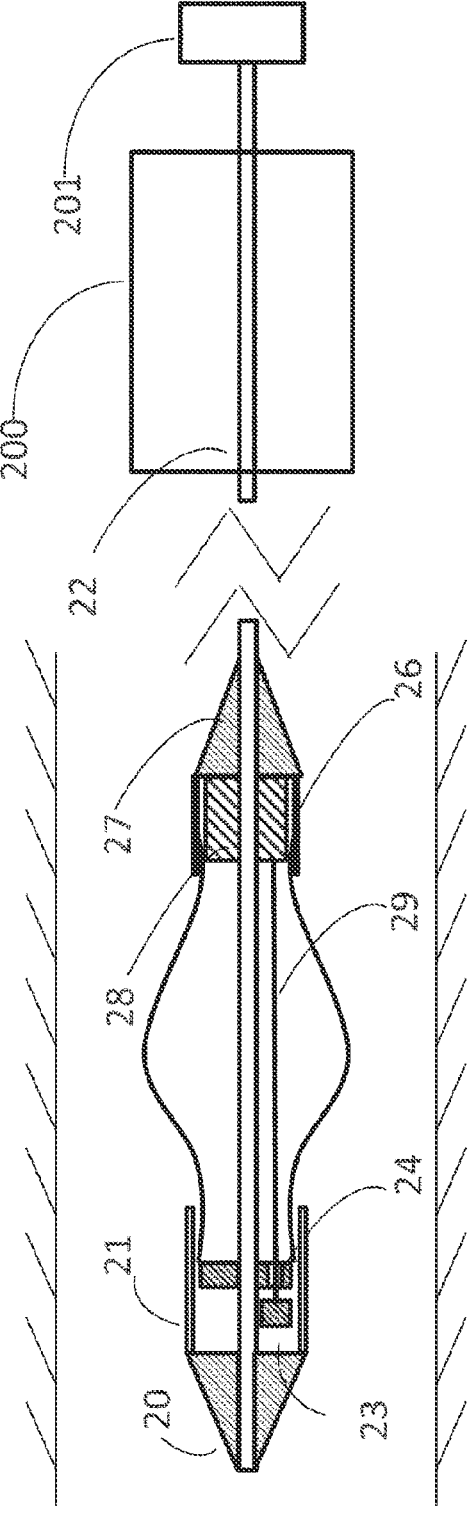
FIGS. 21-23: a pull-wire one-actuator release mechanism of a transcatheter heart valve (THV) and sequence of release.

In FIG. 21, the bend stylized prosthesis is mounted on the distal part of the delivery system. First sleeve (21) covers the distal part of the prosthesis and a second sleeve (26) covers and holds the proximal part of the prosthesis wherein back mount (27) and nose cone (20) are located proximal and distal, respectively. The pull wire or cable (29/29a) connects the proximal stent holder (28) and the distal part as indicated by reference numbers (23) and (24). The handle (200) is connected by way of first shaft (22) with the nose cone (20) passing through stent holder (28). Plunger (201) serves to actuate the release of the prosthesis.

Figure 22:
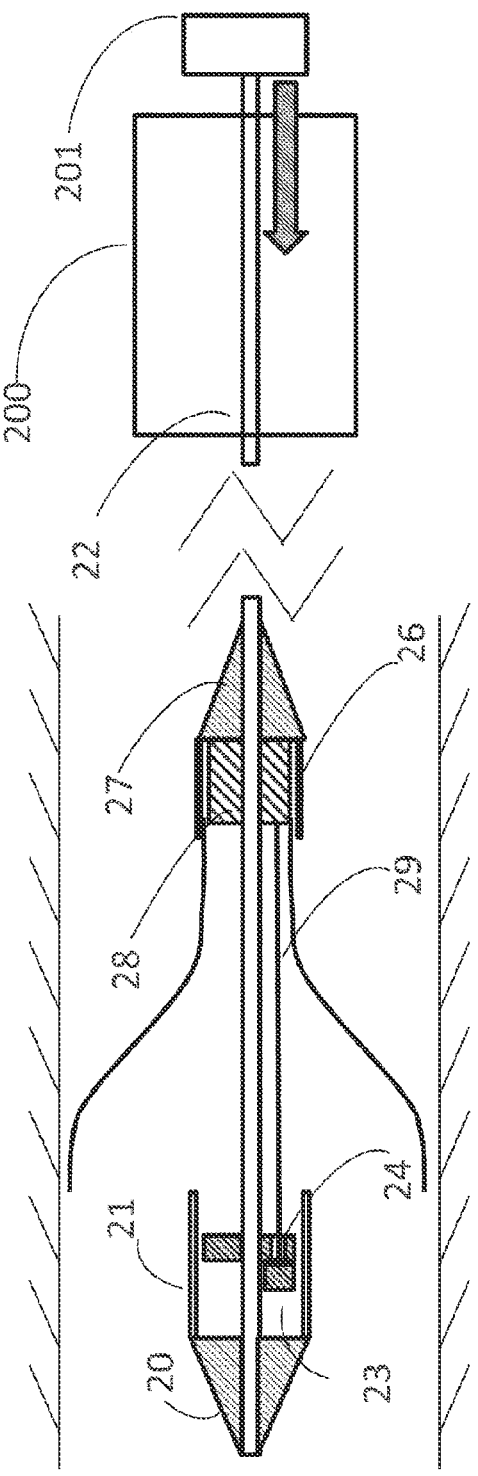

In FIG. 22 plunger (201) is pushed distally whereby the first sleeve (21) releases the distal part of the prosthesis. Front stop (23) moves closer to front stop and the passage indicated (24). The arrow indicates the movement.

Figure 23:
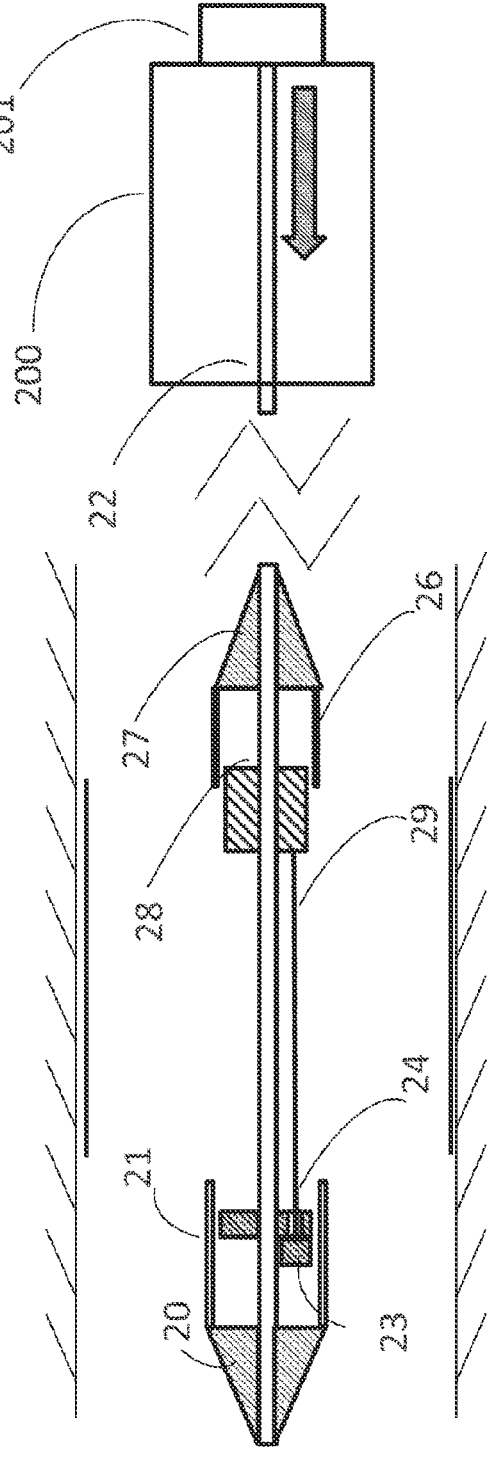

In FIG. 23 the plunger (201) is pushed further in distal direction and thus moves the nose cone (20) further distally whereby pulling by cable (29/29*a*) the stent holder (28) further in distal direction. The second sleeve (26) connected to the back mount (27) remains static whereby the proximal part of the prosthesis is released fully. The arrow indicates the movement. Thus by way of one actuator a two-step release and deployment sequence can be achieved wherein one sleeve (21) is moved and a second sleeve (26) is being kept static wherein the front part of the catheter is moved distally and leads to a complete release of the prosthesis.

Figure 24:
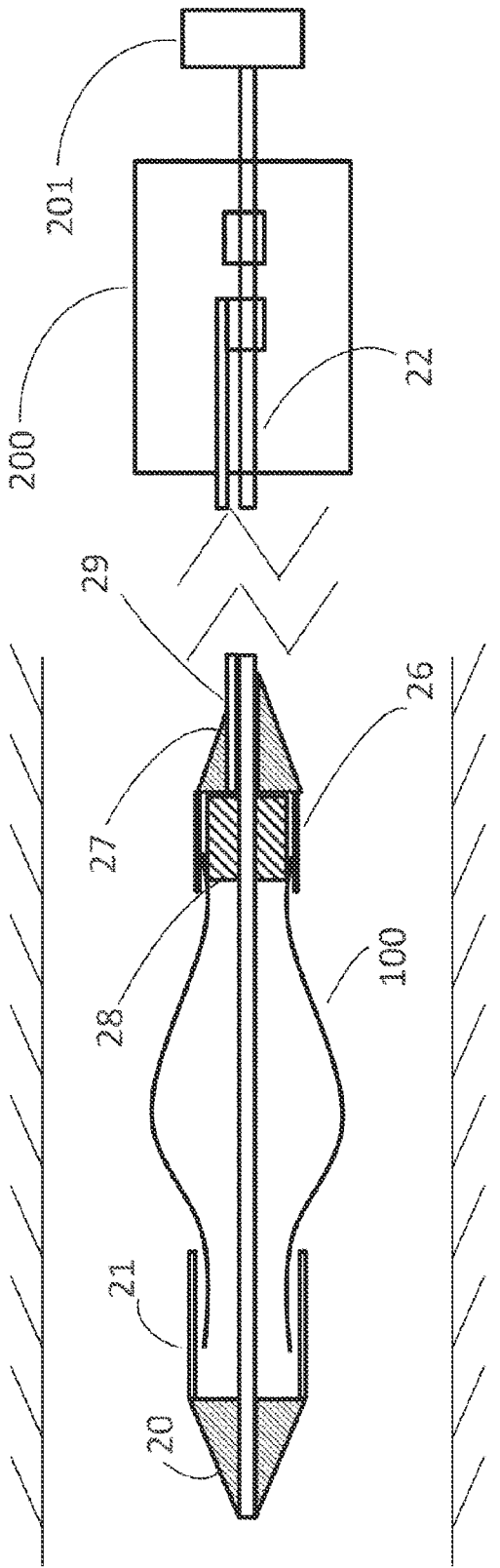
FIGS. 24-26: a push-wire one-actuator release mechanism of a THV and sequence of release.
Figure 25:
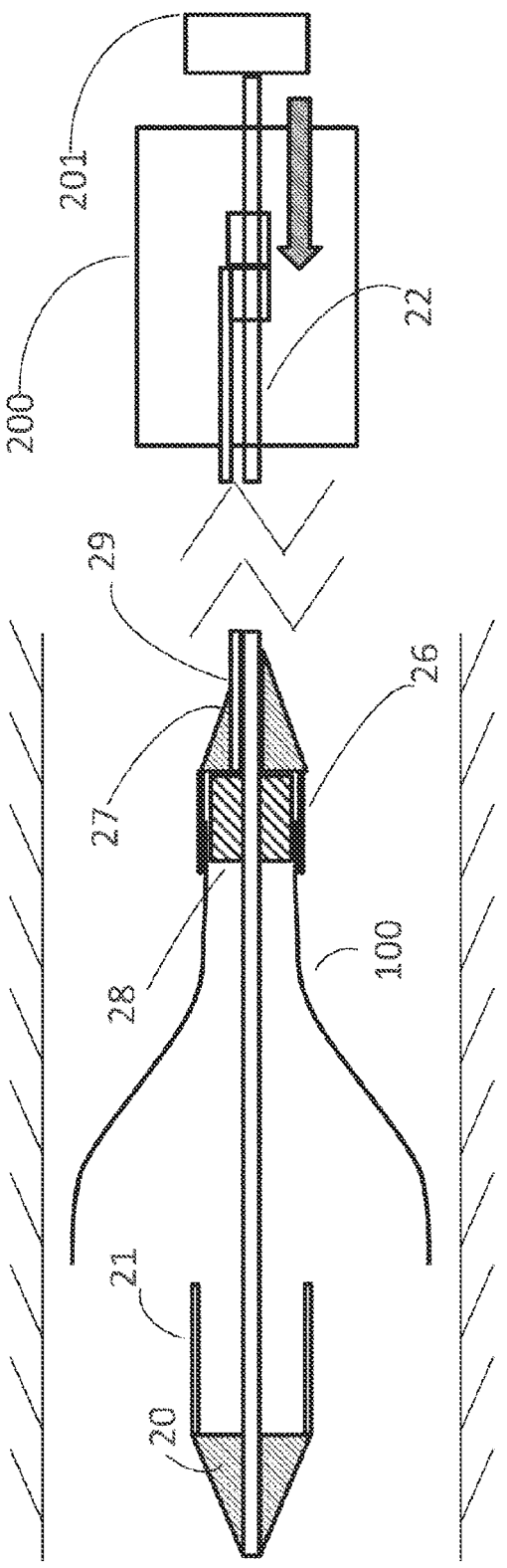
Figure 26:
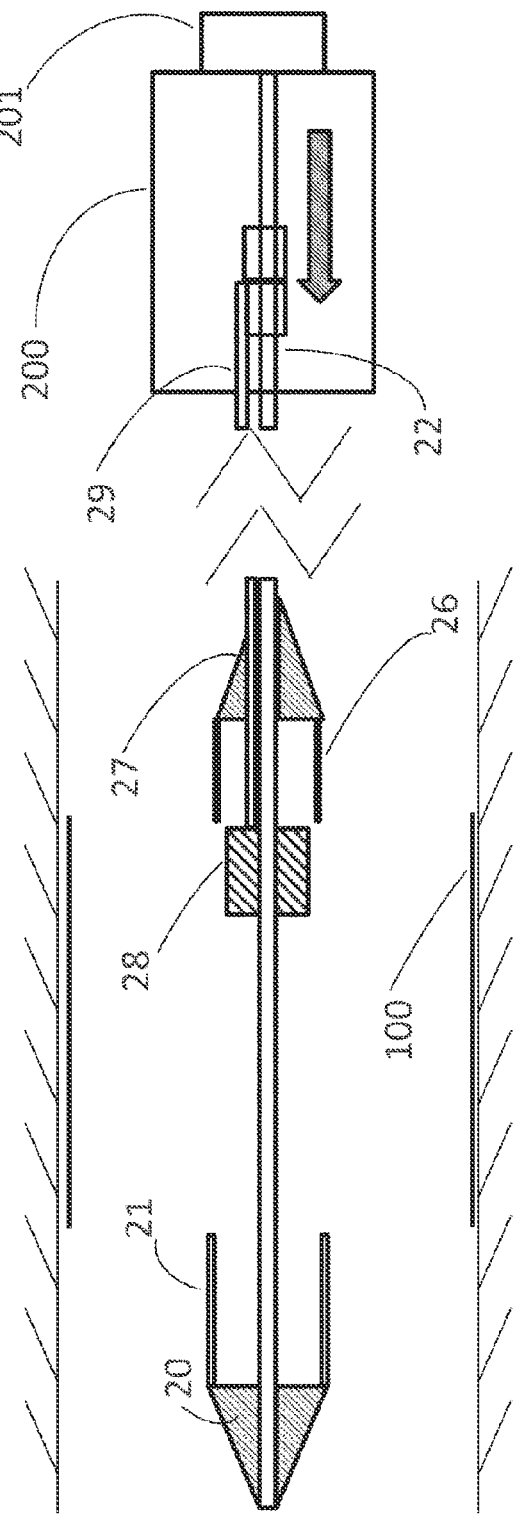

In FIGS. 24-26, the release and deployment of the pros-thesis is performed in the same sequence as in FIGS. 21-23, however, by way of a push mechanism.

In FIG. 24, the handle (200) comprises a plunger (201) which moves a first shaft (22). A shaft (29/29*b*) is connected with proximal stent holder (28). The prosthesis is mounted in the capsule by way of a distal first sleeve (21) and a proximal second sleeve (26). The stent holder (28) is con-nected to the handle to a stop. The plunger (201) can actuate a first shaft (22) to which a stop is connected in the handle and which first shaft (22) is also connected with the nose cone and first sleeve (21).

In FIG. 25, the arrow indicates the movement during deployment and the release procedure. Accordingly, a part connected to the first sleeve (22) is pushed distally and actuates the release of the prosthesis from the distal part of the catheter by way of pushing the first sleeve (21) distally and liberating the distal part of the prosthesis.

In FIG. 26, the plunger (201) is pushed further distally and thus pushes the stop and shaft (29/29*b*) distally thus pushing the stent holder (28) distally which leads to the liberation of the proximal part of the prosthesis and its release from the catheter and full release and deployment.

Accordingly FIGS. 21-23 and 24-26 represent the same principle wherein one actuator can actuate two parts of a capsule holding a stent or prosthesis by way of a distal movement of the actuator and a connecting means (29/29*a* and 29*b*).

In another aspect, the disclosure relates to a specific safety feature in a catheter to lock the loaded prosthesis and to prevent unintentional release from the catheter.

Figure 27:
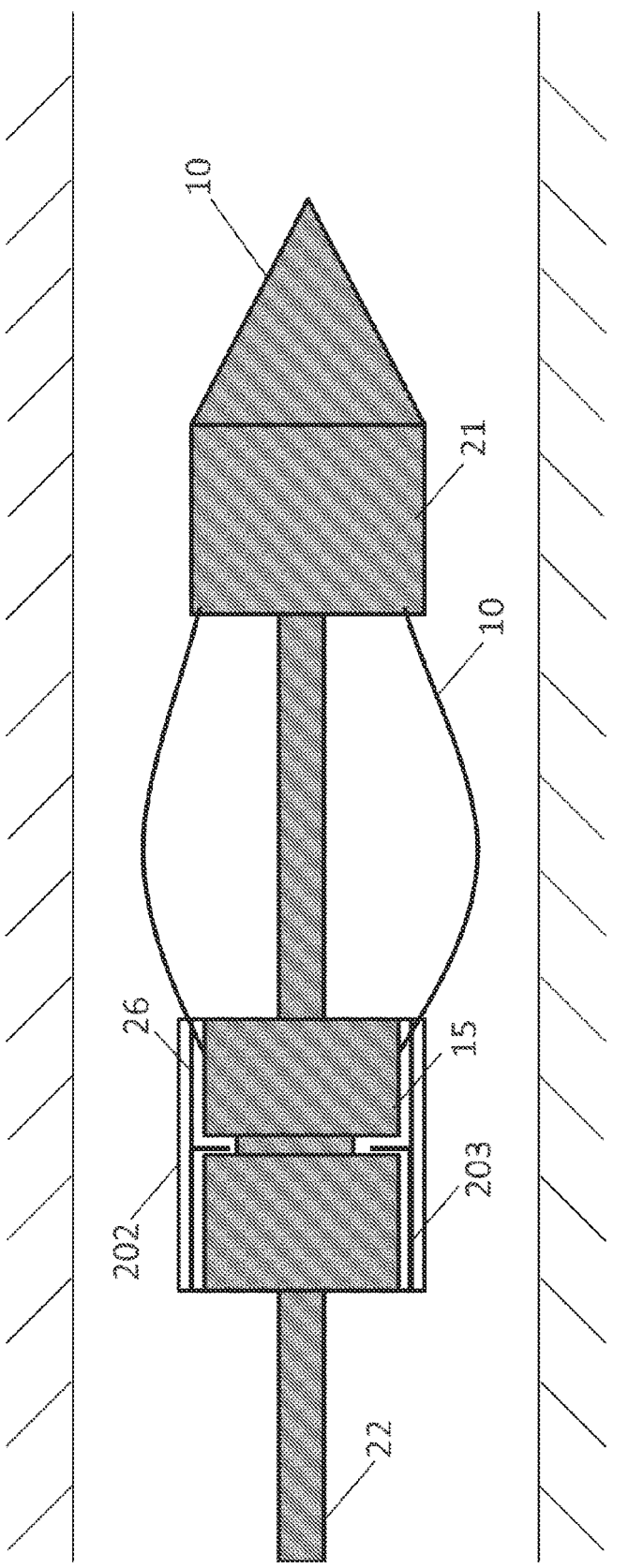
FIGS. 27-30: ferrule locking clips as safety feature useful against unintentional release of the THV from the catheter.
Figure 28:
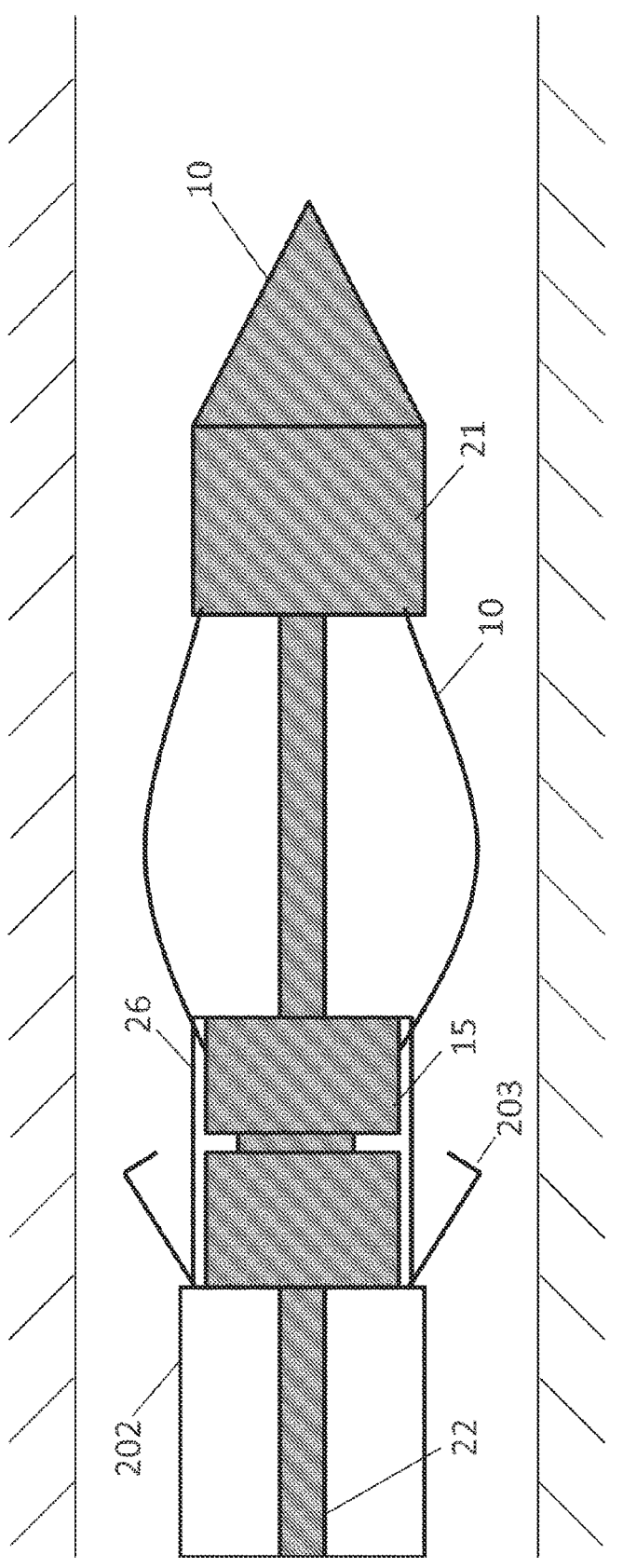

FIG. 27 depicts a safety means designed to avoid prema-ture release of the prosthesis from the catheter by way of a locking clip (203). Prosthesis (103) is held inter alia by second sleeve (26) on stent holder (15) which is character-ized by a slit designed to be accessible by locking clip (203). First sleeve (21) holds the distal part of the prosthesis (103). When a locking sleeve (202) is pushed distally it effects opening of the locking clip (203) and radial movement of same (cf. FIG. 28).

Figure 29:
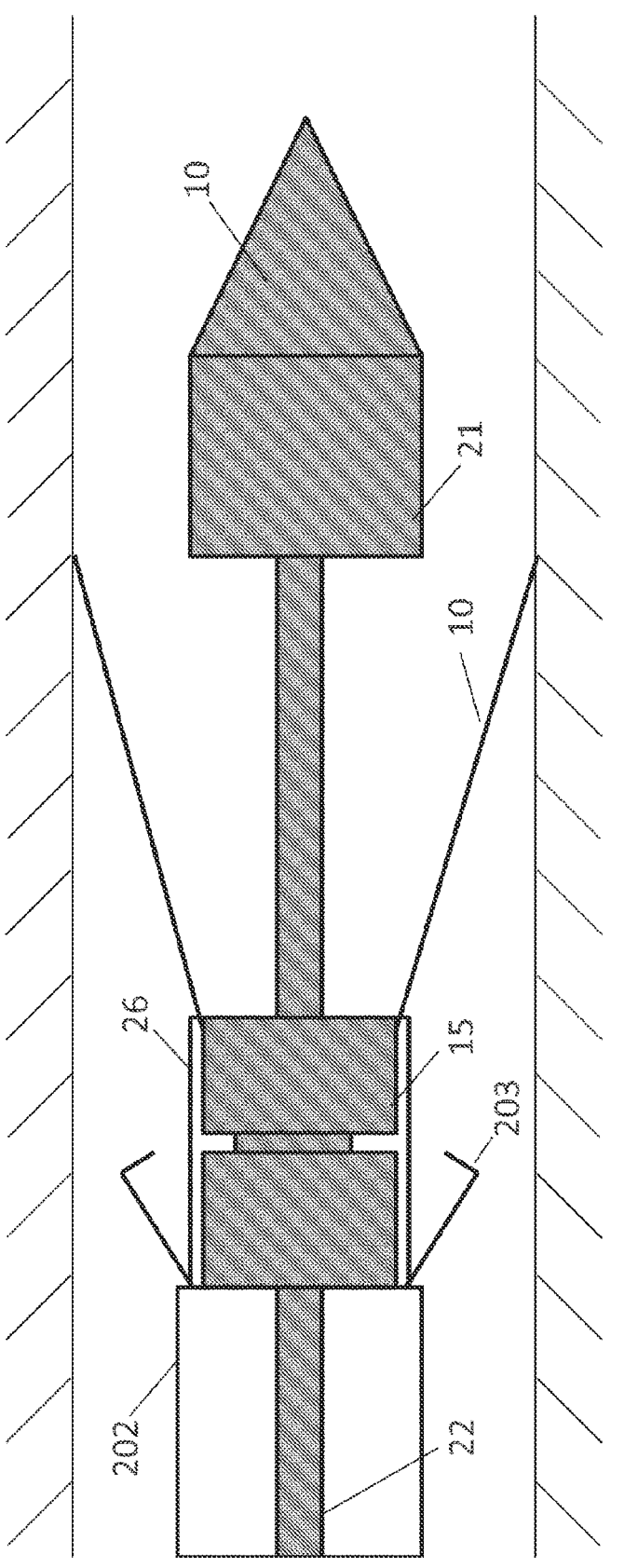

FIG. 29 shows that only after the opening of the locking clip (203) the distal tip and the first sleeve (21) can be pushed distally by way of distal movement of first shaft (22) and the release of the distal part of the prosthesis is effected by way of distal movement of first shaft (22) and first sleeve (21).

Figure 30:
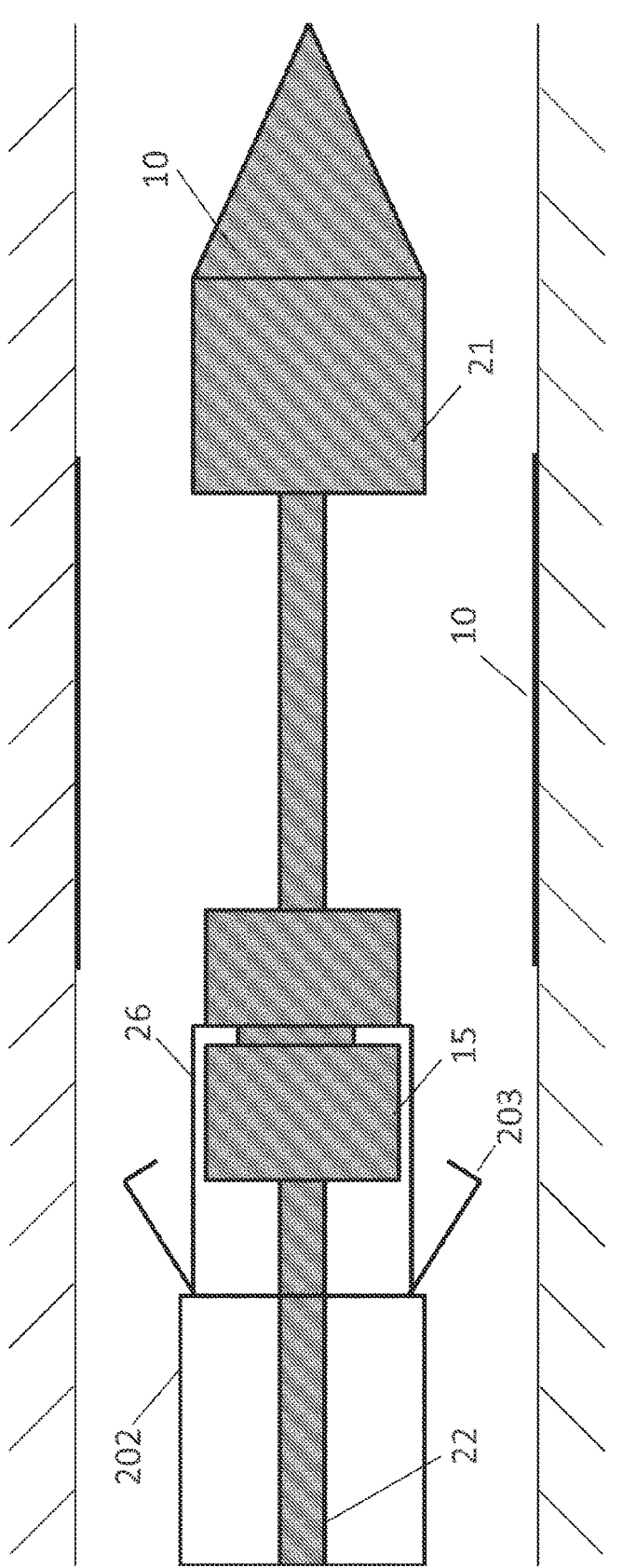

FIG. 30 shows further distal movement of first shaft (22) whereby the stent holder (15) is moved distally and the second sleeve (26) does no longer cover the proximal part of the prosthesis leading to its release and complete release from the catheter tip capsule.

In another aspect the disclosure relates to a loading device particularly useful for loading a transcatheter heart valve prosthesis on a catheter.

FIGS. 31-36 depict a loading tool for loading a prosthesis onto a catheter capsule for delivery to a patient or into a transport container.

Figure 31:
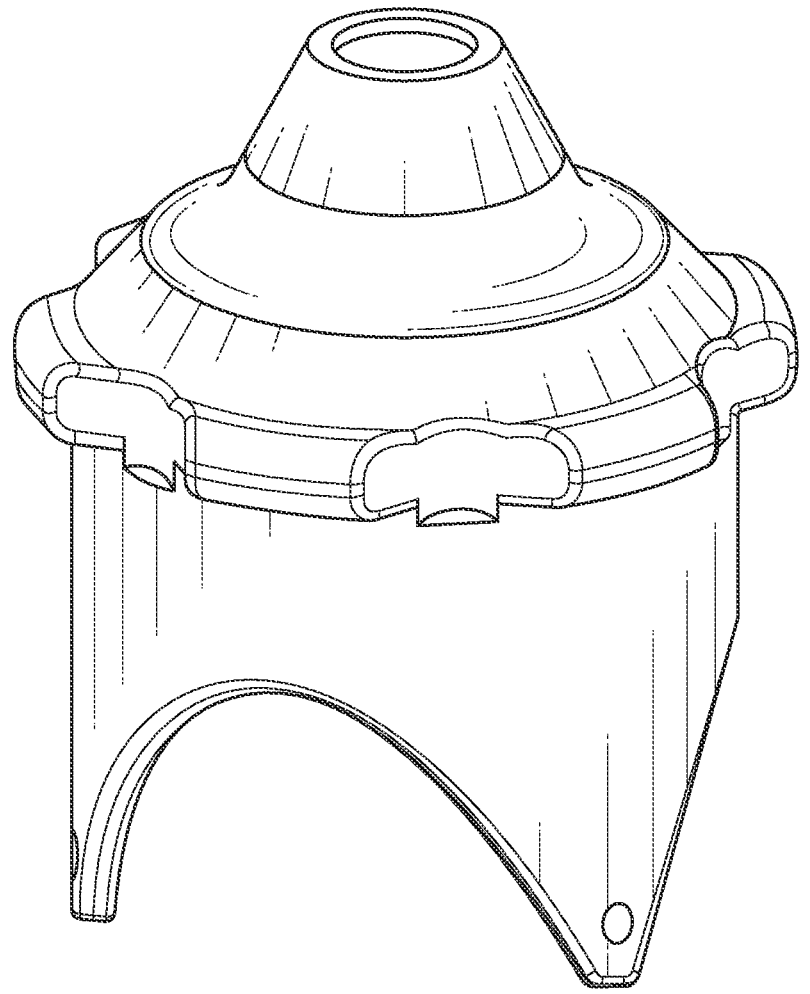
FIGS. 31-38: loading tool components and sequence of use for a THV prosthesis.

The loading part of FIG. 31 is meant to collapse the eyelets so that the eyelets can be captured using axial force generated from rotational force; it also collapses the sealing ring so that the sealing ring can be captured using axial force generated from rotational force.

Figure 32:
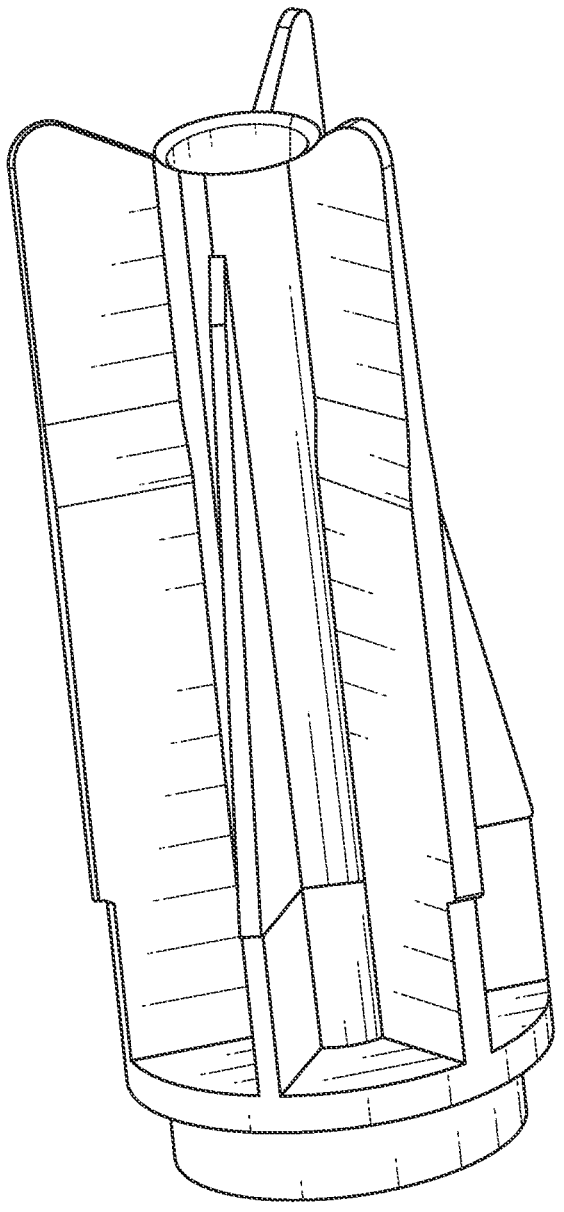

In FIG. 32, a loading part is depicted wherein it provides a base to support the valve during eyelet crimping and during sealing ring extrusion.

Figure 33:
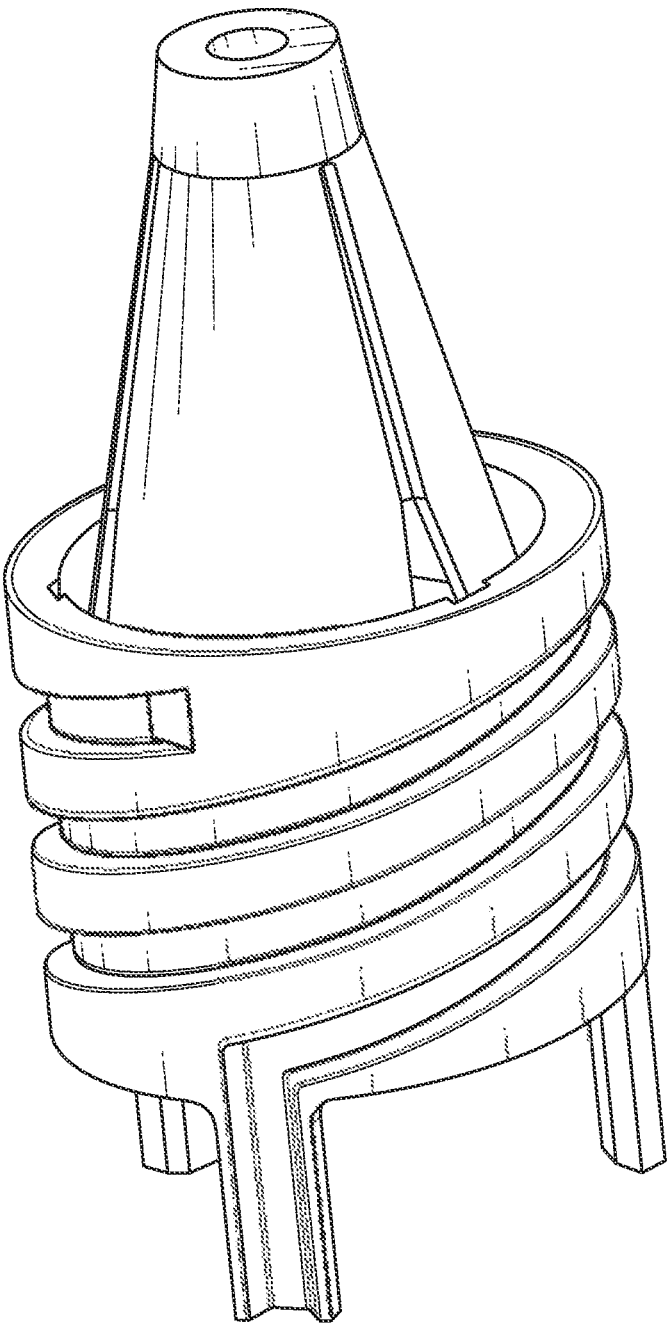

FIG. 33 shows a loading part which provides a track for wheel during eyelet crimping and sealing ring extrusion; moreover it provides contour to collapse sealing ring.

Figure 34:
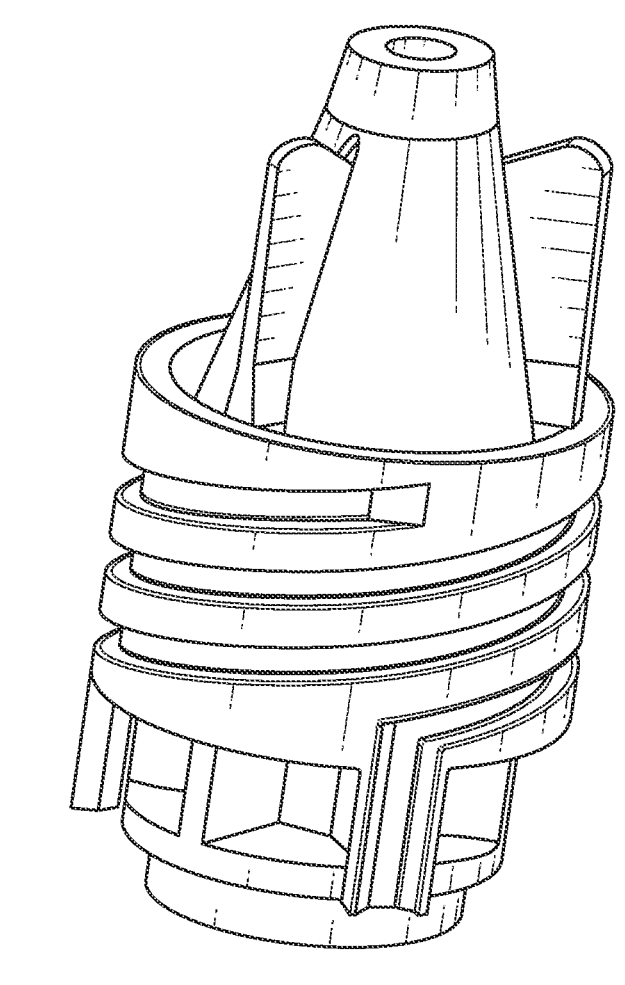
Figure 34:
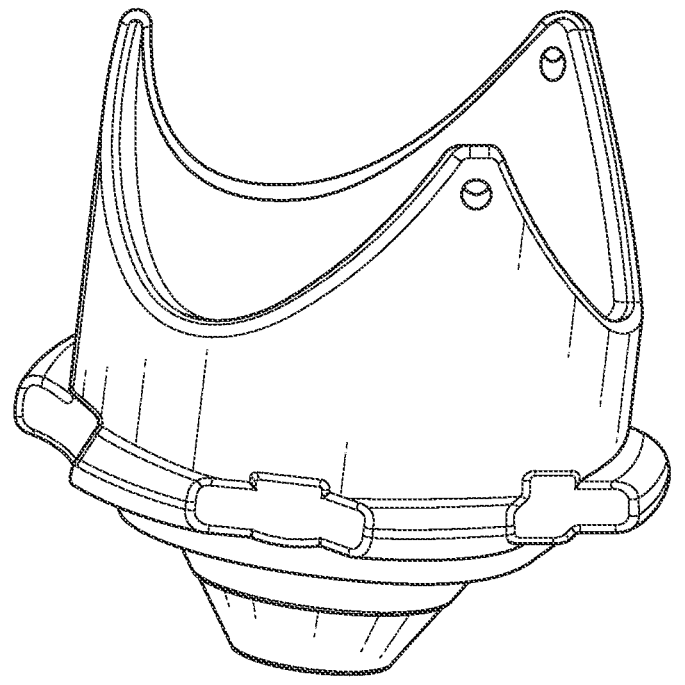

FIG. 34 depicts two parts which are combined together. The prosthesis is placed onto the bottom of one part and the second part collapses the top of the stent of the prosthesis via the interaction between the two parts; this prepares the prosthesis to be mounted onto catheter.

Figure 35:
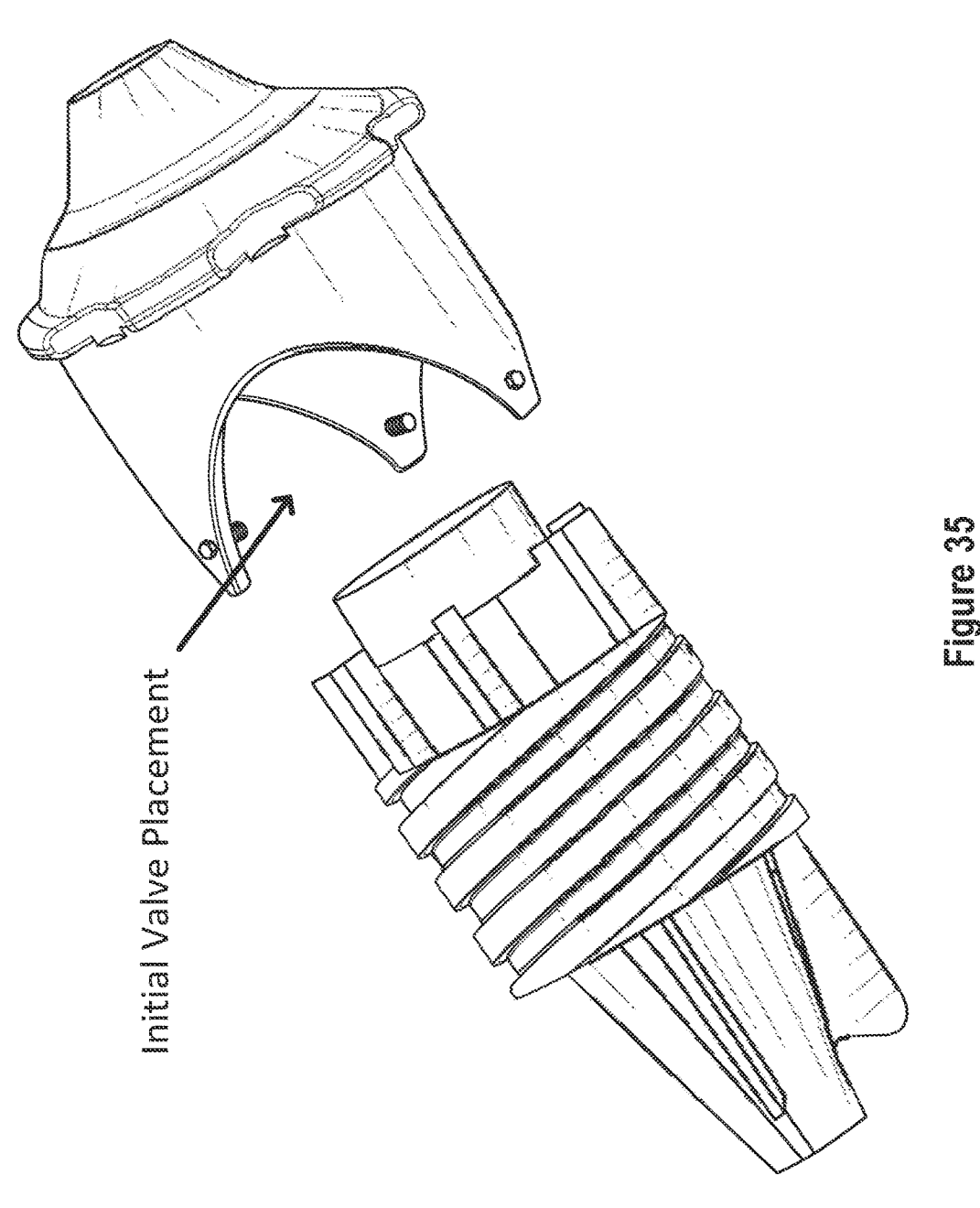

FIG. 35 depicts the parts by which the eyelets of pros-thesis are radially crimped as the wheel is pushed down and rotated along the cone.

Figure 36:
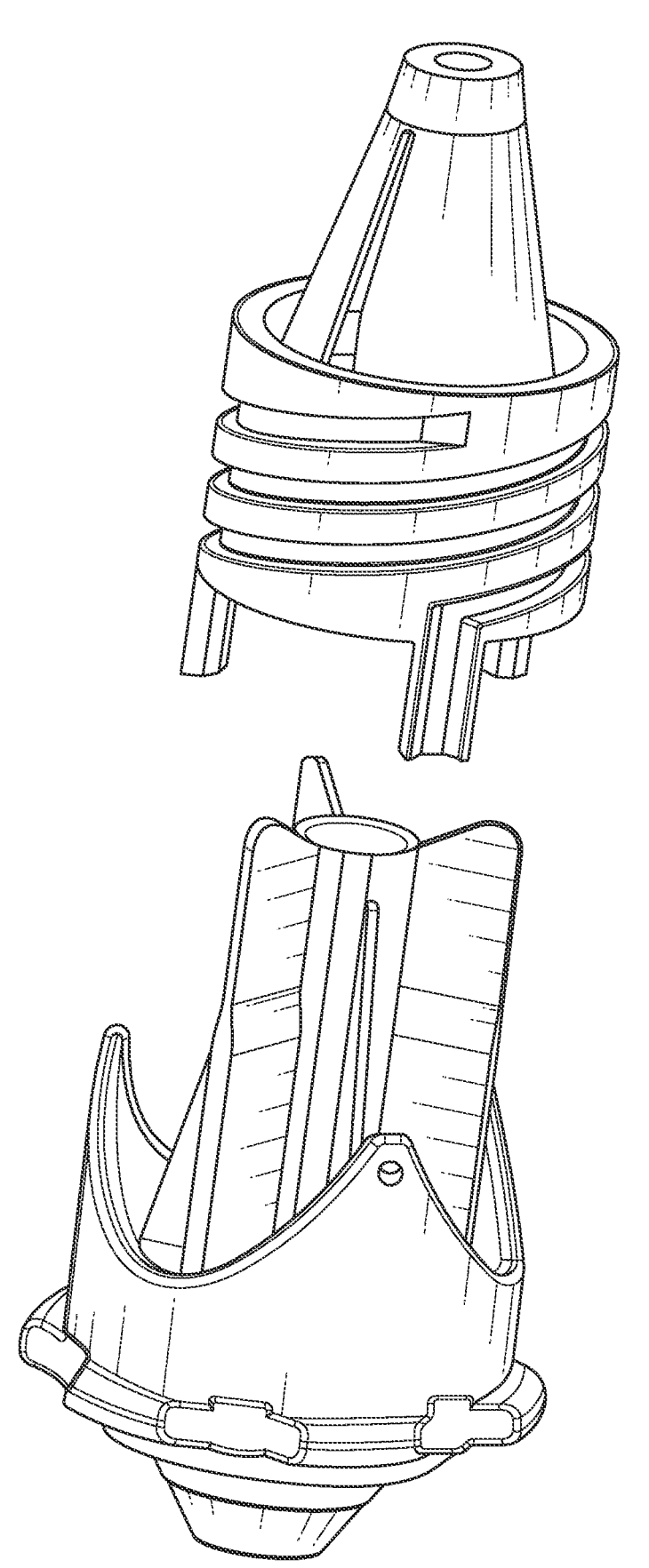

FIG. 36 shows the combination of the two parts which are combined and mounted onto the catheter with the prosthesis sticking outside the top. The assembly is translated to a further part via the threads and crimps the rhombi.

Figure 37:
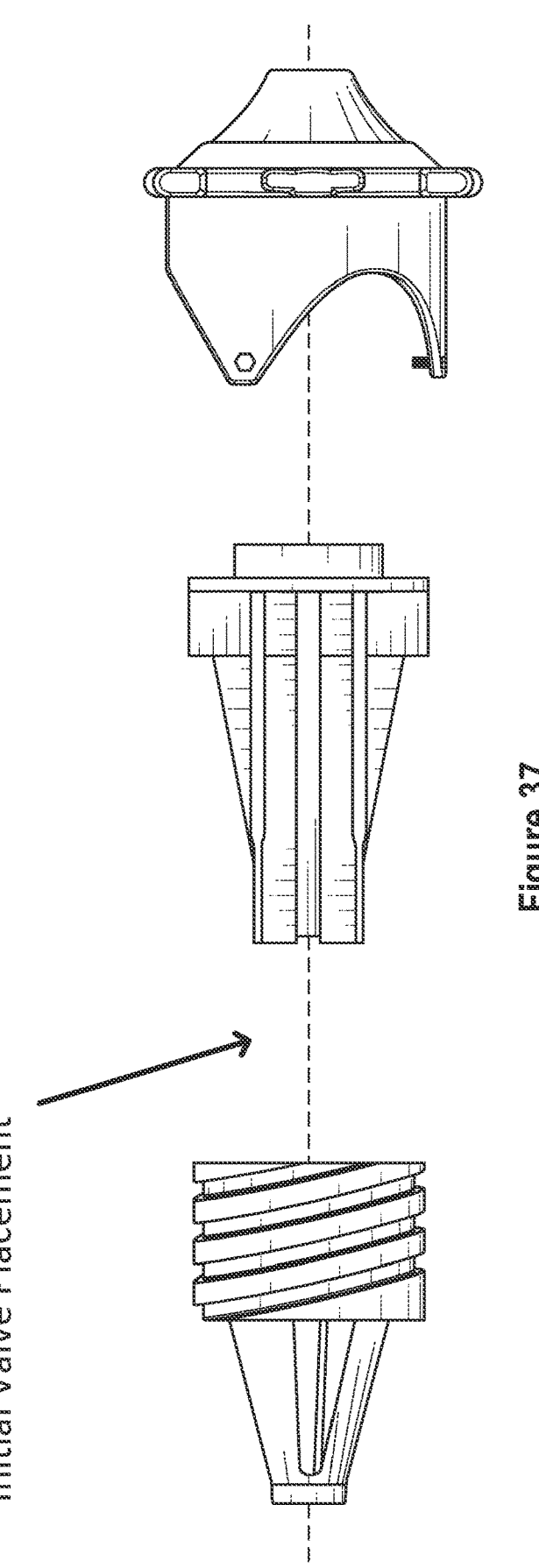

FIG. 37 depicts a step wherein the sealing ring of the prosthesis is radially crimped as the wheel is pushed against the core and rotated along the cone.

Figure 38:
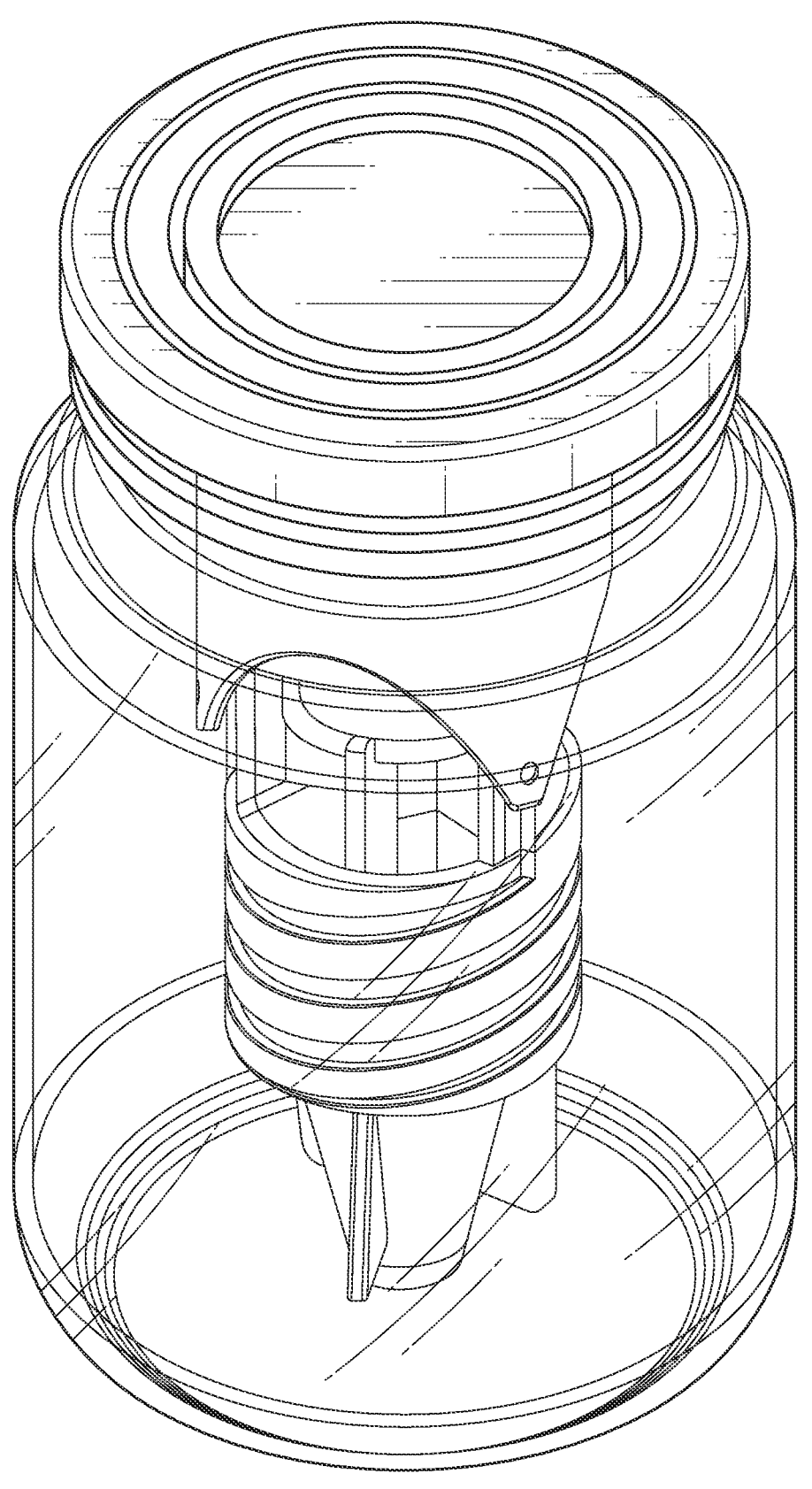

In FIG. 38, the loader and prosthesis are stored together, preferably in a suitable liquid.

REFERENCE NUMBERS

10 nose cone
11 first sleeve
12 first shaft/first catheter shaft
13 front stop
14 second catheter shaft
15 stent holder
16 second sleeve
17 back cone
20 nose cone
21 first sleeve
22 first shaft
23 front stop
24 passage in front stop
25 catheter shaft (second shaft)
26 second sleeve
27 back mount
28 stent holder
29/29*a* cable (pull wire)
29/29*b* shaft for pushing
30 target vessel??? Nose cone???
31 first sleeve
32 first shaft
33 front stop
35 second catheter shaft
36 second sleeve
37 back mount
38 stent holder
39 spring
100 stent
101 second end of stent
102 first end of stent
103 bioprosthetic valve (preferably pericard valve)
104*a-c* eyelets (preferably to secure the stent in the catheter)
105 skirt
105*a-c* eyelets of the stent 200 handle
201 plunger
202 locking sleeve
203 locking clips
300 valve prosthesis
302 proximal end
303 midsection
304 tissue leaflets
310 nose cone
311 first sleeve
312 first shaft
313 front stop
315 stent holder
316 second sleeve
317 back cone
318 second shaft
400 container
401 distal holder
402 proximal holder
403 lid
450 container
451 distal holder
452 rod
460 delivery system
461 guidewire lumen
510 distal segment
511 outer shaft
520 delivery system
521 outer shaft
522 inner shaft
531 outer connector
532 inner connector
601 stent holder
602 wire or string
603 nose cone
604 inner shaft
605 first sleeve
606 second sleeve
607 outer shaft
610 proximal end
611 outer shaft
612 inner shaft
700 delivery system
701 stent holder
702 wire or string
703 nose cone
705 first sleeve
707 outer shaft
710 proximal end
711 outer shaft
712 inner shaft
801 wheel
802 core
803 cone

The invention claimed is:

1. A system for repairing a cardiac valve, the system comprising:

a valve prosthesis a delivery system comprising a handle at a proximal end of the delivery system, an end region at a distal end of the delivery system, and a catheter extending between the handle and the end region of the delivery system, the end region of the delivery system comprising a distal sleeve configured to constrain a distal portion the valve prothesis and a proximal sleeve configured to constrain, together with a stent holder disposed within the proximal sleeve, a proximal portion of the valve prosthesis, the stent holder configured to be removably coupled to the proximal portion of the valve prosthesis and to selectively move with respect to the proximal sleeve, and the valve prosthesis is configured to be sequentially released using the handle in mechanical communication with the end region of the delivery system, the valve prosthesis being self-expandable, wherein the proximal sleeve of the delivery system and the distal sleeve of the delivery system are configured to constrain the valve prosthesis such that an exposed portion of the valve prosthesis extends between the proximal sleeve of the delivery system and the distal sleeve of the delivery system when the distal sleeve of the delivery system is in a proximal-most position and the proximal sleeve of the delivery system is in a distal-most position, the exposed portion self-expanding radially beyond the proximal sleeve of the delivery system and the distal sleeve of the delivery system, and wherein the distal sleeve is configured to move distally to release the distal portion of the valve prosthesis and the stent holder is configured to move distally, subsequent to the distal sleeve moving distally, to fully release the valve prosthesis from the delivery system.

2. The system of claim 1, wherein the valve prosthesis is configured to transition from a radially collapsed state to a radially expanded state.

3. The system of claim 1, wherein the valve prosthesis is stored in a liquid for transport.

4. The system of claim 1, further comprising a steering system, wherein the delivery system and the steering system are releasably connectable.

5. The system of claim 1, wherein the proximal sleeve is axially fixed with respect to the catheter.

6. The system of claim 1, wherein the stent holder is in mechanical communication with the distal sleeve.

7. The system of claim 6, wherein a cable connects stent holder to the distal sleeve.

8. A method for preparing a system for repairing a cardiac valve, the system comprising a valve prosthesis that is self-expandable and a first segment of a delivery system comprising a handle at a proximal end of the delivery system, an end region at a distal end of the delivery system, and a catheter extending between the handle and the end region of the delivery system, the end region of the delivery system comprising a distal sleeve configured to constrain a distal portion the valve prothesis and a proximal sleeve configured to constrain, together with a stent holder disposed within the proximal sleeve, a proximal portion of the valve prosthesis, the stent holder configured to be removably coupled to the proximal portion of the valve prosthesis and to selectively move with respect to the proximal sleeve, the method comprising:

engaging the stent holder of the delivery system with the valve prosthesis, engaging the distal sleeve of the delivery system with the distal portion of the valve prosthesis; and wherein the proximal sleeve of the delivery system and the distal sleeve of the delivery system are configured to contact and constrain the valve prosthesis such that an exposed portion of the valve prosthesis extends between the proximal sleeve of the delivery system and the distal sleeve of the delivery system when the distal sleeve of the delivery system is in a proximal-most position and the proximal sleeve of the delivery system is in a distal-most position, the exposed portion self-expanding radially beyond the proximal sleeve of the delivery system and the distal sleeve of the delivery system, and wherein the distal sleeve is configured to move distally to release the distal portion of the valve prosthesis and the stent holder is configured to move distally, subsequent to the distal sleeve moving distally, to fully release the valve prosthesis from the delivery system.

9. The method of claim 8, wherein engaging the valve prosthesis with the stent holder of the delivery system comprises coupling the valve prosthesis to the stent holder of the delivery system.

10. The method of claim 8, further comprising connecting the delivery system to a steering system adapted to align the valve prosthesis with the cardiac valve.

11. The method of claim 8, wherein the proximal sleeve is axially fixed with respect to the catheter.

12. The method of claim 8, wherein the stent holder is in mechanical communication with the distal sleeve.

13. The method of claim 12, wherein a cable connects stent holder to the distal sleeve.

* * * * *